United States Patent
Merrill et al.

(10) Patent No.: US 8,563,623 B2
(45) Date of Patent: Oct. 22, 2013

(54) RADIATION MELT TREATED ULTRA HIGH MOLECULAR WEIGHT POLYETHYLENE PROSTHETIC DEVICES

(75) Inventors: Edward W. Merrill, Belmont, MA (US); William H. Harris, Belmont, MA (US); Murali Jasty, Weston, MA (US); Orhun Muratoglu, Cambridge, MA (US); Charles R. Bragdon, Weymouth, MA (US); Daniel O. O'Connor, East Taunton, MA (US); Premnath Venugopalan, Cambridge, MA (US)

(73) Assignees: The General Hospital Corporation, Boston, MA (US); Massachusetts Institute of Technology, Cambridge, MA (US)

(*) Notice: Subject to any disclaimer, the term of this patent is extended or adjusted under 35 U.S.C. 154(b) by 0 days.

(21) Appl. No.: 11/006,786

(22) Filed: Dec. 8, 2004

(65) Prior Publication Data
US 2005/0165495 A1    Jul. 28, 2005

Related U.S. Application Data

(63) Continuation of application No. 09/764,554, filed on Jan. 19, 2001, which is a continuation of application No. 09/572,324, filed on May 18, 2000, now abandoned, which is a continuation of application No. 08/798,638, filed on Feb. 11, 1997, now abandoned, which is a continuation-in-part of application No. 08/726,313, filed on Oct. 2, 1996, now abandoned.

(51) Int. Cl.
    *C08F 2/46* (2006.01)
    *A61F 2/02* (2006.01)
    *A61F 2/30* (2006.01)
    *A61F 2/32* (2006.01)
    *A61F 2/64* (2006.01)

(52) U.S. Cl.
    USPC ............... 522/161; 623/11.11; 623/16.11; 623/18.11; 623/20.14; 623/22.11; 623/23.58

(58) Field of Classification Search
    USPC ......... 522/161, 157; 623/11.11, 16.11, 18.11, 623/20.11, 22.11, 23.58
    See application file for complete search history.

(56) References Cited

U.S. PATENT DOCUMENTS

| | | | |
|---|---|---|---|
| 2,904,480 A | 9/1959 | Rainer et al. | 204/154 |
| 2,948,666 A | 8/1960 | Lawton | 204/154 |

(Continued)

FOREIGN PATENT DOCUMENTS

| | | |
|---|---|---|
| AU | B-64364/94 | 12/1994 |
| EP | 0373800 B1 | 6/1990 |

(Continued)

OTHER PUBLICATIONS

Atkinson, Silane Cross-Linked HDPE for Prosthetic Applications, Polymers in Med. and Surgery, Conf. Held by Plastics & Rubber Inst. & Biological Eng. Soc. (1989).

(Continued)

*Primary Examiner* — Sanza McClendon
(74) *Attorney, Agent, or Firm* — Perkins Coie LLP

(57) ABSTRACT

A medical prosthesis for use within the body which is formed of radiation treated ultra high molecular weight polyethylene having substantially no detectable free radicals, is described. Preferred prostheses exhibit reduced production of particles from the prosthesis during wear of the prosthesis, and are substantially oxidation resistant. Methods of manufacture of such devices and material used therein are also provided.

25 Claims, 7 Drawing Sheets

(56) References Cited

U.S. PATENT DOCUMENTS

| | | | |
|---|---|---|---|
| 2,989,451 A | 6/1961 | Prochaska | 204/154 |
| 3,022,543 A | 2/1962 | Baird, Jr. et al. | 18/57 |
| 3,057,791 A | 10/1962 | Anderson, Jr. | 204/154 |
| 3,090,770 A | 5/1963 | Gregorian | 260/45.5 |
| 3,162,623 A | 12/1964 | Cairus et al. | 260/87.7 |
| 3,200,056 A | 8/1965 | Bond | 204/154 |
| 3,231,481 A | 1/1966 | Amemiya et al. | 204/154 |
| 3,297,641 A | 1/1967 | Werber et al. | 260/66 |
| 3,330,748 A | 7/1967 | Lawton | 204/158 |
| 3,352,818 A | 11/1967 | Meyer et al. | 260/45.7 |
| 3,362,897 A | 1/1968 | Lawton | 204/159.2 |
| 3,563,869 A | 2/1971 | Rainer et al. | 204/159.2 |
| 3,616,365 A | 10/1971 | Stastny et al. | 204/159.14 |
| 3,698,017 A | 10/1972 | Scales et al. | 3/1 |
| 3,758,273 A | 9/1973 | Johnston et al. | 21/54 R |
| 3,783,115 A | 1/1974 | Zeppenfeld | 204/159.2 |
| 3,832,827 A | 9/1974 | Lemelson | 53/111 R |
| 3,886,056 A | 5/1975 | Kitamaru et al. | 204/159.2 |
| 3,944,536 A | 3/1976 | Lupton et al. | 260/94.9 R |
| 4,226,905 A | 10/1980 | Harbourne | 428/220 |
| 4,241,463 A | 12/1980 | Khovaylo | 3/1.913 |
| 4,281,420 A | 8/1981 | Raab | 3/1.912 |
| 4,385,405 A | 5/1983 | Teinturier | 3/1.912 |
| 4,524,467 A | 6/1985 | DeCarlo, Jr. | 603/22 |
| 4,525,257 A | 6/1985 | Kurtz et al. | 204/159.2 |
| 4,535,486 A | 8/1985 | Roberts et al. | 623/22 |
| 4,586,995 A | 5/1986 | Randall et al. | 522/5 |
| 4,587,163 A | 5/1986 | Zachariades | 428/292 |
| 4,655,769 A | 4/1987 | Zachariades | 623/1 |
| 4,701,288 A | 10/1987 | Cook et al. | 264/1.4 |
| 4,747,990 A | 5/1988 | Gaussens et al. | 264/22 |
| 4,813,210 A | 3/1989 | Masuda et al. | 53/425 |
| 4,820,466 A | 4/1989 | Zachariades | 264/119 |
| 4,832,965 A | 5/1989 | Helin | 426/66 |
| 4,870,136 A | 9/1989 | Yagi et al. | 525/288 |
| 4,888,141 A | 12/1989 | Bastiaansen et al. | 264/22 |
| 4,892,552 A | 1/1990 | Ainsworth et al. | 623/23 |
| 4,902,460 A | 2/1990 | Yagi et al. | 264/83 |
| 4,916,198 A | 4/1990 | Scheve et al. | 526/351 |
| 4,944,974 A | 7/1990 | Zachariades | 428/298 |
| 4,950,151 A | 8/1990 | Zachariades | 264/146 |
| 4,954,299 A | 9/1990 | Greig et al. | 264/22 |
| 5,001,008 A | 3/1991 | Tokita et al. | 428/400 |
| 5,001,206 A | 3/1991 | Bashir et al. | 526/352 |
| 5,014,494 A | 5/1991 | George | 53/425 |
| 5,015,525 A | 5/1991 | Yagi et al. | 428/364 |
| 5,017,627 A | 5/1991 | Bonfield et al. | 523/115 |
| 5,019,105 A | 5/1991 | Wiley | 623/22 |
| 5,024,670 A | 6/1991 | Smith et al. | 623/18 |
| 5,030,402 A | 7/1991 | Zachariades | 264/138 |
| 5,037,928 A | 8/1991 | Li et al. | 526/352 |
| 5,047,446 A | 9/1991 | DeNicola, Jr. | 522/157 |
| 5,059,196 A | 10/1991 | Coates | 606/99 |
| 5,066,755 A | 11/1991 | Lemstra | 526/348.1 |
| 5,082,869 A | 1/1992 | Braga et al. | 521/134 |
| 5,096,654 A | 3/1992 | Craggs et al. | 264/570 |
| 5,123,924 A | 6/1992 | Sioshansi et al. | 623/16 |
| 5,123,925 A | 6/1992 | Smestad et al. | 623/16 |
| 5,153,039 A | 10/1992 | Porter et al. | 428/36.92 |
| 5,160,464 A | 11/1992 | Ward et al. | 264/22 |
| 5,160,472 A | 11/1992 | Zachariades | 264/136 |
| 5,160,677 A | 11/1992 | Gravener et al. | 264/101 |
| 5,164,464 A | 11/1992 | Hefner, Jr. et al. | 525/531 |
| 5,200,439 A | 4/1993 | Asanuma | 522/157 |
| 5,292,584 A | 3/1994 | Howard et al. | 428/327 |
| 5,352,732 A | 10/1994 | Howard | 524/789 |
| 5,358,792 A | 10/1994 | Mehta et al. | 428/516 |
| 5,407,623 A | 4/1995 | Zachariades et al. | 264/119 |
| 5,414,049 A | 5/1995 | Sun et al. | 525/333.7 |
| 5,428,079 A | 6/1995 | Bastiaansen et al. | 522/161 |
| 5,449,745 A | 9/1995 | Sun et al. | 528/483 |
| 5,466,530 A | 11/1995 | England et al. | 428/411.1 |
| 5,478,906 A | 12/1995 | Howard, Jr. | 526/352 |
| 5,480,683 A | 1/1996 | Chabrol et al. | 427/525 |
| 5,507,446 A | 4/1996 | Ditzig | 242/372 |
| 5,508,319 A | 4/1996 | DeNicola, Jr. et al. | 522/161 |
| 5,515,590 A | 5/1996 | Pienkowski | 29/404 |
| 5,543,471 A | 8/1996 | Sun et al. | 525/333.7 |
| 5,543,571 A | 8/1996 | Burk | 564/150 |
| 5,549,698 A | 8/1996 | Averill et al. | 623/22 |
| 5,549,700 A | 8/1996 | Graham et al. | 623/22 |
| 5,552,104 A | 9/1996 | DeNicola, Jr. et al. | 264/456 |
| 5,577,368 A | 11/1996 | Hamilton et al. | 53/432 |
| 5,593,719 A | 1/1997 | Dearnaley et al. | 427/2.26 |
| 5,609,643 A | 3/1997 | Colleran et al. | 623/20 |
| 5,650,485 A | 7/1997 | Sun et al. | 528/483 |
| 5,652,281 A | 7/1997 | Galli et al. | 522/114 |
| 5,684,124 A | 11/1997 | Howard, Jr. et al. | 528/481 |
| 5,728,748 A | 3/1998 | Sun et al. | 522/65 |
| 5,753,182 A | 5/1998 | Higgins | 422/23 |
| 5,824,411 A | 10/1998 | Shalaby et al. | 428/364 |
| 5,834,113 A | 11/1998 | Shalaby et al. | 428/364 |
| 5,869,575 A | 2/1999 | Kolthammer et al. | 525/240 |
| 5,874,123 A | 2/1999 | Park | 427/2.24 |
| 5,879,400 A | 3/1999 | Merrill et al. | 623/22 |
| 5,972,444 A | 10/1999 | Patel et al. | 428/35.2 |
| 6,005,053 A | 12/1999 | Parikh et al. | 525/221 |
| 6,017,975 A | 1/2000 | Saum et al. | 522/161 |
| 6,096,084 A | 8/2000 | Townley | 623/23.12 |
| 6,143,232 A | 11/2000 | Rohr | 623/18 |
| 6,165,220 A | 12/2000 | McKellop et al. | 623/18 |
| 6,168,626 B1 | 1/2001 | Hyon et al. | 623/18.11 |
| 6,174,932 B1 | 1/2001 | Pachl et al. | 522/100 |
| 6,174,934 B1 | 1/2001 | Sun et al. | 523/113 |
| 6,184,265 B1 | 2/2001 | Hamilton et al. | 522/189 |
| 6,228,900 B1 | 5/2001 | Shen et al. | 522/153 |
| 6,242,507 B1 | 6/2001 | Saum et al. | 522/161 |
| 6,245,276 B1 | 6/2001 | McNulty et al. | 264/322 |
| 6,281,264 B1 | 8/2001 | Salovey et al. | 523/115 |
| 6,316,158 B1 | 11/2001 | Saum et al. | 430/130 |
| 6,372,814 B1 | 4/2002 | Sun et al. | 522/161 |
| 6,414,086 B1 | 7/2002 | Wang et al. | 525/191 |
| 6,432,349 B1 | 8/2002 | Pletcher et al. | 264/479 |
| 6,436,137 B2 | 8/2002 | Wang et al. | 623/11.11 |
| 6,464,926 B1 | 10/2002 | Merrill et al. | 264/485 |
| 6,494,917 B1 | 12/2002 | McKellop et al. | 623/23.58 |
| 6,503,439 B1 | 1/2003 | Burstein | 264/469 |
| 6,506,866 B2 | 1/2003 | Jacobsen et al. | 526/348 |
| 6,547,828 B2 | 4/2003 | Scott et al. | 623/66 |
| 6,638,311 B2 | 10/2003 | Wang et al. | 623/22.32 |
| 6,641,617 B1 | 11/2003 | Merrill et al. | 623/23.58 |
| 6,786,933 B2 | 9/2004 | Merrill et al. | 623/23.58 |
| 6,818,171 B2 | 11/2004 | Wang et al. | 264/478 |
| 6,849,224 B2 | 2/2005 | Wang et al. | 264/478 |
| 6,905,511 B2 | 6/2005 | Wang et al. | 623/11.11 |
| 7,517,919 B2 | 4/2009 | Wang et al. | 522/161 |
| 2002/0007219 A1 | 1/2002 | Merrill et al. | |
| 2002/0013781 A1 | 1/2002 | Petersen | |
| 2002/0107299 A1 | 8/2002 | Sun et al. | |
| 2003/0013781 A1 | 1/2003 | Merrill et al. | |
| 2003/0105182 A1 | 6/2003 | Merrill et al. | |
| 2003/0119935 A1 | 6/2003 | Merrill et al. | |
| 2003/0229155 A1 | 12/2003 | Wang et al. | |
| 2004/0132856 A1 | 7/2004 | Merrill et al. | |
| 2005/0006821 A1 | 1/2005 | Merrill et al. | |
| 2005/0010288 A1 | 1/2005 | Merrill et al. | |
| 2005/0043431 A1 | 2/2005 | Wang et al. | |
| 2005/0056971 A1 | 3/2005 | Merrill et al. | |
| 2005/0059750 A1 | 3/2005 | Sun et al. | |
| 2005/0096749 A1 | 5/2005 | Marrill et al. | |
| 2005/0113935 A1 | 5/2005 | Wang et al. | |
| 2005/0267594 A1 | 12/2005 | Merrill et al. | |
| 2008/0215142 A1 | 9/2008 | Muratoglu et al. | |
| 2008/0319137 A1 | 12/2008 | Rufner et al. | |

FOREIGN PATENT DOCUMENTS

| | | |
|---|---|---|
| EP | 0 376 503 | 7/1990 |
| EP | 0 218 003 | 11/1990 |
| EP | 0 177 552 | 5/1992 |
| EP | 0 218 993 | 2/1994 |
| EP | 0 373 800 | 5/1994 |
| EP | 0722973 A1 | 7/1996 |
| EP | 0729981 B1 | 9/1996 |

(56) References Cited

FOREIGN PATENT DOCUMENTS

| | | |
|---|---|---|
| EP | 0737481 B1 | 10/1996 |
| EP | 0847765 | 6/1998 |
| EP | 1005872 | 6/2000 |
| EP | 0 729 981 | 3/2002 |
| EP | 0 722 973 | 12/2003 |
| EP | 0 737 481 | 9/2004 |
| GB | 2 060 469 | 5/1981 |
| GB | 2 156 733 | 10/1985 |
| GB | 2 157 298 | 10/1985 |
| GB | 2 180 815 | 4/1987 |
| GB | 2 207 436 | 2/1989 |
| GB | 2 225 551 | 6/1990 |
| JP | 58157830 | 9/1983 |
| JP | 59071830 | 4/1984 |
| JP | 59168050 | 9/1984 |
| JP | 62243634 | 10/1987 |
| JP | 4198242 | 6/1992 |
| JP | 4185651 | 7/1992 |
| JP | 04185651 | 7/1992 |
| JP | 04198242 | 7/1992 |
| WO | WO90/11060 | 10/1990 |
| WO | WO93/10953 | 6/1993 |
| WO | WO94/27651 | 12/1994 |
| WO | WO97/29793 | 8/1997 |
| WO | WO98/01085 | 1/1998 |
| WO | WO00/62717 | 10/2000 |
| WO | WO01/05337 | 1/2001 |
| ZA | 896852 | 9/1989 |

OTHER PUBLICATIONS

Bennett et al., 42$^{nd}$ Annual Meeting, Orthopaedic Research Society, Atlanta, GA (Feb. 19-22, 1996).
De Boer et al., Polymer 23: 1944-1952 (1982).
Dijkstra et al., Polymer 30: 866-873 (1989).
Du Plessis et al., Radiat. Phys. Chem. 9: 647-652 (1977).
Gent et al., J. of Polmer Sci 5: 47-61 (1967).
Gielenz et al., Colloid & Polymer Sci. 260: 742-753 (1982).
Grobbelaar et al., J. of Bone and Joint Surgery 60-B(3): 370-374 (1978).
Grobbelaar et al., SA Bone and Joint Surgery IX(3): 143-147 (1999).
Grulke, Polymer Process Engineering, p. 419, PTR Prentice Hall (1994).
Howmedica, Overview and Fundamentals of UHMWPE, Part 1 of a Series on Ultra-High Molecular Weight Polyethylene, p. 1-8 (1994).
Howmedica, Material Properties, Product Quality Control and Their Relation to UHMWPE Performance, Part 2 of a Series on Ultra High Molecular Weight Polyethylene. p. 1-20 (1994).
Howmedica, A Comparative Analysis Analysis of the Properties of Standard and "Enchanced" Ultra-High Molecular Weight Polyethylene, Part 3 of a Series on ultra High Molecular Weight Polyethylene, p. 1-12 (1994).
Howmedica, Duration Stabilized UHMWPE, A Polyethylene With Superior Resistance to Oxidation, Part 4 of a Series on Ultra High Molecular Weight Polyethylene, p. 1-12 (1998).
Jahan et al., J. of Biomed Research 25: 1005-1016 (1991).
Jahan et al., J. of Luminescence 40 & 41:242-243 (1988).
Kamel et al., J. of Polymer Science: Polymer Physics Edition 23: 2407-2409 (1985).
Kang et al., J. of Amer. Chem. Soc. 89(9): 1980-1986 (1967).
Lancaster, Friction and Wear, Polymer Science, Chapter 14: 960-1046 (1972).
Li et al., The Journal of Bone and Joint Surgery 76-A: 1080-1090 (1994).
Mandelkern et al., National Bureau of Standards 82: 46-53 (1960).
Narkis et al., J. Macromol. Sci Phys. B26(1): 37-58 (1987).
Nusbaum et al., J. of Boimed Material Research 13: 557-576 (1979).
Oonishi et al., Encyclopedic Handbook of Biomaterials and Bioengineering 2: 1853-1868 (1995).
Qu et al., J. of Applied Polymer Science 48: 711-719 (1993).
Ratner et al., Abrasion of Rubber 145-154 (1967).
Rose et al., J. of Orthopaedic Research Society 2(4): 393-400 (1984).
Rose et al., Biomaterials 11: 63-67 (1990).
Rosen, Fundamental Principles of Polymeric Materials, p. 40, John Wiley & Sons, Inc. (1993).
Saunders et al, Medical Device & Diagnostic Industry 222:89-92 (1993).
Shen, Effect of Irradiation on Chemically Crosslinked Ultrahigh Molecular Weight Polyethylene (A Dissertation Presented to the Univ. of Southern California (Dec. 1994)).
Shinde et al., J. of Polymer Science: Polymer Physics Edition 23: 1681-1689 (1985).
Streicher, Investigation on Sterilization and Modification of High Molecular Weight Polyethylenes by Ionizing Irradiation, Beta-Gamma (Jan. 1989).
Zoepfl et al., J. Polymer Sci Polym. Chem. Ed 22: 2017-2032 (1984).
Zoepfl et al., J. Polymer Sci Polym. Chem. Ed 22: 2033-2045 (1984).
Am Soc for Testing and Materials, Designation: E1649-94, pp. 870-888 (1995).
Complaint.
Amended Complaint.
Answer of Defendants Massachusetts Institute of Tech. and the General Hospital Corporation to Amended Complaint and Amended Counter Claim.
Reply of Plaintiff, Ambuj D. Sagar, Ph.D., To Amended Counterclaim of Def. Massachusetts Institute of Technology and the General Hospital Corp.
Long Term Performance of Gamma Irradiated HDPE Cups in Total Hip Replacement (1997) (Abstract).
De Boer et al., Journal of Materials Science 19: 428-438 (1984).
De Boer et al., Crosslinking of High Molecular Weight Polyethylene, Proefschrift, Vrijdag 23 Maart, pp. 1-150 (1984).
Lue, Effects of Gamma Irradiation and Post Heat-Treatments on the Structure and Mechanical Properties of Ultra Hight Molecular Weight Polyethylene (UHMW-PE), pp. 1-138 (Abstract of Thesis Submitted in Partial Fulfillment of the Requirements for the Degree of Master of Science in Plastics, University of Lowell, Jun. 1979).
Römpp Chemie Lexikon 3760-3766 (German), 1992.
Römpp Chemie Lexikon 3760-3766 (English translation), 1992.
Encyclopedia of Material Technology 776-785 (German), 1993.
Encyclopedia of Material Technology 776-785 (English translation), 1993.
Bhateja et al., Polymer Journal 21(9): 739-750 (1989).
Bhateja et al., J. Macromol. Sci.—Phys. B29(1): 1-10 (1990).
Bhateja et al., J.M.S.—Rev. Macromol. Chem. Phys. C35(4): 581-659 (1995).
Hsieh et al., Journal of Applied Polymer Science 53(3): 347-354 (2003) (Abstract).
Jones et al., Wear 70: 77-92 (1981).
Kanig, Colloid & Polymer Sci. 260: 356-377 (1982) (German).
Kanig, Colloid & Polymer Sci. 260: 356-377 (1982) (English translation).
Lue, Effects of Gamma Irradiation and Post Heat-Treatments on the Structure and Mechanical Properties of Ultra High Molecular Weight Polyethylene (UHMW-PE), 1979.
Sakai et al., Polymer 34(16): 3362-3367 (1993).
Sun et al., Polymer Engineering and Science 29(21): 1503-1510 (2004) (Abstract).
Wang et al., Journal of Applied Polymer Science 34: 593-599 (1987).
Witkiewicz et al., Journal of Biomedical Materials Research 33(2): 73-82 (1998) (Abstract).
The Journal of Bone & Joint Surgery 88-A(2): 68-74 & 78 (Feb. 2006).
Akay et al., Radiat. Phys. Chem. 36(3): 337-343 (1990).
Allen et al., Polymer Degradation & Stability 19: 77-95 (1987).
Allen et al., Applied Organometallic Chemistry 1: 311-317 (1987).
Allen et al., Polymer Degradation and Stabililty 39: 293-297 (1993).
Allen et al., J. of Chromatography 629: 283-290 (1993).
Allen et al., Chemistry & Industry, pp. 16-17 (1990).
Allen et al., The Effects of Ionising Radiation of Additives Present in Food-contact Polymers, Food Irradiation & the Chemist, pp. 124-139 (1990).
Allen et al., Chemistry & Industry, pp. 198-199 (1987).
Allen et al., Chemistry & Industry, pp. 854-855 (1987).

(56) References Cited

OTHER PUBLICATIONS

Allen et al., Radiat. Phys. Chem. 38(5): 461-465 (1991).
Allen et al., Food Additives & Contaminants 5(1): 433-435 (1988).
Allen et al., Chemistry & Industry, pp. 399-400 (1988).
Allen et al., Chemistry & Industry, pp. 38-39 (1989).
Alexander et al., J. Poly. Sci. XXII(101): 343-348 (1956).
Amstutz, Orthopedic Clinics of North America 4(2): 235-248 (1973).
Amstutz, Implant Wear: The Future of Total Joint Replacement, pp. 1-27, Symposium, Oakbrook, IL (Sep. 1995).
Amstutz, J. Biomed. Mater. Res. 3: 547-568 (1968).
Amstutz et al., J. Biomed. Mater. Res. 10: 25-31 (1976).
Artandi, Radiat. Phys. Chem. 9: 183-191 (1977).
Atkinson et al., Transactions of the ASME 100: 208-218 (1978).
Azuma et al., Agric. Biol. Chem. 48(8): 2003-2008 (1984).
Azuma et al., Agric. Biol. Chem. 47(4): 855-860 (1983).
Baker et al., Study of fatigue resistance of chemical and radiation crosslinked medical grade ultrahigh molecular weight polyethylene, pp. 573-581, John Wiley & Sons, Inc. (1999).
Baker et al., Polymer 41: 795-808 (2000).
Bakker, The Wiley Encyclopedia of Packaging Technology, pp. 530, 562 & 564 (1986).
Bankston, et al., Clinical Orthopaedics and Related Research 317: 7-13 (1995).
Bargmann et al., Clinical Orthopaedics and Related Research 369: 49-58 (1999).
Barrett, Int. J. Appl. Radiat. Isot. 33: 1177-1187 (1982).
Bartel, J. Bone & Joint Surgery 68-A(7): 1041-1051 (1986).
Bartel, The Effect of Metal Backing on Stresses in Polyethylene Acetabular Components, pp. 229-239 (1983).
Barton et al., Comparative Wear Under Three Different Tribological Conditions of Acetabular Crosslinked Ultra High Molecular Weight Polyethylene, 44th Annual Meeting, Orthopaedic Research Society, Mar. 16-19, 1998, New Orleans, Louisiana.
Basheer, Journal of Polymer Science: Polymer Physics Edition 21: 949-956 (1983).
Baskett, Nature 174: 364-365 (1954).
Bayley et al., J. of Bone & Joint Surgery 70-A(5): 668-674 (1988).
Bechenbaugh et al., J. of Bone & Joint Surgery 60-A(3): 306-313 (1978).
Beenen et al., Radiat. Phys. Chem. 35(1-3 ): 364-368 (1990).
Bell et al., J. of Bone & Joint Surgery 67-A(8): 1165-1175 (1985).
Bellare et al., Biomaterials 17(24): 2325-2333 (1996).
Bellare et al., The Polyethylene History, pp. 45-50.
Bennett et al., Global Reference UHMWPE: Characterization & Comparison to Commercial UHMWPE, $42^{nd}$ Annual Meeting, Orthopedic Research Society, Atlanta, Georgia, p. 472 (1996).
Berry et al., The Use of Ultrahigh Molecular Weight Polyethylene in Articular Prosthesis—I Polymer characterization of Six "Off the Shelf" Acetabular Components, ORPL (1984).
Bhambri et al., A Comparison of Morphology of Hip Simulator and Pin-On-Flat Wear Particles of Highly Crosslinked Polyethylene, 1999 Society of Biomaterials, 25th Annual Meeting Transactions, p. 505.
Bhateja, Polymer 23: 654-655 (1982).
Bhateja, Journal of Applied Polymer Science 28: 861-872 (1983).
Bhateja, Journal of Polymer Science: Polymer Physics Edition, vol. 21, 523-536 (1983).
Bhateja, Polymer 22: 23-28 (1981).
Bhateja et al., Polymer Engineering and Science, Nov. 23 (16): 888-894 (1983).
Biedermann et al., Journal of Chromatography A(764): 65-71 (1997).
Billmeyer, Jr. et al., Textbook of Polymer Science, $3^{rd}$ Edition, pp. 312-314 (1984).
Birkinshaw et al., Materials Chemistry & Physics 14: 549-558 (1986).
Birkinshaw et al., Polymer Communications 28: 286-288 (1987).
Birkinshaw et al., Polymer Degradation & Stability 22: 285-294 (1988).
Birkinshaw et al., J. Applied Polymer Science 38: 1967-1973 (1989).
Black, Orthopaedic Biomaterials in Research and Practice, pp. 144-150 (1988).
Black et al., J. of Chromatography 637: 71-80 (1993).
Blackadder et al., Polymer 11(2): 147-164 (1970).
Blackadder et al., Polymer 13: 584-586 (1972).
Blunn et al., Clinical Orthopedics & Related Research 273: 253-260 (1991).
Blunn et al., J. Bone & Joint Surgery 84-B(7): 946-949 (2002).
Booth, Industrial Sterilization Technologies: New and Old Trends Shape Manufacturer Choices, Medical Device & Diagnostic Industry, pp. 64-72 (1995).
Bosboom, et al., Journal of Chromatography A(723): 384-391 (1996).
Bostrom et al., Degradation in Polyethyelene as a Result of Sterilization, Shelf Storage, and In Vivo Use, $40^{th}$ Annual Meeting, Orthopaedic Research Society, New Orleans, LA, p. 288 (1994).
Bourges et al., Packaging Technology & Science 5: 205-209 (1992).
Bourges et al., Packaging Technology and Science 5: 197-204 (1992).
Bourges et al., Food Additives and Contaminants 10(4): 443-452 (1993).
Boyd et al., J. Agric. Food Chem. 39: 789-792 (1991).
Bragdon et al., A New Polyethylene with Undetectable Wear at 12 Million Cycles, $24^{th}$ Annual Meeting of the Society for Biomaterials, San Diego, CA p. 2. (1998).
Brinston, Radiat. Phys. Chem. 35(1-3): 390-392, (1990).
Brinston, Gaining the Competitive Edge with Gamma Sterilization, Medical Device Technology, pp. 28-33 (1991).
Brinston et al., Converting to Gamma-Radiation Sterilization: An Overview for Medical Device Manufacturers, Medical Device Technology, pp. 18-22 (1993).
Brown et al., Wear 40: 255-264 (1976).
Buchalla et al., Die Stahlensterilisation von Medikalprodukten aus Kunstoffen—eine Ubersicht, Teil II, Bundesgesundhbl., pp. 298-304 (Jul. 1994).
Buchalla et al., Die Strahlensterilisation von Medikalprodukten aus Kunstoffen—eine Ubersicht, Teil II, Bundesgesundhbl., pp. 347-353 (Aug. 1994).
Buchalla et al., Die Strahlensterilisation von Medikalprodukten aus Kunststoffen-eine Ubersicht, Teil I, Bundesgesundhbl., pp. 261-268 (Jun. 1994).
Buchalla et al., Journal of Food Protection 56(11): 991-997 (1993).
Buchalla et al., Radiat. Phys. Chem. 46(4-6): 579-585 (1995).
Bureiko et al., Headspace Analysis of Volatile Impurities in Solid Polymers, pp. 330-336 (translated from Zhurnal Analiticheskoi Khimii 46(3): 452-460 (1991)).
Burstein, Biomechanics of the Knee, pp. 21-39.
Callaghn, et al., Clinical Orthopaedics and Related Research 317: 14-18 (1995).
Cameron et al., Clinical Orthopaedics and Related Research 165: 197-199 (1982).
Cameron et al., Orthopaedic Review XVI(3): 75-77 (1987).
Camino, TRIP 4(7): 246 (1996).
Caputo et al., Sterilization with Ethylene Oxide & Other Gases, Chemical & Physical Sterilization, pp. 47-64.
Carlsson et al., Polypropylene Degradation by γ-Irradiation in Air, Polymer Stabilization and Degradation, pp. 359-371 (1985).
Cates et al., J. Bones & Joint Surgery 75-B(2): 249-253 (1993).
Champion, Fatigue Crack Growth Behavior of Enhanced Ultra-High Molecular Weight Polyethyelen, $20^{th}$ Annual Meeting of the Society for Biomaterials, Boston, MA, p. 76 (1994).
Chapiro, Radiation Chemistry of Polymeric Systems, Interscience Publishers, John Wiley & Sons, New York, p. 385-494 (1962).
Chapiro, Technical Development and Prospects of Sterilization by Ionizing Radiation, Physical & Chemical Effects of Ionizing Radiations on Polymeric Systems, pp. 367-374 (1974).
Charlesby, Proceedings of the Royal Society of London 215, 188-214 (1952).
Charlesby, Advances in Chemistry Series 66: 1-21 (1974).
Charlesby, Radiat. Phys. Chem. 37(1): 5-10 (1991).
Charlesby, Atomic Radiation and Polymers, Polyethylene, pp. 198-257 (1960).

(56) References Cited

OTHER PUBLICATIONS

Charlesby et al., Analysis of the solubility behavior of irradiated polyethylene and other polymers, pp. 367-386 (1958).
Charnley, J. of Bone & Joint Surgery 54B(1): 61-76 (1972).
Charnley et al., Clinical Orthopaedics and Related Research 95: 9-25 (1973).
Charnely, et al., Med. & Biol. Engng. 7: 31-39 (1969).
Chen et al, Journal of Polymer Science 27(12): 4051-4075 (1989).
Chiesa et al., Sterilization Effects on highly crosslinked UHMWPE, 1999 Society for Biomaterials, 25th Annual Meeting Transactions (1999).
Chillag, et al., Clinical Orthopaedics & Related Research 273: pp. 261-263 (1991).
Chin, Gamma Sterilization and Single-Use Devices, pp. 21-23.
Chuaqui-Offermanns, Radiat. Phys. Chem. 34(6): 1005-1007 (1989).
Chuaqui-Offermanns, J. of Radiation Sterilization 1:29-41 (1992).
Clarke, Clinical Orthopaedics & Related Research 121: 126-142 (1976).
Clarke et al., Biomaterials 6: 184-188 (1985).
Clarke et al., Simulator Wear Study of High-Dose Gamma-Irradiated UHMWPE Cups, Abstracts of the 23rd Annual Meeting of the Society for Biomaterials(Apr. 1997).
Clayton et al., Clinical Orthopaedics & Related Research 170: 152-155 (1982).
Clegg et al., Irradiation Effects on Polymers, pp. 48-59, Elsevier Applied Science (1991).
Clough, Encyclopedia of Polymer Science and Engineering, vol. 13, Second Edition, pp. 667-708, John Wiley & Sons, New York (1988).
Clough et al., Radiation Resistance of Polymers and Composites, Chapter 3, pp. 79-156, Elsevier Applied Science, London (1991).
Clough, Radiation Effects on Polymers, American Chemical Society (1991).
Cohn, Jr. et al., Infections, Principles of Surgery/Basic considerations, pp. 181-215 (1986).
Collins et al., J. of Bone & Joint Surgery 64-A(6): 939-940 (1982).
Collier et al., Journal of Arthroplasty 11(4): 377-389 (1996).
Cook et al., The Effect of Molecular Weight on the Cross-Link Density of Irradiated Ultra-High Molecular Weight Polyethelenes, 24th Annual Meeting of the Society for Biomaterials, p. 153 (1998).
Costa et al., Biomaterials 19: 1371-1385 (1998).
Coughlin et al., Encyclopedia of Polymer Science and Engineering 6: 490-494 (1986).
Cracchiolo III et al., Clinical Orthopaedics & Related Research 145: 37-46 (1979).
Cracco et al., The Journal of Chemical Physics 37(10): 2449-2457 (1962).
Crowninshield et al., J. Biomechanics 11: 75-85 (1978).
Crugnola et al., Journal of Applied Polymer Science 20: 809-812 (1976).
Currier et al., Effect of Fabrication Method and Resin Type on Performance of Tibial Bearings, pp. 143-151, John Wiley & Sons, Inc. (2000).
Currier et al., Clinical Orthopaedics and Related Research 342: 111-122 (1997).
de Boer et al., Polymer Bulletin 7: 309-316 (1982).
de Boer et al., Polymer Bulletin 5: 317-324 (1981).
de Boer et al., Polymer 25: 513-519 (1984).
DeGante et al., Packaging Technology and Science 3: 97-115 (1990).
Delincee, Trends in Food Science & Technology 9: 73-82 (1998).
Demertzis et al., Packaging Technology and Science 12: 119-130 (1999).
Dempsey et al., J. Biomaterials Applications 3: 454-523 (1989).
Derbyshire, Radiat. Phys. Chem. 14: 333-342 (1979).
Derbyshire et al., Med. Eng. Phys. 16: 229-236 (1994).
Deschenes, et al., Radiat. Phys. Chem. 46( 4-6): 805-808 (1995).
Devane et al., Clinical Orthopaedics and Related Research 319: 317-326 (1995).
Devane et al., J. of Arthroplasty 12(3): 256-266 (1997).
Devane et al., J. of Bone and Joint Surgery 79-A(5): 682-689 (1997).

Dijkstra et al., Polymer Bulletin 20: 557-562 (1988).
Dimaio et al., Effect of Radiation Dose on the Physical Properties of Crosslinked UHMWPE, 45th Annual Meeting, Orthopedic research Society (1999).
Dole, Radiat. Phys. Chem. 22(1/2): 11-19 (1983).
Dole, Polym. Plast. Technol. Eng. 13(1): 41-64 (1979).
Dole et al., Radiat. Phys. Chem. 14 : 711-720 (1979).
Dole et al., Radiat.Phys. Chem. 9: 433-444 (1977).
Dole, The Radiation Chemistry of Macromolecules, vol. 1, chapters 1-2, 4-6, 11-14.
Dorr et al., Clinical Orthopaedics and Related Research 205: 5-11 (1986).
Dorpema, Radiat. Phys. Chem. 35(1-3): 357-360 (1980).
Dowling et al., J. of Bone and Joint Surgery 60-B(3): 375-382 (1978).
Ducheyne et al., J. of Bone and Joint Surgery 60-A(3): 384-391 (1978).
Dumbleton et al., J. of Applied Polymer Science 18: 3493-3496 (1974).
Dumbleton et al., Wear 29: 163-171 (1974).
Dumbleton et al., Wear 37: 279-289 (1976).
DuPlessis et al., Radiat. Phys. Chem. 9: 647-652 (1977).
Edidin et al., J. of Arthroplasty 14(5): 616-627 (1999).
Elbert et al., J. of Biomedical Materials Research 28: 181-187 (1994).
Ellis, Medical Markets for Radiation Sterilizable Plastics, pp. 31-34.
Ellis, Circle Reader Service #62, pp. 50-51 (1990).
Ergoz et al., Crystallization Kinetics of Linear Polyethylene 5(2): 147-157 (1972).
Ewald et al., American Academy of Orthopaedic Surgeons, p. 202.
Eyerer, Biomed Technik 28: 297-309 (1983).
Eyerer, Prop. Changes of UHMWPE Poly. During Implant.—First Hints for the Dev. of an Alt. Poly., ANTEC, Soc. of Plastic Engineers, 43rd Annual Technical Conference (1985).
Eyerer, J. Biomedical Materials Research 18: 1137-1151 (1984).
Eyerer et al., Ultrahochmolekulares Polyethylen Fur Gelenkendoprothesen, Kunststoffe 77(6): 617-622 (1987).
Farling et al., Mechanical Properties of Biomaterials, pp. 53-64 (1980).
Feazel et al., Package Engineering 5(4): 43-45 (1960).
Ferris, J. Exp. Path. 71: 367-373 (1990).
Figgie III, et al., J. of Bone and Joint Surgery 68-A(7): 1035-1040 (1986).
Fisher, Journal of Artroplasty 10(5): 1995.
Francis et al., The Velocity of Oxidation of Paraffin Wax, Parts I-IV, pp. 381-393 (1923).
Francis et al., The Non-Acidic Oxidation Products of Paraffin Wax, pp. 2377-2834 (1926).
Freeman et al., Clinical Orthopaedics and Related Research 192: 46-58 (1985).
Frohnsdorff, Radiat. Phys. Chem. 17: 95-106 (1981).
Fujita, Organic Vapors above the Glass Transition Temperature, Diffusion in Polymers, pp. 75-105 (1968).
Furuhashi et al., Bull. Tokyo Med. Dent. Univ. 29: 23-35 (1982).
Galante et al., Acta Orthopaedica Scandinavica, Supplementum No. 145: 1-46 (1973).
Galante et al., Wear Rates of Candidate Materials for total Hip Arthroplasty, Proceedings of the first open scientific meeting of The Hip Society, pp. 67-78 (1973).
Gibbons et al., Wear & Degradation of Retrieved Ultrahigh Molecular Weight Polyethylene and Other Polymeric Implants, American Society for Testing and Materials, pp. 20-40 (1979).
Giberson, Oxygen Diffusion & Reaction During •-Irradiation of Polyethylene 66: 463-468 (1962).
Gielenz et al., Colloid & Polymer Sci. 250:742-753 (1982).
Gilbert et al., J. Association of Public Analysis 19: 39-49 (1981).
Gilbert et al., J. Sci. Food Agric. 34: 647-652 (1983).
Gilburt et al., JFSS 31(3): 337-347 (1991).
Gillen et al., Polymer Degradation and Stability 47: 149-161 (1995).
Gillis et al., An Ind. Eval. of the Mech. Chem. and Fracture Properties of UHMWPE Cross Linked by 34 Different Conditions, 45th Annual Meeting, Orthopaedic Research Society (1999).
Goldman et al., Polymer 37(14): 2909-2913 (1996).

(56) References Cited

OTHER PUBLICATIONS

Goldman et al., Characterization of Structure and Fatigue Resistance of Aged and Irradiated UHMWPE, The 21$^{st}$ Annual Meeting of the Society for Biomaterials, San Francisco, CA (1995).
Goldman et al., J. Biomed. Mater. Res. 40: 378-384 (1998).
Goodacre et al., Nature 359: 594 (1992).
Grewel et al., Electrochemical Machining of Orthopaedic Components, Advances in Manufacturing Technology, pp. 366-373 (1984).
Grob, Jr. et al., Journal of Chromatography 156: 1-20 (1978).
Grob et al., Journal of Chromatography 219: 13-20 (1981).
Grob et al., Journal of Chromatography A(750): 11-23 (1996).
Grobbelaar et al., The Journal of Bone and Joint Surgery 60-B(3): 370-374 (1978).
Grobbelaar et al., The Role of Radiation in Orthopaedic Implants, pp. 10-13.
Grood et al., The Journal of Bone and Joint Surgery 58-A(8):1083-1088 (1976).
Grünewald et al., Untersuchung der Einwirkung Ionisisender Strahlung auf die Gseund Wasserdampf-Durchlassigkeit von Verpackungs-Folien, Fette Seifen Anstrichmittel 63(10): 928-934 (1961).
Gsell et al., Quality Indicators of High-Performance UHMWPE, Zimmer Publication (1997).
Gustilo et al., Quadriceps and Patellar Tendon Ruptures following Total Knee Arthroplasty, pp. 41-47, (1984).
Gvozdic et al., Crosslinking and Crystallinity in Irradiated Polyethylene, Polymer Preprints 19(1): 584-587 (1978).
Gvozdic et al., J. Phys. Chem. 85(11): 1563-1569 (1981).
Haas et al., Crystallinity in Implanted UHMW Polyetheylene, 25$^{th}$ Annual ORS, San Francisco, CA, p. 263 (1979).
Haesen et al., J. Indust. Irradiation Tech. 1(3): 259-280 (1983).
Hagman et al., J. of Chromatography 395: 271-279 (1987).
Hagman et al., J. of High Resolution Chromatography & Chromatography Communications 11: 830-836 (1988).
Hagman et al., Anal. Chem. 61: 1202-1207 (1989).
Hagman et al., J. Microcol. Sep. 5(4): 341-346 (1993).
Hagman et al., J. of High Resolution Chromatography & Chromatography Communications 11: 46-50 (1988).
Haire et al., Food Research International 30(3/4): 249-264 (1997).
Halcomb et al., Trans Am Soc Artif Intern Organs, vol. XXVII: 364-381 (1981).
Hall et al., Med. Eng. Phys. 19(8): 711-719 (1997).
Halldin et al., The Effect of Particle Characterics on the Sintering Behavior of Ultra-High Molecular Weight Poly., Dept. of Mech. Eng., Univ. of Wisc.—Madison, WI, 53706, pp. 238-241 (1983).
Halley et al., Polymer 35(10): 2186-2191 (1994).
Hamilton et al., The Effect of Packaging on the Stability of Gamma Sterilized UHMWPE, 44$^{th}$ Annual Meeting, Orthopaedic Research Society, New Orlean, LA (1998).
Hamilton et al., The Effect of Fusion Defects on Mechanical Properties of UHMWPE, Fifth World Biomaterials Congress, Toronto, Canada (1996).
Hamilton-Kemp et al., Volatile Compounds from Strawberry Foilage & Flowers, American Chemical Society, pp. 229-239 (1993).
Handlos et al., Journal of Applied Polymer Science 20: 3375-3386 (1976).
Handlos, Radiat. Phys. Chem. 18(1-2): 175-182 (1981).
Hankemeier et al., Journal of Chromatography A(732): 75-84 (1996).
Hanna, Industrial Problem Solving with UHMW Polyolefins, Hercules, Inc., pp. 1-9 (1982).
Harris, Clinical Orthopaedics and Related Research 274: 6-11 (1992).
Harris, Clinical Orthopaedics and Related Research 311: 46-53 (1995).
Haslam et al., Industrial and Engineering Chemistry 19(2): 292-296 (1927).
Hastings et al., Knee Wear Testing of a Radiation Crosslinked and Remelted UHMWPE, 25$^{th}$ Annual Meeting Transactions, Soc. for Biomaterials, p. 328 (1999).
Hegazy et al., J. of Applied Polymer Science 26: 2947-2957 (1981).
Hegazy et al., J. of Applied Polymer Science, vol. 26, p. 1361 (1981).
Heinze, Das Verhalten von Hochpolymeren gegenüber energiereicher Strahlung*) Kolloid-Zeitschrift und Zeitschrift fur Polymere, Band 210, Heft 1, pp. 45-54 (1965).
Helmig, J. Chromatography A 732: 414-417 (1996).
Hempel et al., Bestimmung von monomeren flüchtigen Anteilen in Polystyrol und Styrol-Misch- und Pfropfpolymerisaten, Deutsche Lebensmittel-Rundschau. 84(8): 239-242 (1988).
Hernandez et al., J. of Bone and Joint Surgery 76-B(2): 263-266 (1994).
Herzog et al., Desorption von Äthylenoxid aus gassterilisierten Plasten und Elasten, Aus dem Institut für Allgemeine Hygiene, vol. 25(5): 386-389 (1979).
Hida et al., Journal of Chromatography A 761: 332-335 (1997).
Hikmet et al., Radiat. Phys. Chem. 29(4): 275-281 (1987).
Hikmet et al., Radiat. Phys. Chem. 29(1): 15-19 (1987).
Hill et al., Radiation Chemical Yields: G Values, pp. 387-397 (1989).
Hiller et al., J. of High Resolution Chromatography 16: 5-12 (1993).
Hodgson et al., J. Agric. Food Chem. 46: 1397-1405 (1998).
Hofmann et al., Design, Performance & Applicability of a Multi-Functional Thermal Desorption System for Trace Analysis in Capillary GC, Gerstel GmbH, pp. 1165-1175 (1992).
Hollifield, Food and Drug Administration Studies of High-Temperature Food Packaging, Food and Packaging Interactions, pp. 22-36 (1991).
Hornbogen, Mikrostruktur und Verchleiβ, pp. 79-103 (1977).
Hood et al., Contact Area & Pressure Dist. in Contemporary Total Knee Designs, Dept. of Biomech., The Hospital for Special Surgery, 535 East 70 Street, New York, NY 10021, pp. 233-236 (1983).
Hood et al., J. of Biomedical Materials Research 17: 829-842 (1983).
Hood et al., Retrieval Analysis of Fifty-Seven Total Condylar Knee Prostheses, 27$^{th}$ Annual ORS, p. 159, Las Vegas, NV (1981).
Hopson et al., Orthopedics 3(6): 537-546 (1980).
Horng et al., Plastics Engineering, pp. 35-37 (1984).
Housel, Plastics Engineering, pp. 47-49 (1985).
Hsu et al., Clinical Orthopaedics and Related Research 246: 260-265 (1989).
Hubbard, The Effect of Processing and Material on the Swell Ratio of UHMWPE, NTH/MED-DEV-3-98 6.1.98.
Hubbard, Improvements in Oxidation Resistance in Medical Grade UHMWPE, NTH/MED-DEV-2-98 6.1.98.
Hudis, Journal of Applied Polymer Science 16: 2397-2415 (1972).
Ikokwu et al., The Use of Ultrahigh Molecular Weight Polyethylene in Particular Prosthesis—IV. Environ. Stress Cracking Propensity of Polyethylene in Bovine Serum, pp. 366-371 (1977).
Imai et al., Journal of Polymer Science, Part A: Polymer Chemistry 27: 1763-1773 (1989).
Insall et al., The Journal of Bone and Joint Surgery 64-A( 9): 1317-1323 (1982).
Insall et al., Clinical Orthopedics & Related Research 192: 13-22 (1985).
Iring et al., Polymer Bulletin: 7: 489-495 (1982).
Jackson et al., The American Journal of Sports Medicine 18(1): 1-11 (1990).
Jacobs et al., J. Biomed. Matter Res. Symposium 6: 221-225 (1975).
Jacobsson, Journal of High Resolution Chromatography & Chromatography Communications 7: 185-190 (1984).
Jaeger, Moving Sources of Hear and the Temperature at Sliding Contacts, pp. 203-224 (1942).
Jahan et al., Journal of Biomedical Materials Research 25:1005-1017 (1991).
Jahan et al., Journal of Luminescence 40 & 41: 242-243 (1988).
James et al., J Biomed Matter Res (Appl Biomater) 48:374-384 (1999).
Jasty et al., The Journal of Bone and Joint Surgery 79-A(3) 349-358 (1997).
Jones et al., Wear 70:77-92 (1981).
Jones et al., Journal of Polymer Science: Part B: Polymer Physics 31: 807-819 (1993).
Kabo et al., The Journal of Bone and Joint Surgery 75-B(2): 254-258 (1993).

(56) References Cited

OTHER PUBLICATIONS

Kaltwasswer et al., The Patello-Femoral Joint in Total Knee Replacement, 33$^{rd}$ Annual Meeting, Orthopaedic Research Society, Jan. 19-22, 1987, San Francisco, CA.
Kang et al., Journal of the American Chemical Society 89(9): 1980-1986 (1967).
Kang et al., Journal of the American Chemical Society 89:9 (1967).
Kang et al., Polymer Preprints, American Chemical Society, Division of Polymer Chemisty 8(1): 582-587 (1967).
Kärkkäinen et al., Journal of Forensic Sciences 39(1): 186-193 (1994).
Kashiwabara, Radiat. Phys. Chem. 32(2): 203-208 (1988).
Kashiwabara et al., Radiat. Phys. Chem. 37(1): 43-46 (1991).
Kashiwabara et al., Radiation-Induced Oxidation of Plastics, Radiation Processing of Polymers, Chapter 11, pp. 221-254 (1992).
Kavanagh et al., The Journal of Bone and Joint Surgery 71-A(10): 1496-1503 (1989).
Keay, J. Fd Technol. 3: 123-129 (1968).
Kilcast, Irradiation of Packaged food, Food Irradiation and the Chemist, pp. 140-152 (1990).
Kiloran, Radiation Res. Rev. 3 pp. 369-388 (1972).
Kim-Kang et al., Applied Spectroscopy 45(4): 572-580 (1991).
Kim-Kang et al., Packaging Technology and Science 4: 35-48 (1991).
King et al., The Residual Free Effect on Aging of Crosslinked Ultra-High Molecular Weight Polyethylene, 25$^{th}$ Annual Meeting Transactions, Society for Biomaterials (1999).
Kitamaru et al., Journal of the American Chemical Society 86: 3529-3534 (1964).
Klarenbeek et al., Viricidal Actions of Ethylene Oxide Gas, pp. 525-528 (1954).
Klaassen, Nonmetallic Environmental Toxicants: Air Pollutants, Solvents & Vapors & Pesticides, Chapter 70, pp. 1628-1650 (1985).
Klaassen, Principles of Toxicology, Section XVII, Chapter 68, pp. 1592-1604, (1985).
Knyazev et al., Irradiated Polyethylene in Technology, "KHIMIYA" Publishing House (1974).
Kolb et al., Chromatographia 10(12): 705-711 (1977).
Kolb et al., Multiple Headspace Extraction—A Procedure for Quantitative Analysis of Volatile Compounds in Solid Samples and Its Application for the Analysis of Vinyl Chloride Monomer (VCM) and Water in a PVC Resin, pp. 2-32.
Kolb et al., Journal of Chromatography 204: 371-376 (1981).
Kolb et al., Quantitative Bestimmung Von Restlösemittein in Bedruckten Verpackungsfolien Nach Dem Verfahren Der Mehrfach-Gasextraktion, pp. 3-37 (1981).
Koszinowski et al., Deutsche Lebensmittel-Rundschau Zeitschrift fur Lebensmittelkunde and Lebensmittelrecht, Deutsche Lebensmittel-Rundschau 79(5): 179-183 (1983).
Kretzschmar, Ethylenoxid-Desorption aus sterilisierten Kunststoff- und Gummimateriallen, Ethylene Oxide Desorption from Sterilized Plastic and Rubber Materials, Hyg. + Med. 12: 542-546 (1987).
Kurth et al., Effects of Radiation Sterilization on UHMW-Polyethylene, The Third World Biomaterials Congress, Kyoto, Japan (Apr. 1988).
Kurtz et al., Post-Irradiation Aging and the Stresses in UHMWPE Components for Total Joint Replacement, 40th Annual Meeting, Orthopaedics Research Society, New Orlean, LA (Feb. 1994).
Kurtz et al., Biomaterials 20: 1449-1462 (1999).
Kurtz et al., Biomaterials 20: 1659-1688 (1999).
LaBorde et al., Toxicology and Applied Pharmacology 56: 16-22 (1980).
Lacoste et al., Gamma-Photo-and Thermally-Initiated Oxidation of Polyolefines Used in Packaging 15(12): 139-152 (Jun. 1995).
Lafortune et al., Three-Dimensional Kinematics of the Patella During Walking, pp. 337-341.
Lancaster, Tribology, pp. 82-86 (1971).
Landfield et al., Sterilization of Medical Devices based on Polymer Selection & Stabilization Techniques, Chapter 43, pp. 975-999 (1983).
Langlais et al., International Orthopaedics 4: 145-153 (1980).
Lantos, Journal of Biomaterials Applications 2: 358-371 (1988).
Lanza, Irradiation—Properties Changes, Crystalline Olefin Polymers 2(7): 301-360 (1964).
Larsen et ak, Industrial & Engineering Chemistry 34(2): 184-193 (1942).
Lattimer et al., Determination of residual volatile chemicals in polymers by solid headspace gas chromatography, pp. 80-88 (1980).
Lawton et al., Journal of Polymer Science 32: 257-277 (1958).
Leemhorst, Industrial Application of the Gamma Sterilization Process, Gammaster BV, pp. 1-8 (1980).
Leininger et al., Change in Properties of Plastics During Implantation, vol. X Trans. Amer. Soc. Artif. Int. Organs, pp. 320-321 (1964).
Levai et al., The Journal of Bone and Joint Surgery 65-B(4): 448-451 (1983).
Lewis et al., Clinical Orthopaedics and Related Research 299: 11-17 (1994).
Lewis, The Journal of Bone and Joint Surgery 82-A(2): 281-287 (2000).
Lewis, J. Biomed. Mater. Res. (Appl. Biomater) 38: 55-75 (1997).
Ley, J. Soc. Cosmet. Chem. 27: 482-489 (1976).
Ley, Radiation Sterilization—Microbiological Aspects, Irradiated Products Limited, pp. 1-16 (1984).
Li et al., The Journal of Bone and Joint Surgery 76-A(7): 1080-1090 (1994).
Ligon et al., Analytical Chemistry 48(3): 491-484 (1976).
Livermore et al., The Journal of Bone and Joint Surgery 72-A(4): 518-528 (1990).
Livingston et al., The Journal of Bone and Joint Surgery 79-A(10): 1529-1538 (1997).
Lombardi et al., The Journal of Bone and Joint Surgery 78-A(5): 675-679 (1988).
Loy, Journal of Polymer Science XLIV: 341-347, (1960).
Lue et al., ANTEC '84, Plastics in a World Economy, Conference Proceedings, New Orleans (1984), pp. 538-541.
Lue et al., Effects of Gamma-Irradiation on Ultra-High Molecular-Weight Polyethylene, ANTEC '81, pp. 246-247 (1981).
Lue, Effects of Gamma Irradiation and Post Heat-Treatments on the Structure and Mechanical Properties of Ultra High Molecular Weight Polyethylene (UHMW-PE), Thesis (1979).
Lyarsky et al., Journal of Hygiene, Epidemiology, Microbiology and Immunology 32(3): 257-264 (1988).
Lyons, Journal of Polymer Science: Part A(3): 777-791, (1965).
Makhlis, Radiation Physics and Chemistry of Polymers, Chapter III, p. 120-176, John Wiley & Sons, New York (1975).
Malek et al., Orthopaedic Review VII(6): 67-73 (1979).
Manley et al., Clinical Orthopaedics and Related Research 298: 137-146 (1994).
Marque et al., J Chim Phys 91: 1890-1895 (1994).
Masuda et al., Oxidation of Crosslinked Polyethylene for Surgical Implantation, Report of the Consultants' Meeting on Post-Irradiation Stability of Radiation Sterilized Medical Implants, International Atomic Energy Agency, Aug. 29-Sep. 1, 2000.
Mathews et al., The Inactivation of Certain Animal Viruses by Ethylene Oxide, Carbide & Carbon Chemicals Corporation, New York, NY, pp. 452-461 (1953).
Matsuo et al., Macromolecules19970; 2028-2035 (1986).
McIntyre et al., Development of High Sensitivity Techniques for Characterizing Outgassing of Polymeric Construction Materials for Microenvironments, Proceedings-Institute of Environmental.
McKellop et al., Clinical Orthopaedics and Related Research 369: 73-82 (1999).
McKellop et al., Increased Wear of UHMW Polyethylene After Gamma Radiation Sterilization, 26$^{th}$ Annual ORS, p. 99, Altanta, GA (1980).
McKellop et al., Journal of Biomedical Materials Research 12: 895-927 (1978).
McKellop et al., Journal of Orthopaedic Research 17:157-167 (1999).
McKellop et al., Journal of Orthopedic Research 17: 329-339 (1999).
McLain et al., The Journal of Arthroplasty 1(2): 91-98 (1986).
McLaren et al., Wear 8: pp. 3-7 (1965).
McLaughlin, Radiat. Phys. Chem. 21(4): 359-366 (1983).

(56) References Cited

OTHER PUBLICATIONS

Merkow et al., The Journal of Bone and Joint Surgery 67-A(9): 1321-1327 (1985).
Michael et al., Journal of Food Science 35: 631-634 (1970).
Miller et al., Wear 28: 207-216 (1974).
Minkoya et al., Colloid Polymer Science 268(11): 1018-1023 (1990).
Minakawa et al., The Journal of Bone and Joint Surgery 80-B(5): 894-899 (1998).
Mirra et al., Clinical Orthopaedics and Related Research 117: 221-240 (1976).
Mitsui et al., Polymer Journal 4(1): 79-86 (1973).
Miyaji et al., Polymer 22: 701-703 (1981).
Mol et al., Journal of Chromatography A, 703: 277-307 (1995).
Morales et al., Journal of Chromatography A, 66: 455-462 (1994).
Morrison, J. Biomechanics 3: 51-61 (1970).
Munari et al., J. of Microcolumn Separations 7(4):403-409 (1995).
Muratoglu et al., The Journal of Arthroplasty 16(2): 149-160 (2001).
Muratoglu et al., The Effect of Peroxide Content on the Cross-Link Density, Mechanical Properties and Wear Behavior of UHMWPE, 44th Annual Meeting, Orthopaedic Research Society (1998).
Muratoglu et al., Biomaterials 20: 1463-1470 (1999).
Murch et al., The Search for Low-Smoke Polyurethane Foams Goes on, Plastics Engineering, pp. 35-36 (1983).
Murray, Clinical Orthopaedics and Related Research 192: 59-68 (1985).
Narkis et al., J. Macromol. Science—Phys. B26(1): 37-58 (1987).
Nusbaum et al., Journal of Biomedical Materials Research 13: 557-576 (1979).
Nusbaum et al., Journal of Applied Polymer Science 23: 777-789 (1979).
Oberholzer et al., Sulzer Technical Review, 3/99, pp. 22-23 (1999).
O'Connor et al., Wear and High Cycle Fatigue of a Highly Crosslinked UHMWPE, 1999 Society for Biomaterials, 25th Annual Meeting Transactions, pp. 508 (1999(.
O'Donnell et al., Radiat. Phys. Chem. 39(2): 209-214 (1992).
Okada et al., Journal of Polymer Science L(153): S22-S24 (1961).
O'Neill et al., Polymer Degradation and Stability 63: 31-39 (1999).
Oonishi et al., Encyclopedic Handbook of Biomaterials and Bioengineering 2:1853-1868 (1995).
Oonishi et al., Radia. Phys. Chem 39(6): 495-504 (1992).
Oonishi et al., In-Vivo and In-Vitro Wear Behavior of Alumina Ceramic and UHMW Polyethylene Implant Bearing Surfaces in Total Joint Prostheses, Dept. of Orthopedic Surgery & Osaka-Minami National Hospital, pp. 1-26.
Oonishi et al., Wear of Highly Cross-linked Polyethylene Cup with 100 Mrad and Less than 10 Mrad, H. Oonishi Memorial Joint Replacement Institute, Tominaga Hospital, Japan Medical Materials Corp., Loma Linda Univ., Medical Center.
Oonishi et al., Super Low Wear Cross-Linked UHMWPE by Heavy High-Dose Radiation, WPOA 2nd Congress of Hip Section, p. 61 (1996).
Oonishi et al., Wear Resistance of Gamma-Ray Irradiated U.H.M.W. Polyethylene Socket in Total Hip Prosthesis, The Third World Biomaterials Congress, Kyoto, Japan (1988).
Oonishi et al., Wear of High-Dose Gamma Irradiated Polyethylene in Total Joint Replacement—Long Term Radiological Evaluation, 44th Annual Meeting, Orthopaedic Society (1998).
Oonishi et al., The Effects of Gamma-Irradiation on Wear Resistance of Polyethylene Socket in Total Hip Prostheses, The 17th Annual Meeting of the Society for Biomaterials (1991).
Oonishi et al., The Journal of Arthroplasty 16(8/1): 129-133 (2001).
Oonishi et al., Journal of Long-Term Effects of Medical Implants 2(1): 37-47 (1992).
Oonishi et al., Wear Resistance of Gamma-Ray Irradiated U.H.M.W. Polyethylene Socket in Total Hip Prostheses-Wear Test and Long Term Clinical Results, MRS International Meeting on Advanced Materials, vol. 1, pp. 351-356 (1989).
Oonishi et al., Clinical Implant Materials, Advances in Biomaterials. 9: 379-384 (1990).
Oonishi et al., Physical and Chemical Characteristics of High-Dose Gamma Irradiated Sockets—Retrieval Study After Long Term Implantation, 45th Annual Meeting, Orthopaedic Research Society (1999).
Oonishi et al., Gamma-Irradiated Cross-Linked Polyethylene in Total Hip Replacements—Analysis of Retrieved Sockets After Long-Term Implantation, Journal of Biomedical Materials Research, pp. 167-171 (2001).
Oonishi et al., The Low Wear of Cross-linked Polyethylene Sockets in Total Hip Prostheses, Encyclopedia of Biomaterials and Bioengineering, Part A, vol. 2, p. 1853-1868 (1995).
Oonishi et al., Journal of Materials Science: Materials in Medicine 7: 753-763 (1996).
Oonishi et al., Journal of Materials Science: Materials in Medicine 8: 11-18 (1997).
Oppenheimer et al., Further Studies of Polymers as Carcinogenic Agents in Animals, Cancer Research, pp. 333-340 (1955).
Pearson, The 1993 Medical Device Technology Raw Materials Survey, Medical Device Technology, pp. 42-46 (1993).
Pargas, Threshold of Regulation is "sensible" option for meat irradiation packaging, FDA's Hansen tesil AMI seminar, Foof Chemical News, pp. 9-11(1998).
Pascaud et al., Journal of Biomedical Materials Research 32: 619-626 (1996).
Patel et al., Journal of Polymer Science: Polymer Physics Edition 13: 303-321 (1975).
Patel et al., Polymer Letters Edition 11: 737-743 (1973).
Perkins et al., Polymer Engineering and Science 18(6): 527-532 (1978).
Pizzoferrato Biomat., Med. Dev., Art. Org. 7: 257-262 (1979).
Plester, Trans J. Plastics Inst., pp. 579-585 (1967).
Poggie et al., Effects of Resin Type, Consolidation Method, and Process Parameters on UHMWPE, ASTM Symposium: Characterization & Properties of Ultra-High Molecular Weight (1996).
Pokrop, Sterilization: Humidfication of Preconditioning Rooms in EtO Sterilization, Technology (1992).
Poolely et al., Proc. R. Soc. Lond. A., vol. 329: 251-274 (1972).
Premnath et al., Biomaterials 17(18 ): 1741-1753 (1996).
Premnath et al., Melt Irradiated UHMWPE for Total Hip Replacements: Synthesis and Properties, 43rd Annual Meeting, Orthopaedic Research Society (1997).
Pruitt et al., Compression Fatigue of Ultra High Molecular Weight Polyethylene and its implications for Total Joint Replacements, 39th Annual Meeting, Orthopaedic Research Society (1993).
Raffi, Trends in Analytical Chemistry 17(4): 226-233 (1998).
Rakita et al., Journal of Vinyl Technology 6(2): 73-76 (1984).
Ranawat, Clinical Orthopaedic and Related Research 205: 93-99 (1986).
Reckling et al., The Journal of Bone and Joint Surgery 57-A(1): 108-112 (1975).
Regan, Oxidative Degradation of UHMW Polyethylene Orthopaedic Implants, Honors Thesis from Curtin University of Technology, Australia (Nov. 1992).
Reilly et al., Acta orthop. Scandinav 43: 126-137 (1972).
Ricour et al., SPE Journal 28: 41-45 (1972).
Ries et al., The Journal of Arthroplasty 11(8): 974-976 (1996).
Ries et al., Abrasive Wear Simulation in Total Knee Arthroplasty, 45th Annual Meeting, Orthopaedic Research Society (1999).
Ries et al., Clinical Orthopaedic Related and Research 282: 164-169 (1992).
Riganakos et al., Radiation Physics and Chemistry 54: 527-540 (1999.
Rijke et al., Macromolecules 4(5): 594-599 (1971).
Ritter et al., The Journal of Bone and Joint Surgery 72-A(5): 672-677 (1990).
Rodriguez, Principles of Polymer Systems, Second Edition, pp. 216-218 (1982).
Roe et al., Journal of Biomedical Materials Research 15: 209-230 (1981).
Roffman et al., Clinical Orthopaedic and Related Research, No. 148: 112-116 (1980).

(56) References Cited

OTHER PUBLICATIONS

Rose, Determining Volatile Extractives from Micro Susceptor Food Packaging, Food and Packaging Interactions, Chapter 6, pp. 67-78 (1991).
Rose et al., Wear 51: 77-84 (1978).
Rose et al., The Effect of Ionizing Radiation on Ultra High Molecular Weight Polyethylene, 3$^{rd}$ Annual Meeting of the Society for Biomaterials (1997).
Rose et al., Clinical Orthopaedics and Related Research 145: pp. 277-286 (1979).
Rose et al., The Journal of Bone and Joint Surgery 62A(4): 537-549 (1980).
Rose et al., Journal of Orthopaedic Research 2(4): 393-400 (1984).
Rostoker et al., J. Biomed. Mater. 10: 303-310 (1976).
Rostoker et al., Journal of Biomedical Materials Research 13: 957-964 (1979).
Saegesser et al., Aktuelle Probleme in Chirugie and Orthopädie, Finding on total hip replacement for ten years, pp. 1-22 (1982).
Saikko, Acta Orthop Scand 66(6): 501-506 (1995).
Saikko et al., Wear Simulation of UHMWPE for total hip replacement with a multidirectional motion pin-on-disk device: Effects of counterface material, contact area, and lubricant, pp. 147-154 (1999).
Saki et al., Polymer 34(16): 3362-3367 (1993).
Salovey et al., Irradiation of Ultra High Molecular Weight Polyethylene, Polymer Reprints, pp. 118-119 (1985).
Salvati et al., J. of Bone & Joint Surgery 61-A(8): 1239-1242 (1979).
Sanford et al., Accelerated Oxidative Ageing Testing of UhHMWPE, 41st Annual Meeting, Orthopaedic Research Society (1995).
Sangster et al., Journal of Applied Polymer Science 42: 1385-1393 (1991).
Sauer et al., Polymer Engineering and Science 17(4): 246-250 (1977).
Saum, Oxidation vs. Depth and Time for Polyethylene Gamma Sterilized in Air, 40$^{th}$ Annual Meeting, Orthopaedic ResearchSociety (1994).
Saunders et al., Radiation Effects on Microorganisms and Polymers for Medical Products, Medical Device & Diagnostic Industry, pp. 89-92 (1993).
Savan, The Sterilizing Action of Gaseous Ethylene Oxide on Foot-and-Mouth Disease Virus, Am. J. Vet. Res., pp. 158-159 (1955).
Sawatari et al., Colloid & Polymer Science 226(4): 316-323 (1988).
Schaudy, Oxidation Processes in the Radiation-induces Cross-linking of Low Density Polyethylene, Kunststoffe 68(3): 22-25 (1978).
Schmalzried et al., The Journal of Bone and Joint Surgery 76-A(5): 677-688 (1994).
Schmalzried et al., The Journal Bone & Joint Surgery 74-A(6): 849-863 (1992).
Schmidt et al., The Effects of Calcium Stearate of the Properties of UHMWPE, 42nd Annual Meeting, Orthopedics Research Society (1996).
Schmidt et al., Journal of High Resolution Chromography & Chromatography Communications 11: 242-247 (1988).
Schnabel, Linear-Energy-Transfer Effects on Polymers, Radiation Effects on Polymers, pp. 44-52 (1991).
Schonhorn et al., Journal of Applied Polymer Science 18: 235-243 (1974).
Schreiber et al., Int. J. Riadia, Biol. 63(1): 105-130 (1993).
Schulzki, Radiat. Phys. Chem. 46(4-6): 765-769 (1995).
Schulzki et al., J. Agric. Food Chem. 43: 372-376 (1995).
Schulzki et al., J. Agric. Food Chem. 45: 3921-3927 (1997).
Schulzki et al., Irradiation Detection in Complex Lipid Matrices by Means of On-Line Coupled (LC-)LC-GC, Detection Methods for Irradiated Food: Current Status, pp. 259-268 (1996).
Scott, Orthopedic Clinics of No. America 10(1): 129-137 (1979).
Seedhom et al., Knee forces during the activity of getting out of a chair with and without the aid of arms, Biomedical Engineering, pp. 278-282 (1976).
Taylor et al., The performance of irradiation-crosslinked UHMWPE cups under abrasive conditions throughout hip joint stim. wear testing, 45th Annual Meeting, Ortho. Research Soc. (1999).
Shadrake et al, Journal of Materials Science 17: 145-156 (1982).
Sharpe, Dosimetry for Food Irradiation, Food Irradiation and the Chemist, pp. 109-123 (1990).
Shastri et al., Effects of Gamma Radiation Sterilization and In-Vitro Aging on Ultra High Molecular Weight Polyethylene, Bioengineering, Proceedings of the Ninth Northeast Conference, pp. 419-424 (1981).
Shastri et al., Effect of Aging on Ultra High Molecular Weight Polyethylene, ANTEC83, Conference Proceedings, pp. 16-18 (1983).
Shastri et al., Gamma Radiation and Environmental Aging Induced Changes in Medical Grade UHMW Polyethylene, Seventh Annual Meeting of the Society of Biomaterials, p. 99 (1981).
Shen, Effect of Irradiation on Chemically Crosslinked UltraHigh Molecular Weight Polyethylene (a dissertation Presented to the Univ. of Southern California) (1994).
Shen et al., Improving the Resistance to Wear and Oxidation of Acetabular Cups of UHMWPE by Gamma Radiation Crosslinking and Remelting, 24th Annual Meeting of the Society for Biomaterials (1998).
Shen et al., Wear 30: 349-364 (1974).
Shen, Analytical Chemistry 48(8): 886-888 (1977).
Shintani, J. of Radiation Sterilization 1:11-28 (1992).
Shintani et al., J. of Analytical Toxicology 13: 354-357 (1989).
Shintani et al., Journal of Biomaterials Applications 10: 23-58 (1995).
Silverman, Radiat. Phys. and Chem. 9: 1-15 (1977).
Silverman, Radiation-Induced and Chemical Crosslinking: A Brief Comparison, pp. 16-22 (1984).
Simon et al., The Journal of Bone and Joint Surgery 57-A(2): 226-230, (1975).
Singh et al., Radiation Processing: An Overview, Radiation Processing of Polymers, pp. 1-22, Oxford University Press, NY (1992).
Sochart, Clinical Orthopaedics and Related Research 363: 135-150 (1999).
Soudry et al., Clinical Orthopaedics and Related Research 205: 166-170 (1986).
Spadaro et al., Eur. Polym. J. 28(3): 257-259 (1992).
Spiegelberg et al., Radiat. Phys. Chem. 43(5): 433-444 (1994).
St. John et al., Comparison of the Wear Resistance of Two Cross-Linked Polyethylene Materials, 1999 Society for Biomaterials, 25th Annual Meeting Transactions, p. 501.
Stanley et al. The Journal of Thoracic and Cardiovascular Surgery 61(2): 309-314 (1971).
Steelman, AORN Journal 55(3): 773-787 (1992).
Streicher, The Behavior of UHMW-PE when Subjected to Sterilization by Ionizing Radiation, pp. 66-73 (1991).
Streicher, Change in Properties of High Molecular Weight Polyethylenes After Ionizing Irradiation for Sterilization and Modification, Radiation Processing for Plastics and Rubber III.
Streicher, Improving UHMWPE by Ionizing Irradiation Crosslinking During Sterilization, 17th Annual Meeting of the Society for Biomaterials, p. 181 (1991).
Streicher, Radiation Physics and Chemistry 31(4-6): 693-698 (1988).
Streicher, Investigation on Sterilization and Modification of High Molecular Weight Polyethylenes by Ionizing Irradiation, Reprint from Beta-Gamma 1/89, pp. 34-43 (1989).
Streicher, Radiat. Phys. Chem. 46(4 -6): 893-896 (1995).
Streicher et al., Examinations of Explanted Hip Joint Cups Made of UHMW-PE, Ultra-High Molecular Weight Polyethylene as Biomaterial in Orthopedic Surgery, pp. 196-201, Hogrefe & Huber Publishers (1991).
Stein, Ultrahigh Molecular Weight Polyethylenes (UHMWPE), Engineered Materials Handbook, vol. 2, Engineering Plastics, pp. 167-171 (1988).
Sun et al., Development of an Accelerated Aging Method for Evaluation of Long-term Irradiation Effects on UHMWPE Implants, pp. 969-970 (1994).
Sutula et al., Clinical Orthopaedic and Related Research 319: 28-40 (1995).
Swarts et al., Aging of Calcium Stearate-Free Polyethylene, Fifth World Biomaterials Congress (1996).
Szycher, Medical/Pharmaceutical Markets for Medical Plastics, High Performance Biomaterials, pp. 3-30 (1991).

(56) References Cited

OTHER PUBLICATIONS

Tanner et al., Clinical Orthopaedics and Related Research 317: 83-88 (1995).
Tayler et al., International Journal of Mass Spectrometry and Ion Processes, 89: 157-169 (1989).
Tompkins et al., Journal of Invertebrate Pathology 25: 139-140 (1975).
Trainor et al., Journal of Polymer Science: Polymer Physics Edition 15: 1077-1088 (1977).
Trent et al., Wear 36: 175-187 (1976).
Tripp, International Journal of Applied Radiation & Isotopes 6: 199-206 (1959).
Tsuruta et al., Polymer Engineering and Science 23(9): 521-529 (1983).
Uchida et al., International Orthpaedics (SICOT) 3: 285-291 (1980).
Ungar, Journal of Materials Science 16: 2635-2656 (1981).
Ungar et al., Effect of Radiation on the Crystals of Polyethylene and Paraffins: 1. Formation of the Hexagonal Lattice and the Destruction of Crystallinity in Polyethylene.
Ungethum et al., Der Einfluβ der Strahlensterilisation auf das Verschleißverhalten von Polyäthylen, Z. Orthop. 117: 790-794 (1979).
Urquhart et al., The Journal of Bone and Joint Surgery 80-A(11): 1641-1647 (1998).
van der Vis et al., Acta Orthop Scan 69(3): 248-252 (1998).
Van Lieshout et al., J.High Resol. Chromatogr. 19: 193-198 (1996).
Van Lieshout, et al., Journal of Chromatography A 764: 73-84 (1997).
Varner et al., J. Assoc. Off. Anal. Chem. 74(2): 367-374 (1991).
Venema, Journal of High Resolution Chromatography & Chromatography Communications 11: 128-131 (1988).
Venema, Journal of High Resolution Chromatography & Chromatography Communications 9: 637-640 (1986).
Vince et al., Techniques Orthop 1(4): 69-82 (1987).
Walker et al., MEP Ltd. 10(1): 33-38 (1981).
Walker et al., The Journal of Bone and Joint Surgery 59-B(2): 222-228 (1977).
Wallin, Meeting Report, Global Biocompatibility, Medical Device Technology, pp. 34, 36, 38 (1995).
Wang et al., Effects of Sterilization Methods on the Wear of Ultra-High Molecular Weight Polyethylene Acetabular Cups, 5th World Biomaterials Congress, Abstract No. 275 (1996).
Wang et al., Tribology International 31(1-3): 17-33 (1998).
Wang et al., The Impact of Lubricant Protein Concentration on the Outcome of Hip Joint Simulator Wear Testing, 1999 Society for Biomaterials, 25th Annual Meeting Transactions, p. 178.
Warty et al., European Polymer Journal 15: 445-452 (1979).
Watanabe et al., Journal of High Resolution Chromatography 14: 269-272 (1991).
Waterman et al., The Journal of Physical Chemistry 74(9): 1913-1922 (1970).
Webb et al., The Journal of Bone and Joint Surgery 62-B(2): 174-179 (1980).
Weightman et al., J. Biomechanics 6: 299-311 (1973).
Weightman et al., J. of Biomedical Materials Research 13: 669-672 (1979).
Weightman et al., The Journal of Bone and Joint Surgery 73-B(5): 806-810 (1991).
Wele et al., Frage nach Qualitatsverlust berechtigt? Einfluß ionisierender Strahlen auf Verpackungen & Auswirkungen auf die Lebensmittel, ZFL 50, Nr. 4 (1999).
Wesendorf, Journal of Chromatography Sciences 23: 521-523 (1985).
Whitbourne et al., Journal of Pharmaceutical Sciences 58(8): 1024-1025 (1969).
White et al., Clinical Orthopaedics and Related Research 331: 164-171 (1996).
Willert et al., Reaction of the Articular Capsule to Plastic & Metallic Wear Products from Joint Endoprostheses, Sulzer Technical Review, pp. 119-133 (1975).
Willed et al., J. Biomed. Mater. Res. 11: 157-164 (1977).
Williams et al., Journal of the American Chemical Society 81(12): 2919-2926 (1959).
Williams et al., Clinical Orthopaedics and Related Research 356: 170-180 (1998).
Winamo et al., Journal of Food Science, vol. 36: 892-895 (1971).
Winslow et al., Polymer Engineering and Science, pp. 273-278 (1966).
Winslow et al., Oxidative Embrittlement of Polyethylene, Trans. N.Y. Academy of Science, pp. 304-315 (1965).
Woods et al., Plastics and Rubber Processing and Applications 5: 157-164 (1985).
Woolson et al., The Journal of Bone and Joint Surgery 77-A(9): 1311-1314 (1995).
Wright et al., Clinical Orthopaedics & Related Research 205: 67-74 (1986).
Wright et al., Retrieval Analysis of Total Joint Replacement Components: A Six-Year Experience, Corrosion & Degradation of Implant Materials, pp. 415-428 (1985).
Woo, Advance Testing Methods for Biomaterials, Fundamental Properties and Test Methods, pp. 91-123 (1991).
Wroblewski, et al., The Journal of Bone and Joint Surgery 78-B(2): 280-285 (1996).
Wroblewski, The Journal of Bone and Joint Surgery 61-B(4): 498-500 (1979).
Wrona et al., Clinical Orthopaedics and Related Research 299: 92-103 (1994).
Wunderlich et al., J. Polymer Science 5(Part A-2): 987-988 (1967).
Wünsche, J. Macromol. Sci. and Phys. B23(1): 65-84 (1984).
Wünsche et al., J. Macromol. Sci. and Phys. B22(2): 169-183 (1983).
Yeh et al., J. of Polymer Science 29: 371-388 (1991).
Yoshii et al., Polymer Communications 28: 278-280 (1987).
Yousefi et al., Radiat. Phys. Chem. 44(6): 645-649 (1994).
Zachariades et al., Journal of Polymer Science 21: 821-830 (1983).
Zhao et al., Journal of Applied Polymer Science 50: 1797-1801 (1993).
Zlatkevich, Journal of Polymer Science, Polymer Physics Edition 23: 2633-2634 (1985).
Zoepfl et al., J. Polymer Science, Polymer Chemisty Edition 22: 2017-2032 (1984).
Zoepfl et al., J. Polymer Science, Polymer Chemisty Edition 22: 2033-2045 (1984).
Dept. of Health, Education & Welfare, Ethylene Oxide, Ethylene Chlorohydrin, and Ethylene Glycol, Fed. Reg. 43(122): 27474-24783 (1978).
Code of Federal Regulations, Food & Drugs 21, Parts 170-199, Rev. as of Apr. 1, 1989.
Blunn et al., The Journal of Bone and Joint Surgery 84-B: 946-949 (2002).
Dijkstra, Entanglements and Cross-Links in Ultra-High Molecular Weight Polyethylene, pp. 1-101 (1989).
Dijkstra et al., Polymer Bulletin 17: 507-513 (1987).
Goetz et al., J Bone Joint Surg Am. 76-A(8): 1121-1129 (1994).
Jahan et al., Journal of Biomedical Materials Research 25: 1005-1017 (1991).
Crosslinked Polyethylene Product Comparison Sheet Knee/Quick Comparison Knee (Nov. 15, 2006).

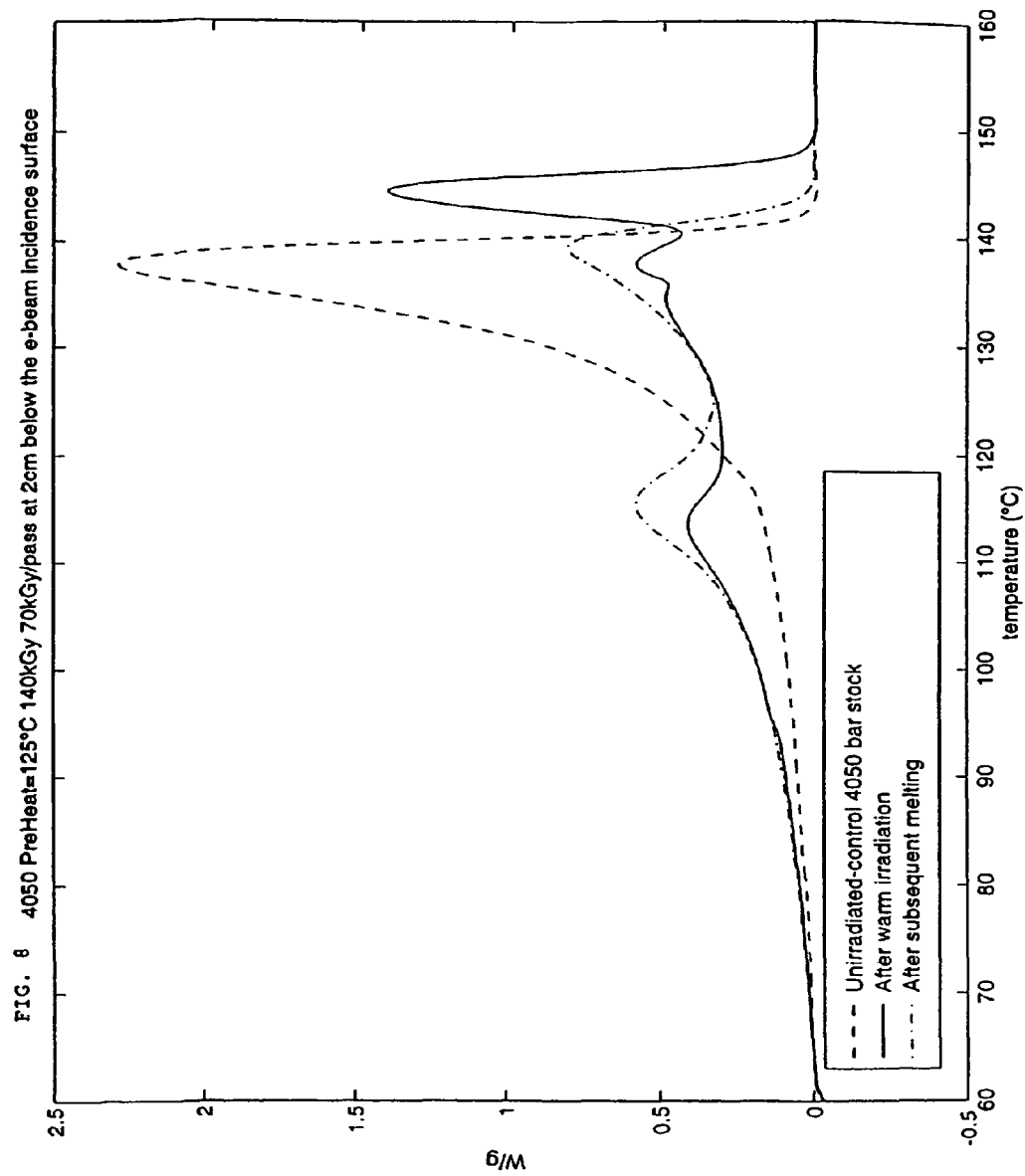

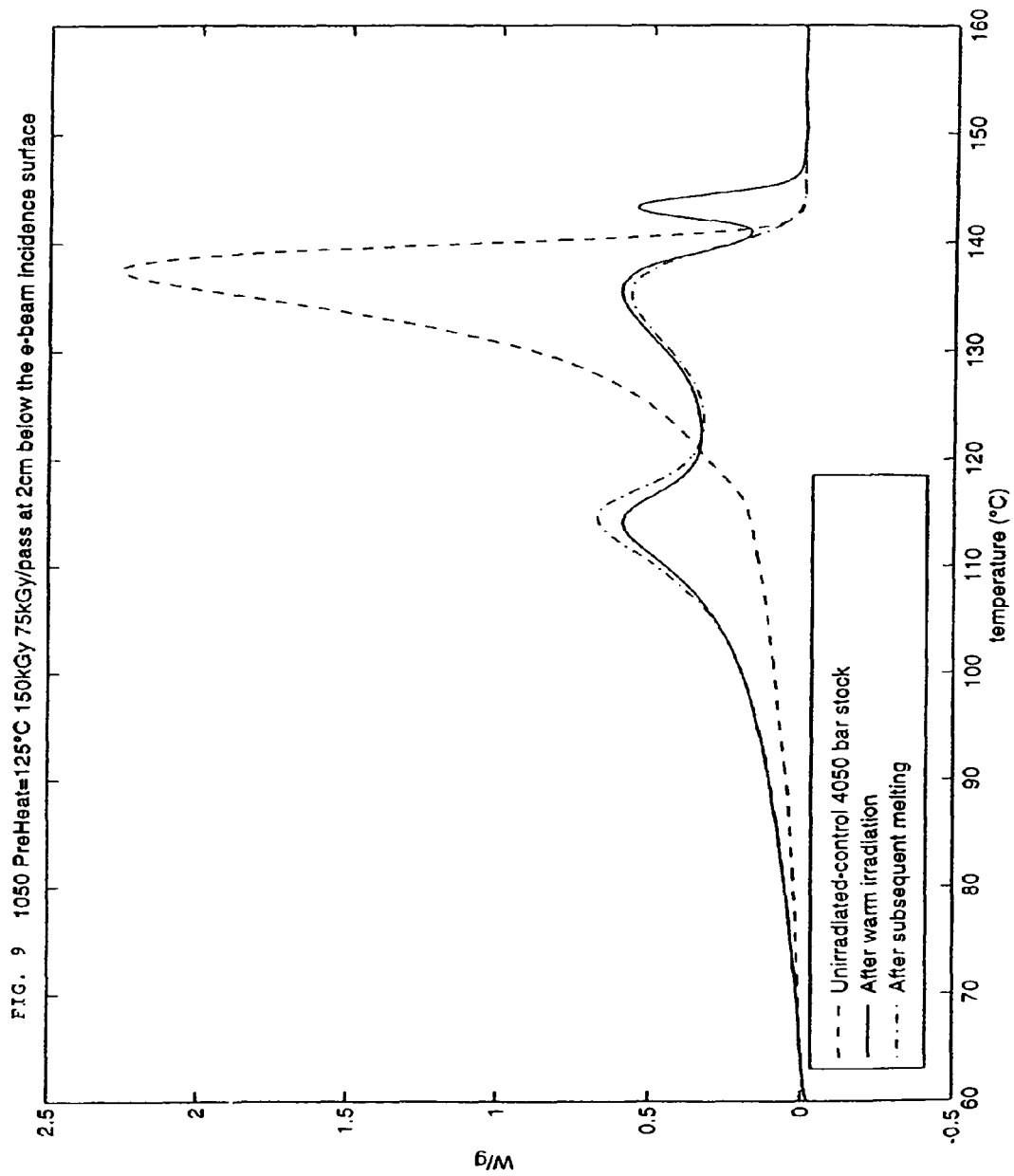
FIG. 9 1050 PreHeat=125°C 150kGy 75kGy/pass at 2cm below the e-beam incidence surface

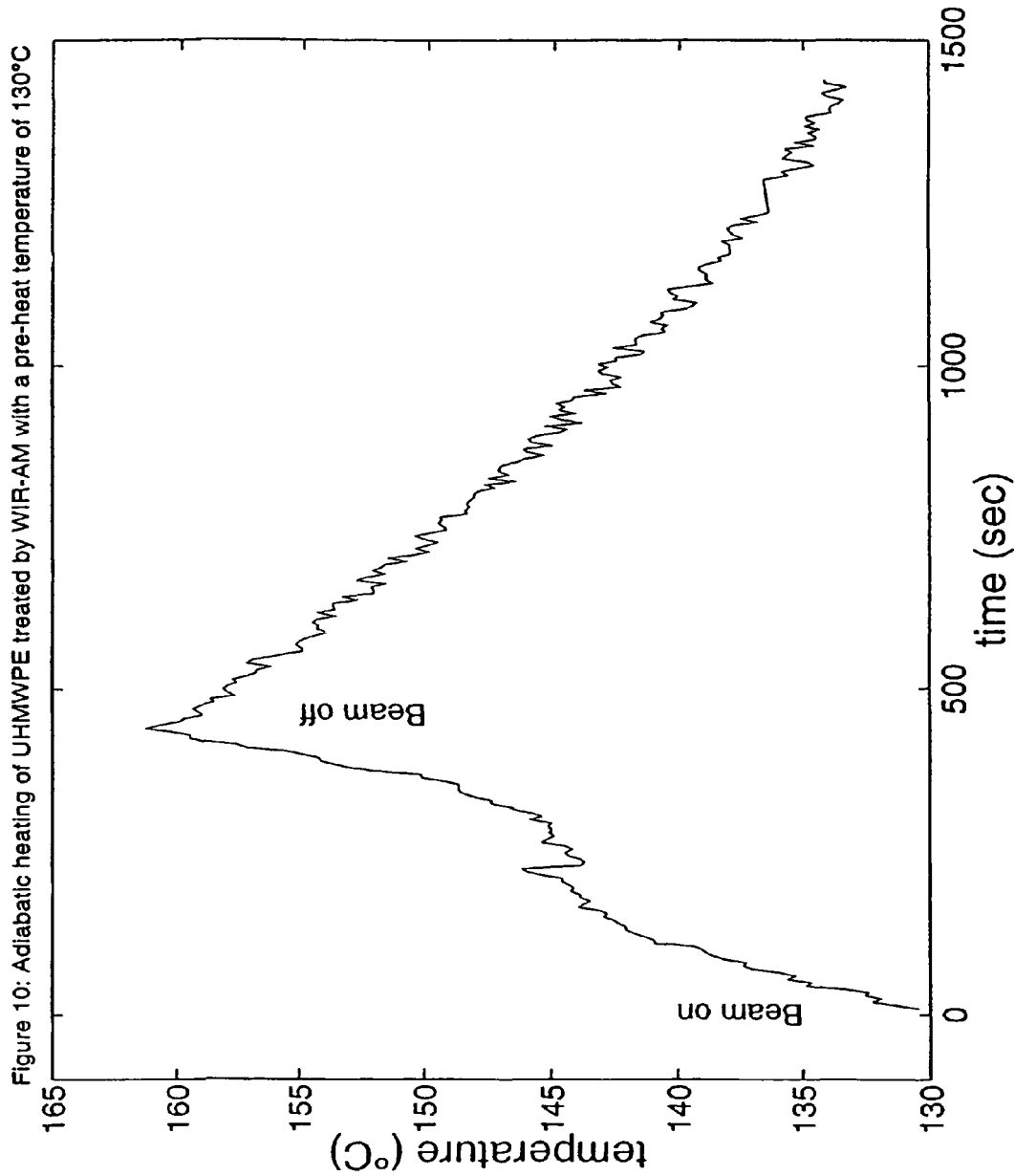

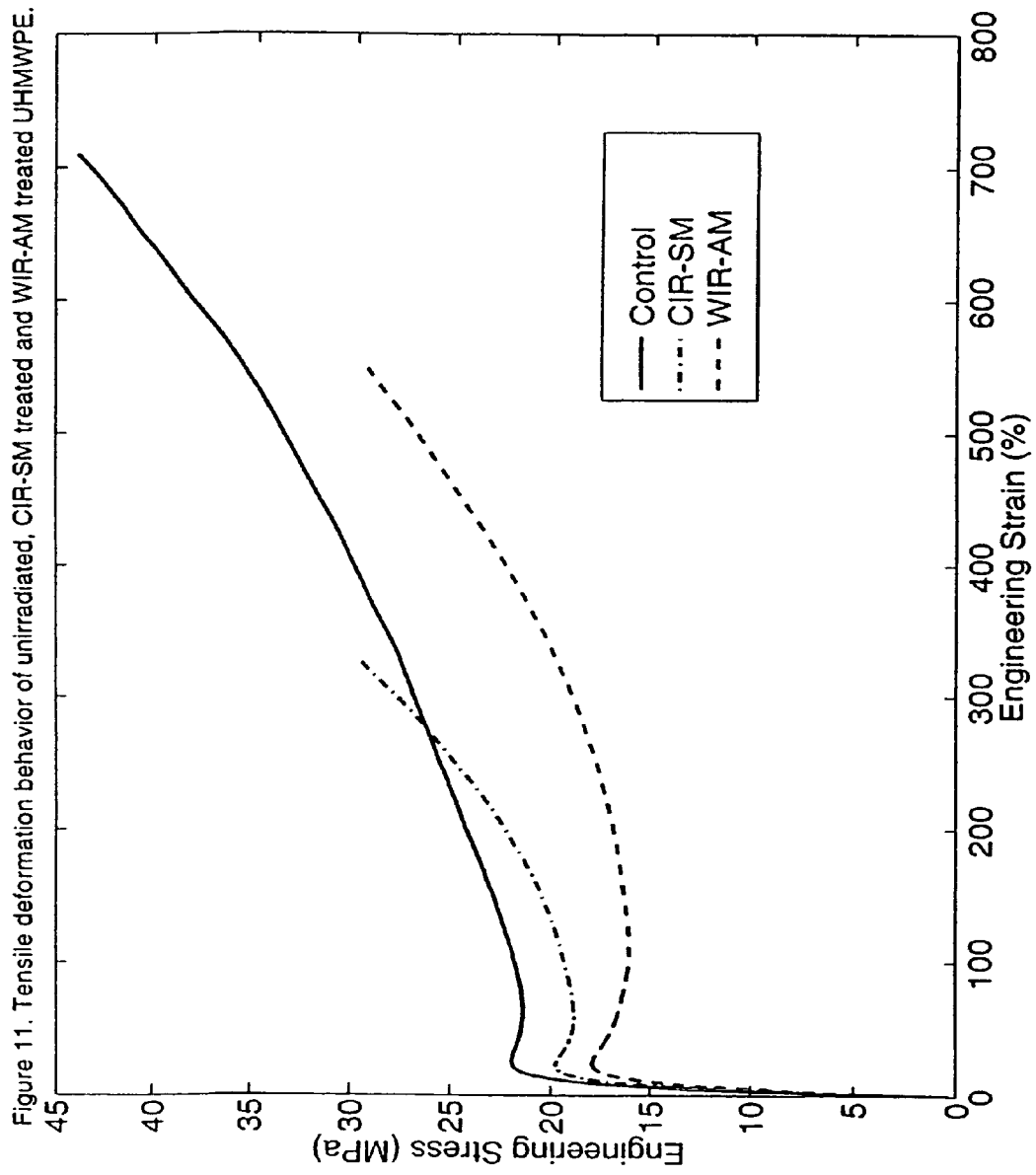

RADIATION MELT TREATED ULTRA HIGH MOLECULAR WEIGHT POLYETHYLENE PROSTHETIC DEVICES

This application is a continuation of U.S. Ser. No. 09/764,445, filed Jan. 19, 2001; which is a continuation of U.S. Ser. No. 09/572,324 (abandoned), filed May 18, 2000; which is a continuation of U.S. Ser. No. 08/798,638 (abandoned), filed Feb. 11, 1997; which is a continuation-in-part of U.S. Ser. No. 08/726,313 (abandoned), filed Oct. 2, 1996. The entire contents of each of the above-identified applications are hereby incorporated by reference.

FIELD OF THE INVENTION

The present invention relates to the orthopedic field and the provision of prostheses, such as hip and knee implants, as well as methods of manufacture of such devices and material used therein.

BACKGROUND OF THE INVENTION

The use of synthetic polymers, e.g., ultra high molecular weight polyethylene, with metallic alloys has revolutionized the field of prosthetic implants, e.g., their use in total joint replacements for the hip or knee. Wear of the synthetic polymer against the metal of the articulation, however, can result in severe adverse effects which predominantly manifest after several years. Various studies have concluded that such wear can lead to the liberation of ultrafine particles of polyethylene into the periprosthetic tissues. It has been suggested that the abrasion stretches the chain folded crystallites to form anisotropic fibrillar structures at the articulating surface. The stretched-out fibrils can then rupture, leading to production of submicron sized particles. In response to the progressive ingress of these polyethylene particles between the prosthesis and bone, macrophage-induced resorption of the periprosthetic bone is initiated. The macrophage, often being unable to digest these polyethylene particles, synthesize and release large numbers of cytokines and growth factors which can ultimately result in bone resorption by osteoclasts and monocytes. This osteolysis can contribute to mechanical loosening of the prosthesis components, thereby sometimes requiring revision surgery with its concomitant problems.

SUMMARY OF THE INVENTION

It is an object of the invention to provide an implantable prosthesis device formed at least in part of radiation treated ultra high molecular weight polyethylene (UHMWPE) having no detectable free radicals, so as to reduce production of fine particles from the prosthesis during wear of the prosthesis.

It is another object of the invention to reduce osteolysis and inflammatory reactions resulting from prosthesis implants.

It is yet another object of the invention to provide a prosthesis which can remain implanted within a person for prolonged periods of time.

It is yet another object of the invention to provide improved UHMWPE which can be used in the prostheses of the preceding objects and/or in other fabricated articles.

Still another object of the invention is to provide improved UHMWPE which has a high density of cross-links and no detectable free radicals.

A still further object of the invention is to provide improved UHMWPE which has improved wear resistance.

According to the invention, a medical prosthesis for use within the body which is formed of radiation treated ultra high molecular weight polyethylene (UHMWPE) having substantially no detectable free radicals, is provided. The radiation can be, e.g., gamma or electron radiation. The UHMWPE has a cross-linked structure. Preferably, the UHMWPE is substantially not oxidized and is substantially oxidation resistant. Variations include, e.g., the UHMWPE having three melting peaks, two melting peaks or one melting peak. In certain embodiments, the UHMWPE has a polymeric structure with less than about 50% crystallinity, less than about 290 Å lamellar thickness and less than about 940 MPa tensile elastic modulus, so as to reduce production of fine particles from the prosthesis during wear of the prosthesis. Part of the prosthesis can be, e.g., in the form of a cup or tray shaped article having a load bearing surface made of this UHMWPE. This load bearing surface can be in contact with a second part of the prosthesis having a mating load bearing surface of a metallic or ceramic material.

Another aspect of the invention is radiation treated UHMWPE having substantially no detectable free radicals. This UHMWPE has a cross-linked structure. Preferably, this UHMWPE is substantially not oxidized and is substantially oxidation resistant. Variations include, e.g., the UHMWPE having three melting peaks, two melting peaks or one melting peak.

Other aspects of the invention are fabricated articles, e.g., with a load bearing surface, and wear resistant coatings, made from such UHMWPE. One embodiment is where the fabricated article is in the form of a bar stock which is capable of being shaped into articles by conventional methods, e.g., machining.

Yet another aspect of the invention includes a method for making a cross-linked UHMWPE having substantially no detectable free radicals. Conventional UHMWPE having polymeric chains is provided. This UHMWPE is irradiated so as to cross-link said polymeric chains. The UHMWPE is heated above the melting temperature of the UHMWPE so that there are substantially no detectable free radicals in the UHMWPE. The UHMWPE is then cooled to room temperature. In certain embodiments, the cooled UHMWPE is machined and/or sterilized.

One preferred embodiment of this method is called CIR-SM, i.e., cold irradiation and subsequent melting. The UHMWPE that is provided is at room temperature or below room temperature.

Another preferred embodiment of this method is called WIR-SM, i.e., warm irradiation and subsequent melting. The UHMWPE that is provided is pre-heated to a temperature below the melting temperature of the UHMWPE.

Another preferred embodiment of this method is called WIR-AM, i.e., warm irradiation and adiabatic melting. In this embodiment, the UHMWPE that is provided is pre-heated to a temperature below the melting temperature of the UHMWPE, preferably between about 100° C. to below the melting temperature of the UHMWPE. Preferably, the UHMWPE is in an insulating material so as to reduce heat loss from the UHMWPE during processing. The pre-heated UHMWPE is then irradiated to a high enough total dose and at a fast enough dose rate so as to generate enough heat in the polymer to melt substantially all the crystals in the material and thus ensure elimination of substantially all detectable free radicals generated by, e.g., the irradiating step. It is preferred that the irradiating step use electron irradiation so as to generate such adiabatic heating.

Another aspect of this invention is the product made in accordance with the above described method.

Yet another aspect of this invention, called MIR, i.e., melt irradiation, is a method for making crosslinked UHMWPE. Conventional UHMWPE is provided. Preferably, the UHMWPE is surrounded with an inert material that is substantially free of oxygen. The UHMWPE is heated above the melting temperature of the UHMWPE so as to completely melt all crystalline structure. The heated UHMWPE is irradiated, and the irradiated UHMWPE is cooled to about 25° C.

In an embodiment of MIR, highly entangled and crosslinked UHMWPE is made. Conventional UHMWPE is provided. Preferably, the UHMWPE is surrounded with an inert material that is substantially free of oxygen. The UHMWPE is heated above the melting temperature of the UHMWPE for a time sufficient to enable the formation of entangled polymer chains in the UHMWPE. The heated UHMWPE is irradiated so as to trap the polymer chains in the entangled state, and the irradiated UHMWPE is cooled to about 25° C.

The invention also features a method of making a medical prosthesis from radiation treated UHMWPE having substantially no detectable free radicals, the prosthesis resulting in reduced production of particles from the prosthesis during wear of the prosthesis. Radiation treated UHMWPE having no detectable free radicals is provided. A medical prosthesis is formed from this UHMWPE so as to reduce production of particles from the prosthesis during wear of the prosthesis, the UHMWPE forming a load bearing surface of the prosthesis. Formation of the prosthesis can be accomplished by standard procedures known to those skilled in the art, e.g., machining.

Also provided in this invention is a method of treating a body in need of a medical prosthesis. A shaped prosthesis formed of radiation treated UHMWPE having substantially no detectable free radicals is provided. The prosthesis is applied to the body in need of the prosthesis. The prosthesis reduces production of particles from the prosthesis during wear of the prosthesis. In preferred embodiments, the UHMWPE forms a load bearing surface of the prosthesis.

The above and other objects, features and advantages of the present invention will be better understood from the following specification when read in conjunction with the accompanying drawings.

BRIEF DESCRIPTION OF THE DRAWINGS

FIG. 8 is a graph showing DSC melting endotherms for Hoechst-Celanese GUR 4050 UHMWPE prepared using warm irradiation and partial adiabatic melting (WIR-AM), with and without subsequent heating.

FIG. 9 is a graph showing DSC melting endotherms for Hoechst-Celanese GUR 1050 UHMWPE prepared using warm irradiation and partial adiabatic melting (WIR-AM), with and without subsequent heating.

FIG. 10 is a graph showing adiabatic heating of UHMWPE treated by WIR-AM with a pre-heat temperature of 130° C.

FIG. 11 is a graph showing tensile deformation behavior of unirradiated UHMWPE, CIR-SM treated UHMWPE, and WIR-AM treated UHMWPE.

DETAILED DESCRIPTION

This invention provides a medical prosthesis for use within the body which is formed of radiation treated ultra high molecular weight polyethylene (UHMWPE) which has substantially no detectable free radicals.

Figure 1:
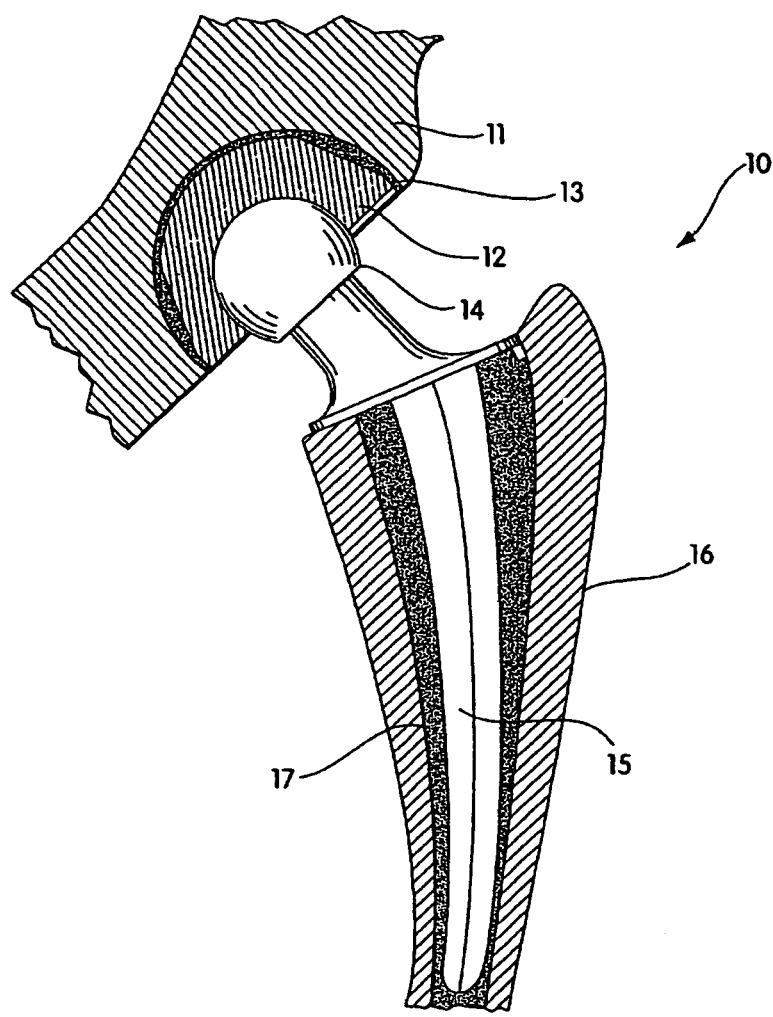
FIG. 1 is a cross-sectional view through the center of a medical hip joint prosthesis in accordance with a preferred embodiment of this invention.

A medical prosthesis in the form of a hip joint prosthesis is generally illustrated at 10 in FIG. 1. The prosthesis shown has a conventional ball head 14 connected by a neck portion to a stem 15 which is mounted by conventional cement 17 to the femur 16. The ball head can be of conventional design and formed of stainless steel or other alloys as known in the art. The radius of the ball head closely conforms to the inner cup radius of an acetabular cup 12 which can be mounted in cement 13 directly to the pelvis 11. Alternatively, a metallic acetabular shell can be cemented to the pelvis 11 and the acetabular cup 12 can form a coating or liner connected to the metallic acetabular shell by means as are known in the art.

The specific form of the prosthesis can vary greatly as known in the art. Many hip joint constructions are known and other prostheses such as knee joints, shoulder joints, ankle joints, elbow joints and finger joints are known. All such prior art prostheses can be benefited by making at least one load bearing surface of such prosthesis of a high molecular weight polyethylene material in accordance with this invention. Such load bearing surfaces can be in the form of layers, linings or actual whole devices as shown in FIG. 1. In all cases, it is preferred that the load bearing surface act in conjunction with a metallic or ceramic mating member of the prosthesis so that a sliding surface is formed therebetween. Such sliding surfaces are subject to breakdown of the polyethylene as known in the prior art. Such breakdown can be greatly diminished by use of the materials of the present invention.

Figure 2:
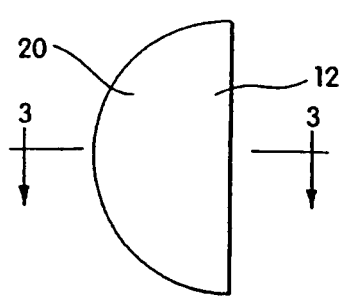
FIG. 2 is a side view of an acetabular cup liner as shown in FIG. 1.
Figure 3:
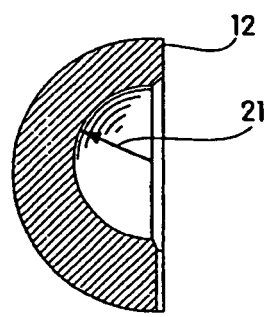
FIG. 3 is a cross-sectional view through line 3-3 of FIG. 2.

FIG. 2 shows the acetabular cup 12 in the form of a half hollow ball-shaped device better seen in the cross-section of FIG. 3. As previously described, the outer surface 20 of the acetabular cup need not be circular or hemispherical but can be square or of any configuration to be adhered directly to the pelvis or to the pelvis through a metallic shell as known in the art. The radius of the acetabular cup shown at 21 in FIG. 3 of the preferred embodiment ranges from about 20 mm to about 35 mm. The thickness of the acetabular cup from its generally hemispherical hollow portion to the outer surface 20 is preferably about 8 mm. The outer radius is preferably in the order of about 20 mm to about 35 mm.

In some cases, the ball joint can be made of the UHMWPE of this invention and the acetabular cup formed of metal, although it is preferred to make the acetabular cup or acetabular cup liner of UHMWPE to mate with the metallic ball. The particular method of attachment of the components of the prosthesis to the bones of the body can vary greatly as known in the art.

The medical prosthesis of this invention is meant to include whole prosthetic devices or portions thereof, e.g., a component, layer or lining. The medical prosthesis includes, e.g., orthopedic joint and bone replacement parts, e.g., hip, knee, shoulder, elbow, ankle or finger replacements. The prosthesis can be in the form, e.g., of a cup or tray shaped article which has a load bearing surface. Other forms known to those skilled in the art are also included in the invention. Medical prostheses are also meant to include any wearing surface of a prosthesis, e.g., a coating on a surface of a prosthesis in which the prosthesis is made from a material other than the UHMWPE of this invention.

The prostheses of this invention are useful for contact with metal containing parts formed of, e.g., cobalt chromium alloy, stainless steel, titanium alloy or nickel cobalt alloy, or with ceramic containing parts. For example, a hip joint is constructed in which a cup shaped article having an inner radius of 25 mm, is contacted with a metal ball having an outer radius of 25 mm, so as to closely mate with the cup shaped article. The load bearing surface of the cup shaped article of this example is made from the UHMWPE of this invention, preferably having a thickness of at least about 1 mm, more preferably having a thickness of at least about 2 mm, more preferably having a thickness of at least about ¼ inch, and more preferably yet having a thickness of at least about ⅓ inch.

The prostheses can have any standard known form, shape, or configuration, or be a custom design, but have at least one load bearing surface of UHMWPE of this invention.

The prostheses of this invention are non-toxic to humans. They are not subject to deterioration by normal body constituents, e.g., blood or interstitial fluids. They are capable of being sterilized by standard means, including, e.g., heat or ethylene oxide.

By UHMWPE is meant linear non-branched chains of ethylene that have molecular weights in excess of about 500,000, preferably above about 1,000,000, and more preferably above about 2,000,000. Often the molecular weights can be at least as high as about 8,000,000. By initial average molecular weight is meant the average molecular weight of the UHMWPE starting material, prior to any irradiation.

Conventional UHMWPE is standardly generated by Ziegler-Natta catalysis, and as the polymer chains are generated from the surface catalytic site, they crystallize, and interlock as chain folded crystals. Examples of known UHMWPE powders include Hifax Grade 1900 polyethylene (obtained from Montell, Wilmington, Del.), having a molecular weight of about 2 million g/mol and not containing any calcium stearate; GUR 4150, also known as GUR 415, (obtained from Hoescht Celanese Corp., Houston, Tex.), having a molecular weight of about 4-5 million g/mol and containing 500 ppm of calcium stearate; GUR 4050 (obtained from Hoescht Celanese Corp., Houston, Tex.), having a molecular weight of about 4-5 million g/mol and not containing any calcium stearate; GUR 4120 (obtained from Hoescht Celanese Corp., Houston, Tex.), having a molecular weight of about 2 million g/mol and containing 500 ppm of calcium stearate; GUR 4020 (obtained from Hoescht Celanese Corp., Houston, Tex.), having a molecular weight of about 2 million g/mol and not containing any calcium stearate; GUR 1050 (obtained from Hoescht Celanese Corp., Germany), having a molecular weight of about 4-5 million g/mol and not containing any calcium stearate; GUR 1150 (obtained from Hoescht Celanese Corp., Germany), having a molecular weight of about 4-5 million g/mol and containing 500 ppm of calcium stearate; GUR 1020 (obtained from Hoescht Celanese Corp., Germany), having a molecular weight of about 2 million g/mol and not containing any calcium stearate; and GUR 1120 (obtained from Hoescht Celanese Corp., Germany), having a molecular weight of about 2 million g/mol and containing 500 ppm of calcium stearate. Preferred UHMWPEs for medical applications are GUR 4150, GUR 1050 and GUR 1020. By resin is meant powder.

UHMWPE powder can be consolidated using a variety of different techniques, e.g., ram extrusion, compression molding or direct compression molding. In ram extrusion, the UHMWPE powder is pressurized through a heated barrel whereby it is consolidated into a rod stock, i.e., bar stock (can be obtained, e.g., from Westlake Plastics, Lenni, Pa.). In compression molding, the UHMWPE powder is consolidated under high pressure into a mold (can be obtained, e.g., from Poly-Hi Solidur, Fort Wayne, Ind., or Perplas, Stanmore, U.K.). The shape of the mold can be, e.g., a thick sheet. Direct compression molding is preferably used to manufacture net shaped products, e.g., acetabular components or tibial knee inserts (can be obtained, e.g., from Zimmer, Inc., Warsaw, Ind.). In this technique, the UHMWPE powder is compressed directly into the final shape. "Hockey pucks", or pucks, are generally machined from ram extruded bar stock or from a compression molded sheet.

By radiation treated UHMWPE is meant UHMWPE which has been treated with radiation, e.g., gamma radiation or electron radiation, so as to induce cross-links between the polymeric chains of the UHMWPE.

By substantially no detectable free radicals is meant substantially no free radicals as measured by electron paramagnetic resonance, as described in Jahan et al., J. Biomedical Materials Research 25: 1005 (1991). Free radicals include, e.g., unsaturated trans-vinylene free radicals. UHMWPE that has been irradiated below its melting point with ionizing radiation contains cross-links as well as long-lived trapped free radicals. These free radicals react with oxygen over the long-term and result in the embrittlement of the UHMWPE through oxidative degradation. An advantage of the UHMWPE and medical prostheses of this invention is that radiation treated UHMWPE is used which has no detectable free radicals. The free radicals can be eliminated by any method which gives this result, e.g., by heating the UHMWPE above its melting point such that substantially no residual crystalline structure remains. By eliminating the crystalline structure, the free radicals are able to recombine and thus are eliminated.

The UHMWPE which is used in this invention has a cross-linked structure. An advantage of having a cross-linked structure is that it will reduce production of particles from the prosthesis during wear of the prosthesis.

It is preferred that the UHMWPE be substantially not oxidized. By substantially not oxidized is meant that the ratio of the area under the carbonyl peak at 1740 $cm^{-1}$ in the FTIR spectra to the area under the peak at 1460 $cm^{-1}$ in the FTIR spectra of the cross-linked sample be of the same order of magnitude as the ratio for the sample before cross-linking.

It is preferred that the UHMWPE be substantially oxidation resistant. By substantially oxidation resistant is meant that it remains substantially not oxidized for at least about 10 years. Preferably, it remains substantially not oxidized for at least about 20 years, more preferably for at least about 30 years, more preferably yet for at least about 40 years, and most preferably for the entire lifetime of the patient.

In certain embodiments, the UHMWPE has three melting peaks. The first melting peak preferably is about 105° C. to about 120° C., more preferably is about 110° C. to about 120° C., and most preferably is about 118° C. The second melting peak preferably is about 125° C. to about 140° C., more preferably is about 130° C. to about 140° C., more preferably yet is about 135° C., and most preferably is about 137° C. The third melting peak preferably is about 140° C. to about 150° C., more preferably is about 140° C. to about 145° C., and most preferably is about 144° C. In certain embodiments, the UHMWPE has two melting peaks. The first melting peak preferably is about 105° C. to about 120° C., more preferably is about 110° C. to about 120° C., and most preferably is about 118° C. The second melting peak preferably is about 125° C. to about 140° C., more preferably is about 130° C. to about 140° C., more preferably yet is about 135° C., and most preferably is about 137° C. In certain embodiments, the UHMWPE has one melting peak. The melting peak preferably is about 125° C. to about 140° C., more preferably is about 130° C. to about 140° C., more preferably yet is about 135° C., and most preferably is about 137° C. Preferably, the UHMWPE has two melting peaks. The number of melting peaks is determined by differential scanning calorimetry (DSC) at a heating rate of 10° C./min.

The polymeric structure of the UHMWPE used in the prostheses of this invention results in the reduction of production of UHMWPE particles from the prosthesis during wear of the prosthesis. As a result of the limited number of particles being shed into the body, the prosthesis exhibits longer implant life. Preferably, the prosthesis can remain implanted in the body for at least 10 years, more preferably for at least 20 years and most preferably for the entire lifetime of the patient.

The invention also includes other fabricated articles made from radiation treated UHMWPE having substantially no detectable free radicals. Preferably, the UHMWPE which is used for making the fabricated articles has a cross-linked structure. Preferably, the UHMWPE is substantially oxidation resistant. In certain embodiments, the UHMWPE has three melting peaks. In certain embodiments, the UHMWPE has two melting peaks. In certain embodiments, the UHMWPE has one melting peak. Preferably, the UHMWPE has two melting peaks. The fabricated articles include shaped articles and unshaped articles, including, e.g., machined objects, e.g., cups, gears, nuts, sled runners, bolts, fasteners, cables, pipes and the like, and bar stock, films, cylindrical bars, sheeting, panels, and fibers. Shaped articles can be made, e.g., by machining. The fabricated article can be, e.g., in the form of a bar stock which is capable of being shaped into a second article by machining. The fabricated articles are particularly suitable for load bearing applications, e.g., high wear resistance applications, e.g., as a load bearing surface, e.g., an articulating surface, and as metal replacement articles. Thin films or sheets of the UHMWPE of this invention can also be attached, e.g., with glue, onto supporting surfaces, and thus used as a wear resistant load bearing surface.

The invention also includes radiation treated UHMWPE which has substantially no detectable free radicals. The UHMWPE has a cross-linked structure. Preferably, the UHMWPE is substantially not oxidized and is substantially oxidation resistant. In certain embodiments, the UHMWPE has three melting peaks. In certain embodiments, the UHMWPE has two melting peaks. In certain embodiments, the UHMWPE has one melting peak. Preferably, the UHMWPE has two melting peaks. Depending upon the particular processing used to make the UHMWPE, certain impurities may be present in the UHMWPE of this invention, including, e.g., calcium stearate, mold release agents, extenders, anti-oxidants and/or other conventional additives to polyethylene polymers.

The invention also provides a method for making cross-linked UHMWPE having substantially no detectable free radicals. Preferably, this UHMWPE is for use as a load bearing article with high wear resistance. Conventional UHMWPE having polymeric chains is provided. The conventional UHMWPE can be in the form of, e.g., a bar stock, a shaped bar stock, e.g., a puck, a coating, or a fabricated article, e.g., a cup or tray shaped article for use in a medical prosthesis. By conventional UHMWPE is meant commercially available high density (linear) polyethylene of molecular weights greater than about 500,000. Preferably, the UHMWPE starting material has an average molecular weight of greater than about 2 million. By initial average molecular weight is meant the average molecular weight of the UHMWPE starting material, prior to any irradiation. The UHMWPE is irradiated so as to cross-link the polymeric chains. The irradiation can be done in an inert or non-inert environment. Preferably, the irradiation is done in a non-inert environment, e.g., air. The irradiated UHMWPE is heated above the melting temperature of the UHMWPE so that there are substantially no detectable free radicals in the UHMWPE. The heated UHMWPE is then cooled to room temperature. Preferably, the cooling step is at a rate greater than about 0.1° C./minute. Optionally, the cooled UHMWPE can be machined. For example, if any oxidation of the UHMWPE occurred during the irradiating step, it can be machined away if desired, by any method known to those skilled in the art. And optionally, the cooled UHMWPE, or the machined UHMWPE, can be sterilized by any method known to those skilled in the art.

One preferred embodiment of this method is called CIRSM, i.e., cold irradiation and subsequent melting. In this embodiment, the UHMWPE that is provided is at room temperature or below room temperature. Preferably, it is about 20° C. Irradiation of the UHMWPE can be with, e.g., gamma irradiation or electron irradiation. In general, gamma irradiation gives a high penetration depth but takes a longer time, resulting in the possibility of more in-depth oxidation. In general, electron irradiation gives more limited penetration depths but takes a shorter time, and the possibility of extensive oxidation is reduced. The irradiation is done so as to cross-link the polymeric chains. The irradiation dose can be varied to control the degree of cross-linking and crystallinity in the final UHMWPE product. Preferably, the total absorbed dose of the irradiation is about 0.5 to about 1,000 Mrad, more preferably about 1 to about 100 Mrad, more preferably yet about 4 to about 30 Mrad, more preferably yet about 20 Mrad, and most preferably about 15 Mrad. Preferably, a dose rate is used that does not generate enough heat to melt the UHMWPE. If gamma irradiation is used, the preferred dose rate is about 0.05 to about 0.2 Mrad/minute. If electron irradiation is used, preferably the dose rate is about 0.05 to about 3,000 Mrad/minute, more preferably about 0.05 to about 5 Mrad/minute, and most preferably about 0.05 to about 0.2 Mrad/minute. The dose rate in electron irradiation is determined by the following parameters: (1) the power of the accelerator in kW, (ii) the conveyor speed, (iii) the distance between the surface of the irradiated specimen and the scan horn, and (iv) the scan width. The dose rate at an e-beam facility is often measured in Mrads per pass under the rastering e-beam. The dose rates indicated herein as Mrad/minute can be converted to Mrad/pass by using the following equation:

$$D_{Mrad/min} = D_{Mrad/pass} \times v_c + l$$

where $D_{Mrad/min}$ is the dose rate in Mrad/min, $D_{Mrad/pass}$ is the dose rate in Mrad/pass, $v_c$ is the conveyor speed and l is the length of the specimen that travels through the e-beam raster area. When electron irradiation is used, the energy of the electrons can be varied to change the depth of penetration of the electrons. Preferably, the energy of the electrons is about 0.5 MeV to about 12 MeV, more preferably about 5 MeV to about 12 MeV. Such manipulability is particularly useful when the irradiated object is an article of varying thickness or depth, e.g., an articular cup for a medical prosthesis.

The irradiated UHMWPE is heated above the melting temperature of the UHMWPE so that there are no detectable free radicals in the UHMWPE. The heating provides the molecules with sufficient mobility so as to eliminate the constraints derived from the crystals of the UHMWPE, thereby allowing essentially all of the residual free radicals to recombine. Preferably, the UHMWPE is heated to a temperature of about 137° C. to about 300° C., more preferably about 140° C. to about 300° C., more preferably yet about 140° C. to about 190° C., more preferably yet about 145° C. to about 300° C., more preferably yet about 145° C. to about 190° C., more preferably yet about 146° C. to about 190° C., and most preferably about 150° C. Preferably, the temperature in the heating step is maintained for about 0.5 minutes to about 24 hours, more preferably about 1 hour to about 3 hours, and most preferably about 2 hours. The heating can be carried out, e.g., in air, in an inert gas, e.g., nitrogen, argon or helium, in a sensitizing atmosphere, e.g., acetylene, or in a vacuum. It is preferred that for the longer heating times, that the heating be carried out in an inert gas or under vacuum.

Another preferred embodiment of this method is called WIR-SM, i.e., warm irradiation and subsequent melting. In this embodiment, the UHMWPE that is provided is pre-heated to a temperature below the melting temperature of the UHMWPE. The pre-heating can be done in an inert or non-inert environment. It is preferred that this pre-heating is done in air. Preferably, the UHMWPE is pre-heated to a temperature of about 20° C. to about 135° C., more preferably to a temperature greater than about 20° C. to about 135° C., and most preferably to a temperature of about 50° C. The other parameters are as described above for the CIR-SM embodiment, except that the dose rate for the irradiating step using electron irradiation is preferably about 0.05 to about 10 Mrad/minute, and more preferably is about 4 to about 5 Mrad/minute; and the dose rate for the irradiating step using gamma irradiation is preferably about 0.05 to about 0.2 Mrad/minute, and more preferably is about 0.2 Mrad/minute.

Another preferred embodiment of this method is called WIR-AM, i.e., warm irradiation and adiabatic melting. In this embodiment, the UHMWPE that is provided is pre-heated to a temperature below the melting temperature of the UHMWPE. The pre-heating can be done in an inert or non-inert environment. It is preferred that this pre-heating is done in air. The pre-heating can be done, e.g., in an oven. It is preferred that the pre-heating is to a temperature between about 100° C. to below the melting temperature of the UHMWPE. Preferably, the UHMWPE is pre-heated to a temperature of about 100° C. to about 135° C., more preferably the temperature is about 130° C., and most preferably is about 120° C. Preferably, the UHMWPE is in an insulating material so as to reduce heat loss from the UHMWPE during processing. The heat is meant to include, e.g., the pre-heat delivered before irradiation and the heat generated during irradiation. By insulating material is meant any type of material which has insulating properties, e.g., a fiberglass pouch.

The pre-heated UHMWPE is then irradiated to a high enough total dose and at a fast enough dose rate so as to generate enough heat in the polymer to melt substantially all the crystals in the material and thus ensure elimination of substantially all detectable free radicals generated by, e.g., the irradiating step. It is preferred that the irradiating step use electron irradiation so as to generate such adiabatic heating. By adiabatic heating is meant no loss of heat to the surroundings during irradiation. Adiabatic heating results in adiabatic melting if the temperature is above the melting point. Adiabatic melting is meant to include complete or partial melting. The minimum total dose is determined by the amount of heat necessary to heat the polymer from its initial temperature (i.e., the pre-heated temperature discussed above) to its melting temperature, and the heat necessary to melt all the crystals, and the heat necessary to heat the polymer to a pre-determined temperature above its melting point. The following equation describes how the amount of total dose is calculated:

$$\text{Total Dose} = c_{p_s}(T_m - T_i) + \Delta H_m + c_{p_s}(T_f - T_m)$$

where $c_{p_s}$ (=2 J/g/° C.) and $c_{p_s}$ (=3 J/g/° C.) are heat capacities of UHMWPE in the solid state and melt state, respectively, $\Delta H_m$ (=146 J/g) is the heat of melting of the unirradiated Hoescht Celanese CUR 415 bar stock, $T_i$ is the initial temperature, and $T_f$ is the final temperature. The final temperature should be above the melting temperature of the UHMWPE.

Preferably, the final temperature of the UHMWPE is about 140° C. to about 200° C., more preferably it is about 145° C. to about 190° C., more preferably yet it is about 146° C. to about 190° C., and most preferably it is about 150° C. At above 160° C., the polymer starts to form bubbles and cracks. Preferably, the dose rate of the electron irradiation is about 2 to about 3,000 Mrad/minute, more preferably yet is about 2 to about 30 Mrad/minute, more preferably yet is about 7 to about 25 Mrad/minute, more preferably yet is about 20 Mrad/minute, and most preferably is about 7 Mrad/minute. Preferably, the total absorbed dose is about 1 to about 100 Mrad. Using the above equation, the absorbed dose for an initial temperature of 130° C. and a final temperature of 150° C. is calculated to be about 22 Mrad.

In this embodiment, the heating step of the method results from the adiabatic heating described above.

In certain embodiments, the adiabatic heating completely melts the UHMWPE. In certain embodiments, the adiabatic heating only partially melts the UHMWPE. Preferably, additional heating of the irradiated UHMWPE is done subsequent to the irradiation induced adiabatic heating so that the final temperature of the UHMWPE after the additional heating is above the melting temperature of the UHMWPE, so as to ensure complete melting of the UHMWPE. Preferably, the temperature of the UHMWPE from the additional heating is about 140° C. to about 200° C., more preferably is about 145° C. to about 190° C., more preferably yet is about 146° C. to about 190° C., and most preferably is about 150° C.

Yet another embodiment of this invention is called CIR-AM, i.e., cold irradiation and adiabatic heating. In this embodiment, UHMWPE at room temperature or below room temperature is melted by adiabatic heating, with or without subsequent additional heating, as described above.

This invention also includes the product made in accordance with the above described method.

Also provided in this invention is a method of making a medical prosthesis from UHMWPE having substantially no detectable free radicals, the prosthesis resulting in the reduced production of particles from the prosthesis during wear of the prosthesis. Radiation treated UHMWPE having no detectable free radicals is provided. A medical prosthesis is formed from this UHMWPE so as to reduce production of particles from the prosthesis during wear of the prosthesis, the UHMWPE forming a load bearing surface of the prosthesis. Formation of the prosthesis can be accomplished by standard procedures known to those skilled in the art, e.g., machining.

Also provided in this invention is a method of treating a body in need of a medical prosthesis. A shaped prosthesis formed of radiation treated UHMWPE having substantially no detectable free radicals is provided. This prosthesis is applied to the body in need of the prosthesis. The prosthesis reduces production of fine particles from the prosthesis during wear of the prosthesis. In preferred embodiments, the ultra high molecular weight polyethylene forms a load bearing surface of the prosthesis.

In yet another embodiment of this invention, a medical prosthesis for use within the body which is formed of ultra high molecular weight polyethylene (UHMWPE) which has a polymeric structure with less than about 50% crystallinity, less than about 290 Å lamellar thickness and less than about 940 MPa tensile elastic modulus, so as to reduce production of fine particles from the prosthesis during wear of the prosthesis, is provided.

The UHMWPE of this embodiment has a polymeric structure with less than about 50% crystallinity, preferably less than about 40% crystallinity. By crystallinity is meant the fraction of the polymer that is crystalline. The crystallinity is calculated by knowing the weight of the sample (w, in g), the heat absorbed by the sample in melting (E, in cal) and the calculated heat of melting of polyethylene in the 100% crystalline state ($\Delta H°=69.2$ cal/g), and using the following equation:

$$\% \text{ crystallinity} = \frac{E}{w \cdot \Delta H°}$$

The UHMWPE of this embodiment has a polymeric structure with less than about 290 Å lamellar thickness, preferably less than about 200 Å lamellar thickness, and most preferably less than about 100 Å lamellar thickness. By lamellar thickness (l) is meant the calculated thickness of assumed lamellar structures in the polymer using the following expression:

$$l = \frac{2 \cdot \sigma_e \cdot T_m°}{\Delta H° \cdot (T_m° - T_m) \cdot \rho}$$

where, $\sigma_e$ is the end free surface energy of polyethylene ($2.22 \times 10^{-6}$ cal/cm$^2$), $\Delta H°$ is the calculated heat of melting of polyethylene in the 100% crystalline state (69.2 cal/g), $\rho$ is the density of the crystalline regions (1.005 g/cm$^3$), $T_m°$ is the melting point of a perfect polyethylene crystal (418.15K) and $T_m$ is the experimentally determined melting point of the sample.

The UHMWPE of this embodiment has less than about 940 MPa tensile elastic modulus, preferably less than about 600 MPa tensile elastic modulus, more preferably less than about 400 MPa tensile elastic modulus, and most preferably less than about 200 MPa tensile elastic modulus. By tensile elastic modulus is meant the ratio of the nominal stress to corresponding strain for strains less than 0.5% as determined using the standard test ASTM 638 M III.

Preferably, the UHMWPE of this embodiment has a polymeric structure with about 40% crystallinity, about 100 Å lamellar thickness and about 200 MPa tensile elastic modulus.

The UHMWPE of this embodiment has no trapped free radicals, e.g., unsaturated trans-vinylene free radicals. It is preferred that the UHMWPE of this embodiment have a hardness less than about 65 on the Shore D scale, more preferably a hardness less than about 55 on the Shore D scale, most preferably a hardness less than about 50 on the Shore D scale. By hardness is meant the instantaneous indentation hardness measured on the Shore D scale using a durometer described in ASTM D2240. It is preferred that the UHMWPE of this embodiment be substantially not oxidized. The polymeric structure has extensive cross-linking such that a substantial portion of the polymeric structure does not dissolve in Decalin. By substantial portion is meant at least 50% of the polymer sample's dry weight. By not dissolve in Decalin is meant does not dissolve in Decalin at 150° C. over a period of 24 hours. Preferably, The UHMWPE of this embodiment has a high density of entanglement so as to cause the formation of imperfect crystals and reduce crystallinity. By the density of entanglement is meant the number of points of entanglement of polymer chains in a unit volume; a higher density of entanglement being indicated by the polymer sample's inability to crystallize to the same extent as conventional UHMWPE, thus leading to a lesser degree of crystallinity.

The invention also includes other fabricated articles made from the UHMWPE of this embodiment having a polymeric structure with less than about 50% crystallinity, less than about 290 Å lamellar thickness and less than about 940 MPa tensile elastic modulus. Such articles include shaped articles and unshaped articles, including, e.g., machined objects, e.g., cups, gears, nuts, sled runners, bolts, fasteners, cables, pipes and the like, and bar stock, films, cylindrical bars, sheeting, panels, and fibers Shaped articles can be made, e.g., by machining. The fabricated articles are particularly suitable for load bearing applications, e.g., as a load bearing surface, and as metal replacement articles. Thin films or sheets of UHMWPE, which have been melt-irradiated can also be attached, e.g., with glue, onto supporting surfaces, and thus used as a transparent, wear resistant load bearing surface.

The invention also includes an embodiment in which UHMWPE has a unique polymeric structure characterized by less than about 50% crystallinity, less than about 290 Å lamellar thickness and less than about 940 MPa tensile elastic modulus. Depending upon the particular processing used to make the UHMWPE, certain impurities may be present in the UHMWPE of this invention, including, e.g., calcium stearate, mold release agents, extenders, anti-oxidants and/or other conventional additives to polyethylene polymers. In certain embodiments, the UHMWPE has high transmissivity of light, preferably a transmission greater than about 10% of light at 517 nm through a 1 mm thick sample, more preferably a transmission greater than about 30% of light at 517 nm through a 1 mm thick sample, and most preferably a transmission greater than about 40% of light at 517 nm through a 1 mm thick sample. Such UHMWPE is particularly useful for thin films or sheets which can be attached onto supporting surfaces of various articles, the film or sheet being transparent and wear resistant.

In another embodiment of this invention, a method for making crosslinked UHMWPE is provided. This method is called melt irradiation (MIR). Conventional UHMWPE is provided. Preferably, the UHMWPE is surrounded with an inert material that is substantially free of oxygen. The UHMWPE is heated above the melting temperature of the UHMWPE so as to completely melt all crystalline structure. The heated UHMWPE is irradiated, and the irradiated UHMWPE is cooled to about 25° C.

Preferably, the UHMWPE made from this embodiment has a polymeric structure with less than about 50% crystallinity, less than about 290 Å lamellar thickness and less than about 940 MPa tensile elastic modulus. Conventional UHMWPE, e.g., a bar stock, a shaped bar stock, a coating, or a fabricated article is provided. By conventional UHMWPE is meant commercially available high density (linear) polyethylene of molecular weights greater than about 500,000. Preferably, the UHMWPE starting material has an average molecular weight of greater than about 2 million. By initial average molecular weight is meant the average molecular weight of the UHMWPE starting material, prior to any irradiation. It is preferred that this UHMWPE is surrounded with an inert material that is substantially free of oxygen, e.g., nitrogen, argon or helium. In certain embodiments, a non-inert environment can be used. The UHMWPE is heated above its melting temperature for a time sufficient to allow all the crystals to melt. Preferably, the temperature is about 145° C. to about 230° C., and more preferably, is about 175° to about 200° C. Preferably, the heating is maintained so to keep the polymer at the preferred temperature for about 5 minutes to about 3 hours, and more preferably for about 30 minutes to about 2 hours. The UHMWPE is then irradiated with gamma irradiation or electron irradiation. In general, gamma irradiation gives a high penetration depth but takes a longer time, resulting in the possibility of some oxidation. In general, electron irradiation gives more limited penetration depths but takes a shorter time, and hence the possibility of oxidation is reduced. The irradiation dose can be varied to control the degree of crosslinking and crystallinity in the final UHMWPE product. Preferably, a dose of greater than about 1 Mrad is used, more preferably a dose of greater than about 20 Mrad is used. When electron irradiation is used, the energy of the electrons can be varied to change the depth of penetration of the electrons, thereby controlling the degree of crosslinking and crystallinity in the final UHMWPE product. Preferably, the energy is about 0.5 MeV to about 12 MeV, more preferably about 1 MeV to about 10 MeV, and most preferably about 10 MeV. Such manipulability is particularly useful when the irradiated object is an article of varying thickness or depth, e.g., an articular cup for a prosthesis. The irradiated UHMWPE is then cooled to about 25° C. Preferably, the cooling rate is equal to or greater than about 0.5° C./min, more preferably equal to or greater than about 20° C./min. In certain embodiments, the cooled UHMWPE can be machined. In preferred embodiments, the cooled irradiated UHMWPE has substantially no detectable free radicals. Examples 1, 3 and 6 describe certain preferred embodiments of the method. Examples 2, 4 and 5, and FIGS. 4 through 7, illustrate certain properties of the melt-irradiated UHMWPE obtained from these preferred embodiments, as compared to conventional UHMWPE.

This invention also includes the product made in accordance with the above described method.

In an embodiment of MIR, highly entangled and crosslinked UHMWPE is made. Conventional UHMWPE is provided. Preferably, the UHMWPE is surrounded with an inert material that is substantially free of oxygen. The UHMWPE is heated above the melting temperature of the UHMWPE for a time sufficient to enable the formation of entangled polymer chains in the UHMWPE. The heated UHMWPE is irradiated so as to trap the polymer chains in the entangled state. The irradiated UHMWPE is cooled to about 25° C.

This invention also includes the product made in accordance with the above described method.

Also provided in this invention is a method of making a prosthesis from UHMWPE so as to reduce production of fine particles from the prosthesis during wear of the prosthesis. UHMWPE having a polymeric structure with less than about 50% crystallinity, less than about 290 Å lamellar thickness and less than about 940 MPa tensile elastic modulus is provided. A prosthesis is formed from this UHMWPE, the UHMWPE forming a load bearing surface of the prosthesis. Formation of the prosthesis can be accomplished by standard procedures known to those skilled in the art, e.g., machining.

Also provided in this invention is a method of treating a body in need of a prosthesis. A shaped prosthesis formed of ultra high molecular weight polyethylene having a polymeric structure with less than about 50% crystallinity, less than about 290 Å lamellar thickness and less than about 940 MPa tensile elastic modulus, is provided. This prosthesis is applied to the body in need of the prosthesis. The prosthesis reduces production of fine particles from the prosthesis during wear of the prosthesis. In preferred embodiments, the ultra high molecular weight polyethylene forms a load bearing surface of the prosthesis.

The products and processes of this invention also apply to other polymeric materials such as high-density-polyethylene, low-density-polyethylene, linear-low-density-polyethylene and polypropylene.

The following non-limiting examples further illustrate the present invention.

EXAMPLES

Example 1

Method of Making Melt-Irradiated UHMWPE (MIR)

This example illustrates electron irradiation of melted UHMWPE.

A cuboidal specimen (puck) of size 10 mm×12 mm×60 mm, prepared from conventional ram extruded UHMWPE bar stock (Hoescht Celanese GUR 415 bar stock obtained from Westlake Plastics, Lenni, Pa.) was placed in a chamber. The atmosphere within the chamber consisted of low oxygen nitrogen gas (<0.5 µm oxygen gas) (obtained from AIRCO, Murray Hill, N.J.). The pressure in the chamber was approximately 1 atm. The temperature of the sample and the irradiation chamber was controlled using a heater, a variac and a thermocouple readout (manual) or temperature controller (automatic). The chamber was heated with a 270 W heating mantle. The chamber was heated (controlled by the variac) at a rate such that the steady state temperature of the sample was about 175° C. The sample was held at the steady state temperature for 30 minutes before starting the irradiation.

Irradiation was done using a van de Graaff generator with electrons of energy 2.5 MeV and a dose rate of 1.67 MRad/min. The sample was given a dose of 20 MRad with the electron beam hitting the sample on the 60 mm×12 mm surface. The heater was switched off after irradiation, and the sample was allowed to cool within the chamber under inert atmosphere, nitrogen gas, to 25° C. at approximately 0.5° C./minute. As a control, similar specimens were prepared using unheated and unirradiated bar stock of conventional UHMWPE.

Example 2

Comparison of Properties of GUR 415 UHMWPE Bar Stock and Melt-Irradiated (MIR) GUR 415 UHMWPE Bar Stock (20 MRad)

This example illustrates various properties of the irradiated and unirradiated samples of UHMWPE bar stock (GUR 415) obtained from Example 1. The tested samples were as follows: the test sample was bar stock which was molten and then irradiated while molten; control was bar stock (no heating/melting, no irradiation).

(A) Differential Scanning Calorimetry (DSC)

A Perkin-Elmer DSC7 was used with an ice-water heat sink and a heating and cooling rate of 10° C./minute with a continuous nitrogen purge. The crystallinity of the samples obtained from Example 1 was calculated from the weight of the sample and the heat of melting of polyethylene crystals (69.2 cal/g). The temperature corresponding to the peak of the endotherm was taken as the melting point. The lamellar thickness was calculated by assuming a lamellar crystalline morphology, and knowing $\Delta H°$ the heat of melting of 100% crystalline polyethylene (69.2 cal/g), the melting point of a perfect crystal (418.15 K), the density of the crystalline regions (1.005 g/cm$^3$) and the end free surface energy of polyethylene (2.22×10$^{-6}$ cal/cm$^2$). The results are shown in Table 1 and FIG. 4.

TABLE 1

DSC (10° C./min)

| Property | GUR 415 (unirradiated) 0 MRad | GUR 415 (melt-irradiated) 20 MRad |
|---|---|---|
| Crystallinity (%) | 50.2 | 37.8 |
| Melting Point (C.) | 135.8 | 125.5 |
| Lamellar thickness (Å) | 290 | 137 |

The results indicate that the melt-irradiated sample had a more entangled and less crystalline polymeric structure than the unirradiated sample, as evidenced by lower crystallinity, lower lamellar thickness and lower melting point.

(B) Swell Ratio

The samples were cut into cubes of size 2 mm×2 mm×2 mm and kept submerged in Decalin at 150° C. for a period of 24 hours. An antioxidant (1% N-phenyl-2-naphthylamine) was added to the Decalin to prevent degradation of the sample. The swell ratio and percent extract were calculated by measuring the weight of the sample before the experiment, after swelling for 24 hours and after vacuum drying the swollen sample. The results are shown in Table 2.

TABLE 2

Swelling in Decalin with Antioxidant for 24 hours at 150° C.

| Property | GUR 415 (unirradiated) 0 MRad | GUR 415 (melt-irradiated) 20 MRad |
|---|---|---|
| Swell Ratio | dissolves | 2.5 |
| Extract (%) | approx. 100% | 0.0 |

The results indicate that the melt-irradiated UHMWPE sample was highly crosslinked, and hence did not allow dissolution of polymer chains into the hot solvent even after 24 hours, while the unirradiated sample dissolved completely in the hot solvent in the same period.

(C) Tensile Elastic Modulus

ASTM 638 M III of the samples was followed. The displacement rate was 1 mm/minute. The experiment was performed on a MTS machine. The results are shown in Table 3.

TABLE 3

Elastic Test (ASTM 638 M III, 1 mm/min.

| Property | GUR 415 (unirradiated) 0 MRad | GUR 415 (melt-irradiated) 20 MRad |
|---|---|---|
| Tensile Elastic modulus (MPa) | 940.7 | 200.8 |
| Yield stress | 22.7 | 14.4 |
| Strain at break (%) | 953.8 | 547.2 |
| Engineering UTS (MPa) | 46.4 | 15.4 |

The results indicate that the melt-irradiated UHMWPE sample had a significantly lower tensile elastic modulus than the unirradiated control The lower strain at break of the melt-irradiated UHMWPE sample is yet further evidence for the crosslinking of chains in that sample.

(D) Hardness

The hardness of the samples was measured using a durometer on the shore D scale. The hardness was recorded for instantaneous indentation. The results are shown in Table 4.

TABLE 4

Hardness (Shore D)

| Property | GUR 415 (unirradiated) 0 MRad | GUR 415 (melt-irradiated) 20 MRad |
|---|---|---|
| Hardness (D Scale) | 65.5 | 54.5 |

The results indicate that the melt-irradiated UHMWPE was softer than the unirradiated control.

(E) Light Transmissivity (Transparency)

Transparency of the samples was measured as follows: Light transmission was studied for a light of wave length 517 nm passing through a sample of approximately 1 mm in thickness placed between two glass slides. The samples were prepared by polishing the surfaces against 600 grit paper. Silicone oil was spread on the surfaces of the sample and then the sample was placed in between two slides. The silicone oil was used in order to reduce diffuse light scattering due to the surface roughness of the polymer sample. The reference used for this purpose was two similar glass slides separated by a thin film of silicone oil. The transmissivity was measured using a Perkin Elmer Lambda 3B uv-vis spectrophotometer. The absorption coefficient and transmissivity of a sample exactly 1 mm thick were calculated using the Lambert-Beer law. The results are shown in Table 5.

TABLE 5

Transmissivity of Light at 517 nm

| Property | GUR 415 (unirradiated) 0 MRad | GUR 415 (melt-irradiated) 20 MRad |
|---|---|---|
| Transmission (%) (1 mm sample) | 8.59 | 39.9 |
| Absorption coefficient (cm$^1$) | 24.54 | 9.18 |

The results indicate that the melt-irradiated UHMWPE sample transmitted much more light through it than the control, and hence is much more transparent than the control.

(F) Environmental Scanning Electron Microscopy (ESEM)

ESEM (ElectroScan, Model 3) was performed on the samples at 10 kV (low voltage to reduce radiation damage to the sample) with an extremely thin gold coating (approximately 20 Å to enhance picture quality). By studying the surface of the polymer under the ESEM with and without the gold coating, it was verified that the thin gold coating did not produce any artifacts.

The samples were etched using a permanganate etch with a 1:1 sulfuric acid to orthophosphoric acid ratio and a 0.7% (w/v) concentration of potassium permanganate before being viewed under the ESEM.

Figure 4:
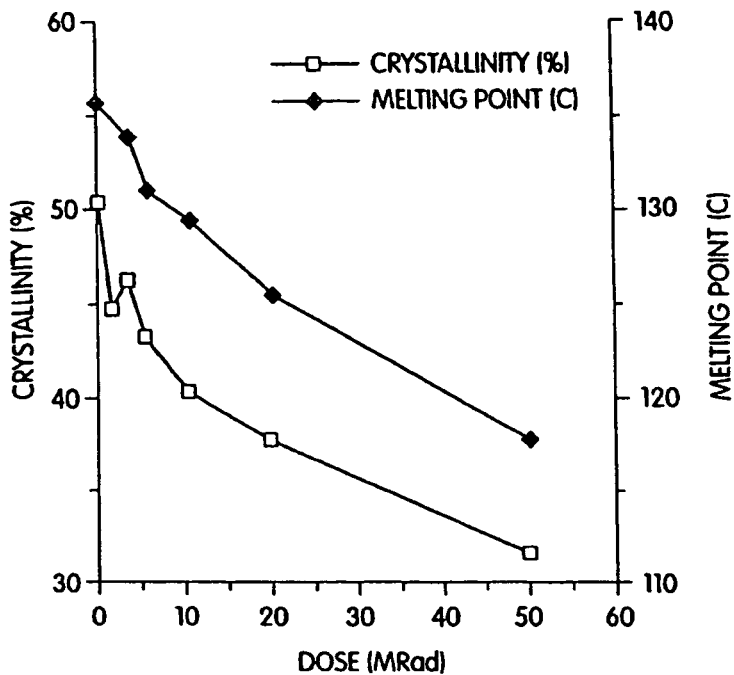
FIG. 4 is a graph showing the crystallinity and melting point of melt-irradiated UHMWPE at different irradiation doses.
Figure 5:
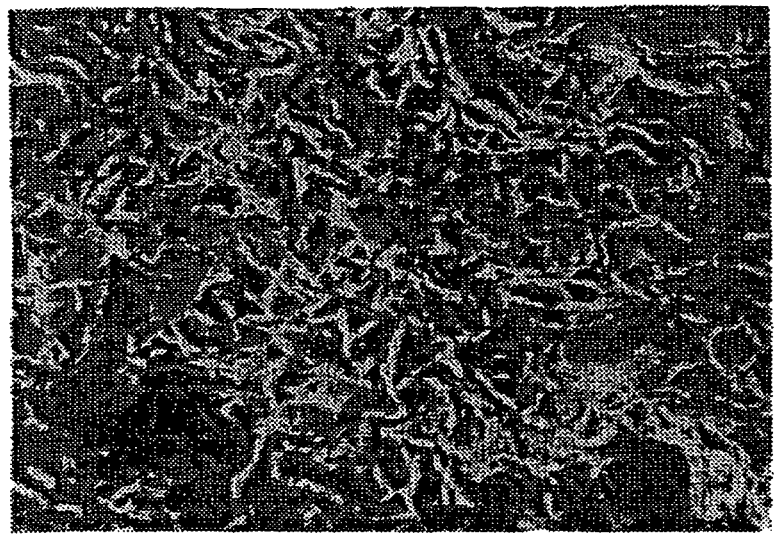
FIG. 5 is an environmental scanning electron micrograph of an etched surface of conventional UHMWPE showing its crystalline structure.
Figure 6:
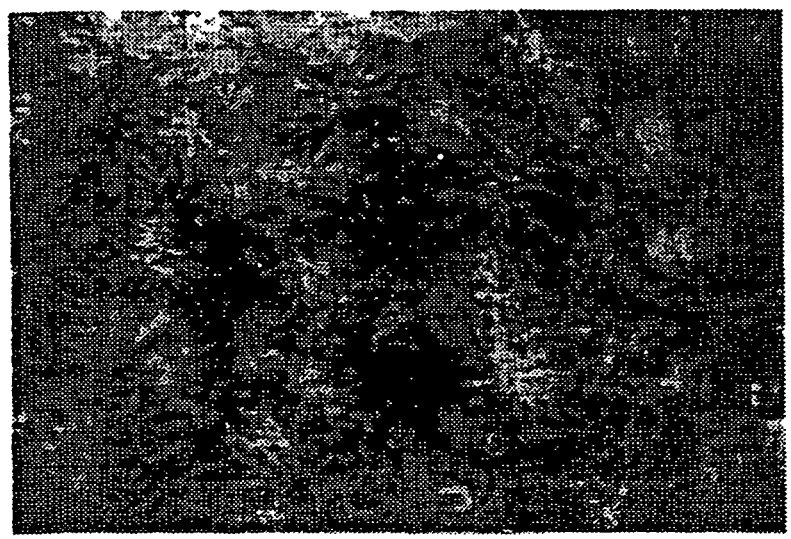
FIG. 6 is an environmental scanning electron micrograph of an etched surface of melt-irradiated UHMWPE showing its crystalline structure at approximately the same magnification as in FIG. 5.

FIG. 4 shows an ESEM (magnification of 10,000×) of an etched surface of conventional UHMWPE (GUR 415; unheated; unirradiated). FIG. 5 shows an ESEM (magnification of 10,500×) of an etched surface of melt-irradiated UHMWPE (GUR 415; melted; 20 MRad). The ESEMs indicated a reduction in size of the crystallites and the occurrence of imperfect crystallization in the melt-irradiated UHMWPE as compared to the conventional UHMWPE.

(G) Fourier Transform Infra Red Spectroscopy (FTIR)

FTIR of the samples was performed using a microsampler on the samples rinsed with hexane to remove surface impurities. The peaks observed around 1740 to 1700 cm$^{-1}$ are bands associated with oxygen containing groups. Hence, the ratio of the area under the carbonyl peak at 1740 cm$^{-1}$ to the area under the methylene peak at 1460 cm$^{-1}$ is a measure of the degree of oxidation.

The FTIR spectra indicate that the melt-irradiated UHMWPE sample showed more oxidation than the conventional unirradiated UHMWPE control, but a lot less oxidation than an UHMWPE sample irradiated in air at room temperature and given the same irradiation dose as the melt-irradiated sample.

(H) Electron Paramagnetic Resonance (EPR)

EPR was performed at room temperature on the samples which were placed in a nitrogen atmosphere in an air tight quartz tube. The instrument used was the Bruker ESP 300 EPR spectrometer and the tubes used were Taperlok EPR sample tubes obtained from Wilmad Glass Company, Buena, N.J.

The unirradiated samples do not have any free radicals in them since irradiation is the process which creates free radicals in the polymer. On irradiation, free radicals are created which can last for several years under the appropriate conditions.

The EPR results indicate that the melt-irradiated sample did not show any free radicals when studied using an EPR immediately after irradiation, whereas the sample which was irradiated at room temperature under nitrogen atmosphere showed trans-vinylene free radicals even after 266 days of storage at room temperature. The absence of free radicals in the melt-irradiated UHMWPE sample means that any further oxidative degradation was not possible.

(I) Wear

The wear resistance of the samples was measured using a bi-axial pin-on-disk wear tester. The wear test involved the rubbing action of UHMWPE pins (diameter=9 mm; height=13 mm) against a Co—Cr alloy disk. These tests were carried out to a total of 2 million cycles. The unirradiated pin displayed a wear rate of 8 mg/million-cycles while the irradiated pin had a wear rate of 0.5 mg/million cycles. The results indicate that the melt-irradiated UHMWPE has far superior wear resistance than the unirradiated control.

Example 3

Method of Making Melt-Irradiated (MIR) UHMWPE Conventional Articular Cups

This example illustrates electron irradiation of a melted UHMWPE conventional articular cup.

A conventional articular cup (high conformity unsterilized UHMWPE cup made by Zimmer, Inc., Warsaw, Ind.) of internal diameter 26 mm and made of GUR 415 ram extruded bar stock, was irradiated under controlled atmosphere and temperature conditions in an air-tight chamber with a titanium cup holder at the base and a thin stainless steel foil (0.001 inches thick) at the top. The atmosphere within this chamber consisted of low oxygen nitrogen gas (<0.5 ppm oxygen gas) (obtained from AIRCO, Murray Hill, N.H.). The pressure in the chamber was approximately 1 atm. The chamber was heated using a 270 W heating mantle at the base of the chamber which was controlled using a temperature controller and a variac. The chamber was heated such that the temperature at the top surface of the cup rose at approximately 1.5° to 2° C./min, finally asymptotically reaching a steady state temperature of approximately 175° C. Due to the thickness of the sample cup and the particular design of the equipment used, the steady state temperature of the cup varied between 200° C. at the base to 175° C. at the top. The cup was held at these temperatures for a period of 30 minutes before starting the irradiation.

Irradiation was done using a van de Graaff generator with electrons of energy 2.5 MeV and a dose rate of 1.67 MRad/min. The beam entered the chamber through the thin foil at top and hit the concave surface of the cup. The dose received by the cup was such that a maximum dose of 20 MRad was received approximately 5 mm below the surface of the cup being hit by the electrons. After irradiation, the heating was stopped and the cup was allowed to cool to room temperature (approximately 25° C.) while still in the chamber with nitrogen gas. The rate of cooling was approximately 0.5° C./min. The sample was removed from the chamber after the chamber and the sample had reached room temperature.

The above irradiated cup which increases in volume (due to the decrease in density accompanying the reduction of crystallinity following melt-irradiation) can be remachined to the appropriate dimensions.

Example 4

Swell Ratio and Percent Extract at Different Depths for Melt-Irradiated (MIR) UHMWPE Articular Cups This example illustrates the swell ratio and percent extract at different depths of the melt-irradiated articular cup obtained from Example 3. Samples of size 2 mm×2 mm×2 mm were cut from the cup at various depths along the axis of the cup. These samples were then kept submerged in Decalin at 150° C. for a period of 24 hours. An antioxidant (1% N-phenyl-2-naphthylamine) was added to the Decalin to prevent degradation of the sample. The swell ratio and percent extract were calculated by measuring the weight of the sample before the experiment, after swelling for 24 hours, and after vacuum drying the swollen sample. The results are shown in Table 6.

TABLE 6

The Swell Ratio and Percent Extract at Different Depths on the Melt-Irradiated UHMWPE Articular Cup

| Depth (mm) | Swell Ratio (Decalin, 150° C., 1 day) | % Extract |
| --- | --- | --- |
| 0–2 | 2.43 | 0.0 |
| 2–4 | 2.52 | 0.0 |
| 4–6 | 2.51 | 0.0 |
| 6–8 | 2.64 | 0.0 |
| 8–10 | 2.49 | 0.0 |
| 10–12 | 3.68 | 0.0 |
| >12 | 6.19 | 35.8 |
| Unirradiated | Dissolves | Approx. 100% |

The results indicate that the UHMWPE in the cup had been crosslinked to a depth of 12 mm due to the melt-irradiation process to such an extent that no polymer chains dissolved out in hot Decalin over 24 hours.

Example 5

Crystallinity and Melting Point at Different Depths for the Melt-Irradiated (MIR) UHMWPE Articular Cups This example illustrates the crystallinity and melting point at different depths of the melt-irradiated cup obtained from Example 3.

Samples were taken from the cup at various depths along the axis of the cup. The crystallinity is the fraction of the polymer that is crystalline. The crystallinity was calculated by knowing the weight of the sample (w, in g), the heat absorbed by the sample in melting (E, in cal which was measured experimentally using a Differential Scanning Calorimeter at 10° C./min) and the heat of melting of polyethylene in the 100% crystalline state ($\Delta H°=69.2$ cal/g), using the following equation:

$$\% \text{ crystallinity} = \frac{E}{w \cdot \Delta H°}$$

Figure 7:
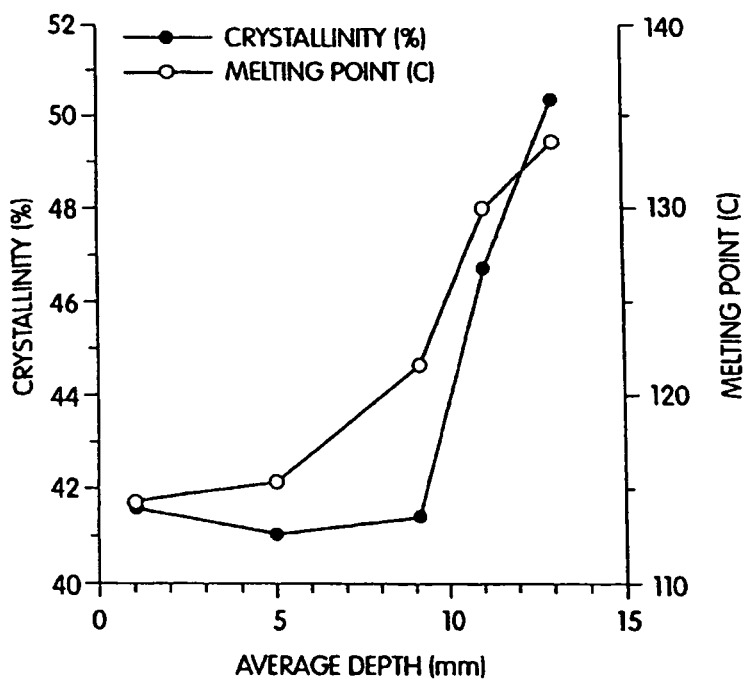
FIG. 7 is a graph showing the crystallinity and melting point at different depths of a melt-irradiated UHMWPE cup.

The melting point is the temperature corresponding to the peak in the DSC endotherm. The results are shown in FIG. 7.

The results indicate that the crystallinity and the melting point of the melt-irradiated UHMWPE in the articular cups obtained from Example 3 were much lower than the corresponding values of the conventional UHMWPE, even to a depth of 1 cm (the thickness of the cup being 1.2 cms).

Example 6

Second Method of Making Melt-Irradiated (MIR) UHMWPE Articular Cups

This example illustrates a method for making articular cups with melt-irradiated UHMWPE.

Conventional ram extruded UHMWPE bar stock (GUR 415 bar stock obtained from West Lake Plastics, Lenni, Pa.) was machined to the shape of a cylinder, of height 4 cm and diameter 5.2 cm. One circular face of the cylinder was machined to include an exact hemispherical hole, of diameter 2.6 cm, such that the axis of the hole and the cylinder coincided. This specimen was enclosed in an air-tight chamber with a thin stainless steel foil (0.001 inches thick) at the top. The cylindrical specimen was placed such that the hemispherical hole faced the foil. The chamber was then flushed and filled with an atmosphere of low oxygen nitrogen gas (<0.5 ppm oxygen gas) obtained from AIRCO, Murray Hill, N.J.). Following this flushing and filling, a slow continuous flow of nitrogen was maintained while keeping the pressure in the chamber at approximately 1 atm. The chamber was heated using a 270 W heating mantle at the base of the chamber which was controlled using a temperature controller and a variac. The chamber was heated such that the temperature at the top surface of the cylindrical specimen rose at approximately 1.5° C. to 2° C./min, finally asymptotically reaching a steady state temperature of approximately 175° C. The specimen was then held at this temperature for a period of 30 minutes before starting irradiation.

Irradiation was done using a van de Graaff generator with electrons of energy 2.5 MeV and a dose rate of 1.67 MRad/min. The beam entered the chamber through the thin foil at top and hit the surface with the hemispherical hole. The dose received by the specimen was such that a maximum dose of 20 MRad was received approximately 5 mm below the surface of the polymer being hit by the electrons. After irradiation, the heating was stopped and the specimen was allowed to cool to room temperature (approximately 25° C.) while still in the chamber with nitrogen gas. The rate of cooling was approximately 0.5° C./min. The sample was removed from the chamber after the chamber and the sample had reached room temperature.

This cylindrical specimen was then machined into an articular cup with the dimensions of a high conformity UHMWPE articular cup of internal diameter 26 mm manufactured by Zimmer, Inc., Warsaw, Ind., such that the concave surface of the hemispherical hole was remachined into the articulating surface. This method allows for the possibility of relatively large changes in dimensions during melt irradiation.

Example 7

Electron Irradiation of UHMWPE Pucks

This example illustrates that electron irradiation of UHMWPE pucks gives a non-uniform absorbed dose profile.

Conventional UHMWPE ram extruded bar stock (Hoescht Celanese GUR 415 bar stock obtained from Westlake Plastics, Lenni, Pa.) was used. The GUR 415 resin used for the bar stock had a molecular weight of 5,000,000 g/mol and contained 500 ppm of calcium stearate. The bar stock was cut into "hockey puck" shaped cylinders (height 4 cm, diameter 8.5 cm).

The pucks were irradiated at room temperature with an electron-beam incident to one of the circular bases of the pucks with a linear electron accelerator operated at 10 MeV and 1 kW (AECL, Pinawa, Manitoba, Canada), with a scan width of 30 cm and a conveyor speed of 0.08 cm/sec. Due to a cascade effect, electron beam irradiation results in a non-uniform absorbed dose profile. Table 7 illustrates the calculated absorbed dose values at various depths in a specimen of polyethylene irradiated with 10 MeV electrons. The absorbed doses were the values measured at the top surface (surface of e-beam incidence).

TABLE 7

The variation of absorbed dose as a function of depth in polyethylene

| Depth (mm) | Absorbed Dose (Mrad) |
|---|---|
| 0 | 20 |
| 0.5 | 22 |
| 1.0 | 23 |
| 1.5 | 24 |
| 2.0 | 25 |
| 2.5 | 27 |
| 3.0 | 26 |
| 3.5 | 23 |
| 4.0 | 20 |
| 4.5 | 8 |
| 5.0 | 3 |
| 5.5 | 1 |
| 6.0 | 0 |

Example 8

Method of Making UHMWPE Using Cold Irradiation and Subsequent Melting (CIR-SM)

This example illustrates a method of making UHMWPE that has a cross-linked structure and has substantially no detectable free radicals, by cold irradiating and then melting the UHMWPE.

Conventional UHMWPE ram extruded bar stock (Hoescht Celanese GUR 415 bar stock obtained from Westlake Plastics, Lenni, Pa.) was used. The GUR 415 resin used for the bar stock had a molecular weight of 5,000,000 g/mol and contained 500 ppm of calcium stearate. The bar stock was cut into "hockey puck" shaped cylinders (height 4 cm, diameter 8.5 cm).

The pucks were irradiated at room temperature at a dose rate of 2.5 Mrad per pass to 2.5, 5, 7.5, 10, 12.5, 15, 17.5, 20, 30, and 50 Mrad total absorbed dose as measured on the top surface (electron-beam incidence) (AECL, Pinawa, Manitoba, Canada). The pucks were not packaged and the irradiation was carried out in air. Subsequent to irradiation, the pucks were heated to 150° C. under vacuum for 2 hours so as to melt the polymer and thereby result in the recombination of free radicals leading to substantially no detectable residual free radicals. The pucks were then cooled to room temperature at a rate of 5° C./min.

The residual free radicals are measured by electron paramagnetic resonance as described in Jahan et al., J. Biomedical Materials Research 25: 1005 (1991).

Example 9

Method of Making UHMWPE Using Warm Irradiation and Subsequent Melting (WIR-SM)

This example illustrates a method of making UHMWPE that has a cross-linked structure and has substantially no detectable free radicals, by irradiating UHMWPE that has been heated to below the melting point, and then melting the UHMWPE.

Conventional UHMWPE ram extruded bar stock (Hoescht Celanese GUR 415 bar stock obtained from Westlake Plastics, Lenni, Pa.) was used. The GUR 415 resin used for the bar stock had a molecular weight of 5,000,000 g/mol and contained 500 ppm of calcium stearate. The bar stock was cut into "hockey puck" shaped cylinders (height 4 cm, diameter 8.5 cm).

The pucks were heated to 100° C. in air in an oven. The heated pucks were then irradiated with an electron beam to a total dose of 20 Mrad at a dose rate of 2.5 Mrad per pass (E-Beam Services, Cranbury, N.J.), with a scan width of 30 cm and a conveyor speed of 0.08 cm/sec. Subsequent to irradiation, the pucks were heated to 150° C. under vacuum for 2 hours, thereby allowing the free radicals to recombine leading to substantially no detectable residual free radicals. The pucks were then cooled to room temperature at a rate of 5° C./min.

Example 10

Method of Making UHMWPE Using Warm Irradiation and Adiabatic Melting (WIR-AM)

This example illustrates a method of making UHMWPE that has a cross-linked structure and has substantially no detectable free radicals, by irradiating UHMWPE that has been heated to below the melting point so as to generate adiabatic melting of the UHMWPE.

Conventional UHMWPE ram extruded bar stock (Hoescht Celanese GUR 415 bar stock obtained from Westlake Plastics, Lenni, Pa.) was used. The GUR 415 resin used for the bar stock had a molecular weight of 5,000,000 g/mol and contained 500 ppm of calcium stearate. The bar stock was cut into "hockey puck" shaped cylinders (height 4 cm, diameter 8.5 cm).

Two pucks were packed in a fiberglass pouch (obtained from Fisher Scientific Co., Pittsburgh, Pa.) to minimize heat loss in subsequent processing steps. First, the wrapped pucks were heated overnight in an air convection oven kept at 120° C. As soon as the pucks were removed from the oven they were placed under an electron-beam incident to one of the circular bases of the pucks from a linear electron accelerator operated at 10 MeV and 1 kW (AECL, Pinawa, Manitoba, Canada), and immediately irradiated to a total dose of 21 and 22.5 Mrad, respectively. The dose rate was 2.7 Mrad/min. Therefore, for 21 Mrad, radiation was for 7.8 min., and for 22.5 Mrad, radiation was for 8.3 min. Following the irradiation, the pucks were cooled to room temperature at a rate of 5° C./minute, at which point the fiberglass pouch was removed and the specimens analyzed.

Example 11

Comparison of Properties of GUR 415 UHMWPE Bar Stock Pucks and CIR-SM and WIR-AM-Treated Bar Stock Pucks This example illustrates various properties of the irradiated and unirradiated samples of UHMWPE bar stock GUR 415 obtained from Examples 8 and 10. The tested samples were as follows: (i) test samples (pucks) from bar stock which was irradiated at room temperature, subsequently heated to about 150° C. for complete melting of polyethylene crystals, followed by cooling to room temperature (CIR-SM), (ii) test samples (pucks) from bar stock which was heated to 120° C. in a fiberglass pouch so as to minimize heat loss from the pucks, followed by immediate irradiation to generate adiabatic melting of the polyethylene crystals (WIR-AM), and (iii) control bar stock (no heating/melting, no irradiation).

A. Fourier Transform Infra-Red Spectroscopy (FTIR)

Infra-red (IR) spectroscopy of the samples was performed using a BioRad UMA 500 infrared microscope on thin sections of the samples obtained from Examples 8 and 10. The thin sections (50 µm) were prepared with a sledge microtome. The IR spectra were collected at 20 µm, 100 µm, and 3 mm below the irradiated surface of the pucks with an aperture size of 10×50 µm$^2$. The peaks observed around 1740 to 1700 cm$^{-1}$ are associated with the oxygen containing groups. Hence, the ratio of the area under the carbonyl peak at 1740 cm$^{-1}$ to the area under the methylene peak at 1460 cm$^{-1}$, after subtracting the corresponding baselines, was a measure of the degree of oxidation. Tables 8 and 9 summarize the degree of oxidation for the specimens described in Examples 8 and 10.

These data show that following the cross-linking procedures there was some oxidation within a thin layer of about 100 µm thickness. Upon machining this layer away, the final product would have the same oxidation levels as the unirradiated control.

TABLE 8

Degree of oxidation of specimens from Example 8
(CIR-SM) (with post-irradiation melting in vacuum)

| Specimen | Oxidation Degree at various depths (A.U.) | | |
|---|---|---|---|
| | 20 µm | 100 µm | 3 mm |
| Unirradiated Control | 0.01 | 0.01 | 0.02 |
| Irradiated to 2.5 Mrad | 0.04 | 0.03 | 0.03 |
| Irradiated to 5 Mrad | 0.04 | 0.03 | 0.01 |
| Irradiated to 7.5 Mrad | 0.05 | 0.02 | 0.02 |

TABLE 8-continued

Degree of oxidation of specimens from Example 8
(CIR-SM) (with post-irradiation melting in vacuum)

| Specimen | Oxidation Degree at various depths (A.U.) | | |
| --- | --- | --- | --- |
| | 20 μm | 100 μm | 3 mm |
| Irradiated to 10 Mrad | 0.02 | 0.03 | 0.01 |
| Irradiated to 12.5 Mrad | 0.04 | 0.03 | 0.01 |
| Irradiated to 15 Mrad | 0.03 | 0.01 | 0.02 |
| Irradiated to 17.5 Mrad | 0.07 | 0.05 | 0.02 |
| Irradiated to 20 Mrad | 0.03 | 0.02 | 0.01 |

TABLE 9

Degree of oxidation of specimens from Example 10
(WIR-AM)

| Specimen | Oxidation Degree at (A.U.) | | |
| --- | --- | --- | --- |
| | 20 μm | 100 μm | 3 mm |
| Unirradiated Control | 0.01 | 0.01 | 0.02 |
| Irradiated to 21 Mrad | 0.02 | 0.01 | 0.03 |
| Irradiated to 22.5 Mrad | 0.02 | 0.02 | 0.01 |

B. Differential Scanning Calorimetry (DSC)

A Perkin-Elmer DSC7 was used with an ice-water heat sink and a heating and cooling rate of 10° C./minute with a continuous nitrogen purge. The crystallinity of the specimens obtained from Examples 8 and 10 was calculated from the weight of the sample and the heat of melting of polyethylene crystals measured during the first heating cycle. The percent crystallinity is given by the following equation:

$$\% \text{ crystallinity} = \frac{E}{w \cdot \Delta H°}$$

where E and w are the heat of melting (J or cal) and weight (grams) of the specimen tested, respectively, and $\Delta H°$ is the heat of melting of 100% crystalline polyethylene in Joules/gram (291 J/g or 69.2 cal/g). The temperature corresponding to the peak of the endotherm was taken as the melting point. In some cases where there were multiple endotherm peaks, multiple melting points corresponding to these endotherm peaks have been reported. The crystallinities and melting points for the specimens described in Examples 8 and 10 are reported in Tables 10 and 11.

TABLE 10

DSC at a heating rate of 10° C./min for specimens of
Example 8 (CIR-SM)

| Specimen | Crystallinity(%) | Melting Point(° C.) |
| --- | --- | --- |
| Unirradiated Control | 59 | 137 |
| Irradiated to 2.5 Mrad | 54 | 137 |
| Irradiated to 5 Mrad | 53 | 137 |
| Irradiated to 10 Mrad | 54 | 137 |
| Irradiated to 20 Mrad | 51 | 137 |
| Irradiated to 30 Mrad | 37 | 137 |

TABLE 11

DSC at a heating rate of 10° C./min for specimens of
Example 10 (WIR-AM)

| Specimen | Crystallinity(%) | Melting Point(° C.) |
| --- | --- | --- |
| Unirradiated Control | 59 | 137 |
| Irradiated to 21 Mrad | 54 | 120–135–145 |
| Irradiated to 22.5 Mrad | 48 | 120–135–145 |

The data shows that the crystallinity does not change significantly up to absorbed doses of 20 Mrad. Therefore, the elastic properties of the cross-linked material should remain substantially unchanged upon cross-linking. On the other hand, one could tailor the elastic properties by changing the crystallinity with higher doses. The data also shows that the WIR-AM material exhibited three melting peaks.

C. Pin-on-Disc Experiments for Wear Rate

The pin-on-disc (POD) experiments were carried out on a bi-axial pin-on-disc tester at a frequency of 2 Hz where polymeric pins were tested by a rubbing action of the pin against a highly polished Co—Cr disc. Prior to preparing cylindrical shaped pins (height 13 mm, diameter 9 mm), one millimeter from the surface of the pucks was machined away in order to remove the outer layer that had been oxidized during irradiation and post- and pre-processing. The pins were then machined from the core of the pucks and tested on the POD such that the surface of e-beam incidence was facing the Co—Cr disc. The wear tests were carried out to a total of 2,000,000 cycles in bovine serum. The pins were weighed at every 500,000 cycle and the average values of weight loss (wear rate) are reported in Tables 12 and 13 for specimens obtained from Examples 0 and 10 respectively.

TABLE 12

POD wear rates for specimens of Example 8 (CIR-SM)

| Specimen | Wear Rate (mg/million cycle) |
| --- | --- |
| Unirradiated Control | 9.78 |
| Irradiated to 2.5 Mrad | 9.07 |
| Irradiated to 5 Mrad | 4.80 |
| Irradiated to 7.5 Mrad | 2.53 |
| Irradiated to 10 Mrad | 1.54 |
| Irradiated to 15 Mrad | 0.51 |
| Irradiated to 20 Mrad | 0.05 |
| Irradiated to 30 Mrad | 0.11 |

TABLE 13

POD wear rates for specimens of Example 10
(WIR-AM)

| Specimen | Wear Rate (mg/million cycle) |
| --- | --- |
| Unirradiated Control | 9.78 |
| Irradiated to 21 Mrad | 1.15 |

The results indicate that the cross-linked UHMWPE has far superior wear resistance than the unirradiated control.

D. Gel Content and Swell Ratio

The samples were cut in cubes of size $2 \times 2 \times 2$ mm$^3$ and kept submerged in xylene at 130° C. for a period of 24 hours. An antioxidant (1% N-phenyl-2-naphthylamine) was added to the xylene to prevent degradation of the sample. The swell ratio and gel content were calculated by measuring the weight of the sample before the experiment, after swelling for 24 hours and after vacuum drying the swollen sample. The results are shown in Tables 14 and 15 for the specimens obtained from Examples 8 and 10.

TABLE 14

Gel content and swell ratio for specimens of Example 8 (CIR-SM)

| Specimen | Gel Content(%) | Swell Ratio |
|---|---|---|
| Unirradiated Control | 89.7 | 12.25 |
| Irradiated to 5 Mrad | 99.2 | 4.64 |
| Irradiated to 10 Mrad | 99.9 | 2.48 |
| Irradiated to 20 Mrad | 99.0 | 2.12 |
| Irradiated to 30 Mrad | 99.9 | 2.06 |

TABLE 15

Gel content and swell ratio for specimens of Example 10 (WIR-AM)

| Specimen | Gel Content(%) | Swell Ratio |
|---|---|---|
| Unirradiated Control | 89.7 | 12.25 |
| Irradiated to 21 Mrad | 99.9 | 2.84 |
| Irradiated to 22.5 Mrad | 100 | 2.36 |

The results show that the swell ratio decreased with increasing absorbed dose indicating an increase in the cross-link density. The gel content increased indicating the formation of a cross-linked structure.

Example 12

Free Radical Concentration for UHMWPE Prepared by Cold Irradiation With and Without Subsequent Melting (CIR-SM)

This example illustrates the effect of melting subsequent to cold irradiation of UHMWPE on the free radical concentration. Electron paramagnetic resonance (EPR) was performed at room temperature on the samples after placing in a nitrogen atmosphere in an air tight quartz tube. The instrument used was the Bruker ESP 300 EPR spectrometer and the tubes used were Taperlok EPR sample tubes (obtained from Wilmad Glass Co., Buena, N.J.).

The unirradiated samples did not have any detectable free radicals in them. During the process of irradiation, free radicals are created which can last for at least several years under the appropriate conditions.

The cold-irradiated UHMWPE specimens exhibited a strong free radical signal when tested with the EPR technique. When the same samples were examined with EPR following a melting cycle, the EPR signal was found to be reduced to undetectable levels. The absence of free radicals in the cold irradiated subsequently melted (recrystallized) UHMWPE sample means that any further oxidative degradation cannot occur via attack on entrapped radicals.

Example 13

Crystallinity and Melting Point at Different Depths for UHMWPE Prepared by Cold Irradiation and Subsequent Melting (CIR-SM)

This example illustrates the crystallinity and melting point at different depths of the cross-linked UHMWPE specimens obtained from Example 8 with 20 Mrad total radiation dose. Samples were taken at various depths from the cross-linked specimen. The crystallinity and the melting point were determined using a Perkin Elmer differential scanning calorimeter as described in Example 10(B). The results are shown in Table 16.

TABLE 16

DSC at a heating rate of 10° C./min for specimen of Example 8 irradiated to a total dose of 20 Mrad (CIR-SM)

| Depth (mm) | Crystallinity(%) | Melting Point(° C.) |
|---|---|---|
| 0–2 | 53 | 137 |
| 6–8 | 54 | 137 |
| 9–11 | 54 | 137 |
| 14–16 | 34 | 137 |
| 20–22 | 52 | 137 |
| 26–28 | 56 | 137 |
| 29–31 | 52 | 137 |
| 37–40 | 54 | 137 |
| Unirradiated Control | 59 | 137 |

The results indicate that the crystallinity varied as a function of depth away from the surface. The sudden drop in 16 mm is the consequence of the cascade effect. The peak in the absorbed dose was located around 16 mm where the dose level could be as high as 27 Mrad.

Example 14

Comparison of UHMWPE Prepared by CIR-SM Using Melting in Air Versus Melting Under Vacuum This example illustrates that the oxidation levels of UHMWPE pucks prepared by CIR-SM, whether melted in air or under vacuum, are the same as unirradiated pucks at a depth of 3 mm below the surface of the pucks.

Conventional UHMWPE ram extruded bar stock (Hoescht Celanese GUR 415 bar stock obtained from Westlake Plastics, Lenni, Pa.) was used. The GUR 415 resin used for the bar stock had a molecular weight of 5,000,000 g/mol and contained 500 ppm of calcium stearate. The bar stock was cut into "hockey puck" shaped cylinders (height 4 cm, diameter 8.5 cm).

Two pucks were irradiated at room temperature with a dose rate of 2.5 Mrad per pass to 17.5 Mrad total absorbed dose as measured on the top surface (e-beam incidence) (AECL, Pinawa, Manitoba, Canada), with a scan width of 30 cm and a conveyor speed of 0.07 cm/sec. The pucks were not packaged and the irradiation was carried out in air. Subsequent to irradiation, one puck was heated under vacuum to 150° C. for 2 hours, and the other puck was heated in air to 150° C. for 2 hours, so as to attain a state of no detectable residual crystalline content and no detectable residual free radicals. The pucks were then cooled to room temperature at a rate of 5° C./min. The pucks were then analyzed for the degree of oxidation as described in example 11(A). Table 17 summarizes the results obtained for the degree of oxidation.

TABLE 17

Degree of oxidation of specimens melted in air versus in vacuum

| Specimen | Post-Melting Environment | Oxidation Degree at various depths (A.U.) | | |
|---|---|---|---|---|
| | | 20 μm | 100 μm | 3 mm |
| Unirradiated Control | N/A | 0.01 | 0.01 | 0.02 |
| Irradiated to 17.5 Mrad | Vacuum | 0.07 | 0.05 | 0.02 |
| Irradiated to 17.5 Mrad | Air | 0.15 | 0.10 | 0.01 |

The results indicated that within 3 mm below the free surfaces the oxidation level in the irradiated UHMWPE specimens dropped to oxidation levels observed in unirradiated control UHMWPE. This was the case independent of post-irradiation melting atmosphere (air or vacuum). Therefore, post-irradiation melting could be done in an air convection oven without oxidizing the core of the irradiated puck.

Example 15

Method of Making UHMWPE Using Cold Irradiation and Subsequent Melting Using Gamma Irradiation (CIR-SM)

This example, illustrates a method of making UHMWPE that has a cross-linked structure and has substantially no detectable free radicals, by cold irradiating with gamma-radiation and then melting the UHMWPE.

Conventional UHMWPE ram extruded bar stock (Hoescht Celanese GUR 415 bar stock obtained from Westlake Plastics, Lenni, Pa.) was used. The GUR 415 resin used for the bar stock had a molecular weight of 5,000,000 g/mol and contained 500 ppm of calcium stearate. The bar stock was cut into "hockey puck" shaped cylinders (height 4 cm, diameter 8.5 cm).

The pucks were irradiated at room temperature at a dose rate of 0.05 Mrad/minute to 4 Mrad total absorbed dose as measured on the top surface (gamma ray incidence) (Isomedix, Northboro, Mass.). The pucks were not packaged and irradiation was carried out in air. Subsequent to irradiation, the pucks were heated to 150° C. under vacuum for 2 hours so as to melt the polymer and thereby result in the recombination of free radicals leading to substantially no detectable residual free radicals.

Example 16

I. Method of Making UHMWPE Using Warm Irradiation and Partial Adiabatic Melting with Subsequent Complete Melting (WIR-AM)

This example illustrates a method of making UHMWPE that has a cross-linked structure, exhibits two distinct melting endotherms in a differential scanning calorimeter (DSC), and has substantially no detectable free radicals, by irradiating UHMWPE that has been heated to below the melting point so as to generate adiabatic partial melting of the UHMWPE and by subsequently melting the UHMWPE.

A GUR 4050 bar stock (made from ram extruded Hoescht Celanese GUR 4050 resin obtained from Westlake Plastics, Lenni, Pa.) was machined into 8.5 cm diameter and 4 cm thick hockey pucks. Twenty-five pucks, 25 aluminum holders and 25 20 cm×20 cm fiberglass blankets were preheated to 125° C. overnight in an air convection oven. The preheated pucks were each placed in a preheated aluminum holder which was covered by a preheated fiberglass blanket to minimize heat loss to the surroundings during irradiation. The pucks were then irradiated in air using a 10 MeV, 1 kW electron beam with a scan width of 30 cm (AECL, Pinawa, Manitoba, Canada). The conveyor speed was 0.07 cm/sec which gave a dose rate of 70 kGy per pass. The pucks were irradiated in two passes under the beam to achieve a total absorbed dose of 140 kGy. For the second pass, the conveyor belt motion was reversed as soon as the pucks were out of the electron beam raster area to avoid any heat loss from the pucks. Following the warm irradiation, 15 pucks were heated to 150° C. for 2 hours so as to obtain complete melting of the crystals and substantial elimination of the free radicals.

A. Thermal Properties (DSC) of the specimens prepared in Example 16

A Perkin-Elmer DSC 7 was used with an ice water heat sink and a heating and cooling rate of 10° C./min with a continuous nitrogen purge. The crystallinity of the samples obtained from Example 16 was calculated from the weight of the sample and the heat of melting of polyethylene crystals (69.2 cal/gm). The temperature corresponding to the peak of the endotherm was taken as the melting point. In the case of multiple endotherm peaks, multiple melting points were reported.

Table 18 shows the variations obtained in the melting behavior and crystallinity of the polymer as a function of depth away from the e-beam incidence surface. FIG. 8 shows representative DSC melting endotherms obtained at 2 cm below the surface of e-beam incidence obtained both before and after the subsequent melting.

TABLE 18

WIR-AM GUR 4050 barstock, Total dose = 140 kGy, 75 kGy/pass

| Depth (mm) | T 1st peak after irradiation (° C.) | T 2nd peak after irradiation (° C.) | T 3rd peak after irradiation (° C.) | T 1st peak after subsequent melting (° C.) | T 2nd peak after subsequent melting (° C.) | Crystallinity after irradiation (%) | Crystallinity after subsequent melting (%) |
|---|---|---|---|---|---|---|---|
| 1.77 | 109.70 | NP | 145.10 | 116.35 | 139.45 | 53.11 | 45.26 |
| 5.61 | 118.00 | NP | 147.80 | 117.10 | 141.60 | 52.61 | 45.46 |
| 9.31 | 113.00 | NP | 146.40 | 117.30 | 141.10 | 50.13 | 44.42 |

TABLE 18-continued

WIR-AM GUR 4050 barstock, Total dose = 140 kGy, 75 kGy/pass

| Depth (mm) | T 1st peak after irradiation (° C.) | T 2nd peak after irradiation (° C.) | T 3rd peak after irradiation (° C.) | T 1st peak after subsequent melting (° C.) | T 2nd peak after subsequent melting (° C.) | Crystallinity after irradiation (%) | Crystallinity after subsequent melting (%) |
|---|---|---|---|---|---|---|---|
| 13.11 | 113.47 | 138.07 | 145.23 | 116.03 | 139.83 | 47.29 | 43.33 |
| 16.89 | 113.40 | 137.40 | 144.80 | 115.90 | 139.30 | 47.68 | 43.05 |
| 20.95 | 113.70 | 138.33 | 145.17 | 115.17 | 139.63 | 44.99 | 43.41 |
| 24.60 | 112.40 | 134.20 | 143.90 | 114.90 | 138.70 | 49.05 | 44.40 |
| 28.57 | 112.30 | NP | 145.70 | 115.90 | 139.90 | 50.84 | 44.40 |
| 31.89 | 111.20 | NP | 144.50 | 114.90 | 138.80 | 51.88 | 45.28 |
| 34.95 | NP | NP | 143.90 | 112.00 | 138.45 | 50.09 | 45.36 |
| 39.02 | NP | NP | 139.65 | 114.95 | 138.30 | 49.13 | 46.03 |

*NP: The peak is not present

These results indicate that the melting behavior of UHMWPE changes drastically after the subsequent melting step in this embodiment of the WIR-AM process. Before the subsequent melting, the polymer exhibited three melting peaks, while after subsequent melting it exhibited two melting peaks.

B. Electron Paramagnetic Resonance (EPR) of the Specimens Prepared in Example 16

EPR was performed at room temperature on samples obtained from Example 16 after placing the samples in an air tight quartz tube in a nitrogen atmosphere. The instrument used was the Bruker ESP 300 EPR spectrometer and the tubes uses were Taperlok EPR sample tubes (obtained from Wilmad Glass Co., Buena, N.J.).

The unirradiated samples did not have any detectable free radicals in them. During the process of irradiation, free radicals are created which can last for at least several years under the appropriate conditions.

Before the subsequent melting, the EPR results showed a complex free radical peak composed of both peroxy and primary free radicals. After the subsequent melting the EPR free radical signal was reduced to undetectable levels. These results indicated that the free radicals induced by the irradiation process were substantially eliminated after the subsequent melting step. Thus, the UHMWPE was highly resistant to oxidation.

Example 17

II. Method of Making UHMWPE Using Warm Irradiation and Partial Adiabatic Melting with Subsequent Complete Melting (WIR-AM)

This example illustrates a method of making UHMWPE that has a cross-linked structure, exhibits two distinct melting endotherms in DSC, and has substantially no detectable free radicals, by irradiating UHMWPE that has been heated to below the melting point so as to generate the adiabatic partial melting of the UHMWPE and by subsequently melting the UHMWPE.

A CUR 4020 bar stock (made from ram extruded Hoescht Celanese GUR 4020 resin obtained from Westlake Plastics, Lenni, Pa.) was machined into 8.5 cm diameter and 4 cm thick hockey pucks. Twenty-five pucks, 25 aluminum holders and 25 20 cm×20 cm fiberglass blankets were preheated to 125° C. overnight in an air convection oven. The preheated pucks were each placed in a preheated aluminum holder which was covered by a preheated fiberglass blanket to minimize heat loss to the surroundings during irradiation. The pucks were then irradiated in air using a 10 MeV, 1 kW electron beam with a scan width of 30 cm (AECL, Pinawa, Manitoba, Canada). The conveyor speed was 0.07 cm/sec which gave a dose rate of 70 kGy per pass. The pucks were irradiated in two passes under the beam to achieve a total absorbed dose of 140 kGy. For the second pass, the conveyor belt motion was reversed as soon as the pucks were out of the electron beam raster area to avoid any heat loss from the pucks. Following the warm irradiation, 15 pucks were heated to 150° C. for 2 hours so as to obtain complete melting of the crystals and substantial elimination of the free radicals.

Example 18

III. Method of Making UHMWPE Using Warm Irradiation and Partial Adiabatic Melting with Subsequent Complete Melting (WIR-AM)

This example illustrates a method of making UHMWPE that has a cross-linked structure, exhibits two distinct melting endotherms in DSC, and has substantially no detectable free radicals, by irradiating UHMWPE that has been heated to below the melting point so as to generate adiabatic partial melting of the UHMWPE and by subsequently melting the UHMWPE.

A GUR 1050 bar stock (made from ram-extruded Hoescht Celanese GUR 1050 resin obtained from Westlake Plastics, Lenni, Pa.) was machined into 8.5 cm diameter and 4 cm thick hockey pucks. Eighteen pucks, 18 aluminum holders and 18 20 cm×20 cm fiberglass blankets were preheated to 125° C., 90° C., or 70° C., in an air convection oven overnight. Six pucks were used for each different pre-heat temperature. The preheated pucks were each placed in a preheated aluminum holder which was covered by a preheated fiberglass blanket to minimize heat loss to the surroundings during irradiation. The pucks were then irradiated in air using a 10 MeV and 1 kW electron beam with a scan width of 30 cm (AECL, Pinawa, Manitoba, Canada). The conveyer speed was 0.06 cm/sec which gave a dose rate of 75 kGy per pass. The pucks were irradiated in two passes under the beam to accumulate a total of 150 kGy of absorbed dose. For the second pass, the conveyor belt motion was reversed as soon as the pucks were out of the electron beam raster area to avoid any heat loss from the pucks. Following the warm irradiation, half of the pucks were heated to 150° C. for 2 hours so as to obtain complete melting of the crystals and substantial elimination of the free radicals.

A. Thermal Properties of the Specimens Prepared in Example 18

A Perkin-Elmer DSC 7 was used with an ice water heat sink and a heating and cooling rate of 10° C./min with a continuous nitrogen purge. The crystallinity of the samples obtained from Example 18 was calculated from the weight of the sample and the heat of melting of polyethylene crystals (69.2 cal/gm). The temperature corresponding to the peak of the endotherm was taken as the melting point. In the case of multiple endotherm peaks, multiple melting points were reported.

Table 19 shows the effect of pre-heat temperature on the melting behavior and crystallinity of the polymer. FIG. 9 shows the DSC profile of a puck processed with the WIR-AM method at a pre-heat temperature of 125° C. both before and after subsequent melting.

TABLE 19

WIR-AM GUR 1050 barstock, Total dose = 150 kGy, 75 kGy/pass

| Preheat (° C.) | T 1st peak after irradiation (° C.) | T 2nd peak after irradiation (° C.) | T 3rd peak after irradiation (° C.) | T 1st peak after subsequent melting (° C.) | T 2nd peak after subsequent melting (° C.) | Crystallinity after irradiation (%) | Crystallinity after subsequent melting (%) |
|---|---|---|---|---|---|---|---|
| 125 | 114.6 | 135.70 | 143.5 | 114.85 | 135.60 | 42.81 | 40.85 |
| 90  | NP    | 142.85 | NP    | 116.75 | 136.95 | 52.39 | 44.31 |
| 70  | NP    | 141.85 | NP    | NP     | 136.80 | 51.59 | 44.62 |

*NP: The peak is not present

These results indicate that the melting behavior of UHMWPE changes drastically after the subsequent melting step in this embodiment of the WIR-AM process. Before the subsequent melting, the polymer exhibited three melting peaks, while after subsequent melting it exhibited two melting peaks.

Example 19

IV. Method of Making UHMWPE Using Warm Irradiation and Partial Adiabatic Melting with Subsequent Complete Melting (WIR-AM)

This example illustrates a method of making UHMWPE that has a cross-linked structure, exhibits two distinct melting endotherms in DSC, and has substantially no detectable free radicals, by irradiating UHMWPE that has been heated to below the melting point so as to generate adiabatic partial melting of the UHMWPE and by subsequently melting the polymer.

A GUR 1020 bar stock (made from ram extruded Hoescht Celanese GUR 1020 resin obtained from Westlake Plastics, Lenni, Pa.) was machined in 7.5 cm diameter and 4 cm thick hockey pucks. Ten pucks, 10 aluminum holders and 10 20 cm×20 cm fiberglass blankets were preheated to 125° C. overnight in an air convection oven. The preheated pucks were each placed in a preheated aluminum holder which was covered by a preheated fiberglass blanket to minimize heat loss to the surroundings during irradiation. The pucks were then irradiated in air using a 10 MeV, 1 kW linear electron beam accelerator (AECL, Pinawa, Manitoba, Canada). The scan width and the conveyor speed was adjusted to achieve the desired dose rate per pass. The pucks were then irradiated to 61, 70, 80, 100, 140, and 160 kGy of total absorbed dose. For 61, 70, 80 kGy absorbed dose, the irradiation was completed in one pass; while for 100, 140, and 160 it was completed in two passes. For each absorbed dose level, six pucks were irradiated. During the two pass experiments, for the second pass, the conveyor belt motion was reversed as soon as the pucks were out of the electron beam raster area to avoid any heat loss from the pucks. Following the irradiation, half of the pucks were heated to 150° C. for 2 hours in an air convection oven so as to obtain complete melting of the crystals and substantial elimination of the free radicals.

Example 20

V. Method of Making UHMWPE Using Warm Irradiation and Partial Adiabatic Melting with Subsequent Complete Melting (WIR-AM)

This example illustrates a method of making UHMWPE that has a cross-linked structure, exhibits two distinct melting endotherms in DSC, and has substantially no detectable free radicals, by irradiating UHMWPE that has been heated to below the melting point so as to generate adiabatic partial melting of the UHMWPE and by subsequently melting the polymer.

A GUR 4150 bar stock (made from ram extruded Hoescht Celanese GUR 4150 resin obtained from Westlake Plastics, Lenni, Pa.) was machined into 7.5 cm diameter and 4 cm thick hockey pucks. Ten pucks, 10 aluminum holders and 10 20 cm×20 cm fiberglass blankets were preheated to 125° C. overnight in an air convection oven. The preheated pucks were each placed in a preheated aluminum holder which was covered by a preheated fiberglass blanket to minimize heat loss to the surroundings during irradiation. The pucks were then irradiated in air using a 10 MeV, 1 kW linear electron beam accelerator (AECL, Pinawa, Manitoba, Canada). The scan width and the conveyor speed was adjusted to achieve the desired dose rate per pass. The pucks were irradiated to 61, 70, 80, 100, 140, and 160 kGy of total absorbed dose. For each absorbed dose level, six pucks were irradiated. For 61, 70, 80 kGy absorbed dose, the irradiation was completed in one pass; for 100, 140 and 160 kGy, it was completed in two passes.

Following the irradiation, three pucks out of each different absorbed dose level were heated to 150° C. for 2 hours to completely melt the crystals and reduce the concentration of free radicals to undetectable levels.

A. Properties of the Specimens Prepared in Example 20

A Perkin-Elmer DSC 7 was used with an ice water heat sink and a heating and cooling rate of 10° C. per minute with a continuous nitrogen purge. The crystallinity of the samples obtained from Example 20 was calculated from the weight of the sample and the heat of melting of polyethylene crystals (69.2 cal/gm). The temperature corresponding to the peak of the endotherm was taken as the melting point. In the case of multiple endotherm peaks, multiple melting points were reported.

The results obtained are shown in Table 20 as a function of total absorbed dose level. They indicate that crystallinity decreases with increasing dose level. At the absorbed dose levels studied, the polymer exhibited two melting peaks ($T_1=118°$ C., $T_2=137°$ C.) after the subsequent melting step.

TABLE 20

WIR-AM GUR 4150 barstock

| Irradiation dose (kGy) | T 1st peak after irradiation (° C.) | T 2nd peak after irradiation (° C.) | T 3rd peak after irradiation (° C.) | T 1st peak after subsequent melting (° C.) | T 2nd peak after subsequent melting (° C.) | Crystallinity after irradiation (%) | Crystallinity after subsequent melting (%) |
|---|---|---|---|---|---|---|---|
| 160 | 113.4 | 135.10 | 143.20 | 114 | 135.90 | 41.97 | 39.58 |
| 140 | 114.6 | 135.10 | 143.60 | 116.2 | 138.60 | 45.25 | 41.51 |
| 100 | 118.7 | 125.10 | 143.50 | 118.2 | 138.20 | 47.18 | 42.58 |
| 80 | 115.7 | NP | 142.00 | 119.1 | 137.60 | 50.61 | 44.52 |
| 70 | 114.8 | NP | 141.40 | 118.9 | 137.00 | 52.36 | 44.95 |
| 61 | 114.6 | NP | 140.20 | 119.1 | 136.00 | 53.01 | 45.04 |

*NP: The peak is not present

Example 21

Temperature Rise During WIR-AM Process

This example demonstrates that the temperature rises during the warm irradiation process leading to adiabatic partial or complete melting of the UHMWPE.

A GUR 4150 bar stock (made from ram extruded Hoescht Celanese GUR 4150 resin obtained from Westlake Plastics, Lenni, Pa.) was machined into a 8.5 cm diameter and 4 cm thick hockey puck. One hole was drilled into the body-center of the puck. A Type K thermocouple was placed in this hole. The puck was pre-heated to 130° C. in air convection oven. The puck was then irradiated using 10 MeV, 1 kW electron beam (AECL, Pinawa, Manitoba, Canada). The irradiation was carried out in air with a scan width of 30 cm. The dose rate was 27 kGy/min and the puck was left stationary under the beam. The temperature of the puck was constantly measured during irradiation.

FIG. 11 shows the temperature rise in the puck obtained during the irradiation process. Initially, the temperature is at the pre-heat temperature (130° C.). As soon as the beam is turned on, the temperature increases, during which time the UHMWPE crystals melt. There is melting of smaller size crystals starting from 130° C., indicating that partial melting occurs during the heating. At around 145° C. where there is an abrupt change in the heating behavior, complete melting is achieved. After that point, temperature continues to rise in the molten material.

This example demonstrates that during the WIR-AM process, the absorbed dose level (duration of irradiation) can be adjusted to either partially or completely melt the polymer. In the former case, the melting can be completed with an additional melting step in an oven to eliminate the free radicals.

Example 22

Method of Making UHMWPE Using Cold Irradiation and Adiabatic Heating with Subsequent Complete Melting (CIR-AM)

This example illustrates a method of making UHMWPE that has a cross-linked structure, and has substantially no detectable free radicals, by irradiating UHMWPE at a high enough dose rate to generate adiabatic heating of the UHM-WPE and by subsequently melting the polymer.

A GUR 4150 bar stock (made from ram extruded Hoescht Celanese GUR 4150 resin obtained from Westlake Plastics, Lenni, Pa.) was machined into 8.5 cm diameter and 4 cm thick hockey pucks. Twelve pucks were irradiated stationary, in air, at a dose rate of 60 kGy/min using 10 MeV, 30 kW electrons (E-Beam Services, Cranbury, N.J.). Six of the pucks were irradiated to a total dose of 170 kGy, while the other six were irradiated to a total dose of 200 kGy. At the end of the irradiation the temperature of the pucks was greater than 100° C.

Following the irradiation, one puck of each series was heated to 150° C. for 2 hours to melt all the crystals and reduce the concentration of free radicals to undetectable levels.

A. Thermal Properties of the Specimens Prepared in Example 22

A Perkin-Elmer DSC 7 was used with an ice water heat sink and a heating and cooling rate of 10° C. per minute with a continuous nitrogen purge. The crystallinity of the samples obtained from Example 22 was calculated from the weight of the sample and the heat of melting of polyethylene crystals (69.2 cal/gm). The temperature corresponding to the peak of the endotherm was taken as the melting point.

Table 21 summarizes the effect of total absorbed dose on the thermal properties of CIR-AM UHMWPE both before and after the subsequent melting process. The results obtained indicate one single melting peak both before and after the subsequent melting step.

TABLE 21

CIR-AM GUR 4150 barstock

| Irradiation dose (kGy) | T peak after irradiation (° C.) | T peak after subsequent melting (° C.) | Crystallinity after irradiation (%) | Crystallinity after subsequent melting (%) |
|---|---|---|---|---|
| 170 | 143.67 | 137.07 | 58.25 | 45.27 |
| 200 | 143.83 | 136.73 | 54.74 | 43.28 |

Example 23

Comparison of Tensile Deformation Behavior of Unirradiated UHMWPE. Cold-Irradiated and Subsequently Melted UHMWPE (CIR-SM), and Warm Irradiated and Partially Adiabatic Melted and Subsequently Melted UHMWPE (WIR-AM)

This example compares the tensile deformation behavior of UHMWPE in its unirradiated form, and irradiated forms via CIR-SM and WIR-AM methods.

The ASTM D638 Type V standard was used to prepare dog bone specimens for the tensile test. The tensile test was carried out on an Instron 4120 Universal Tester at a cross-head speed of 10 mm/min. The engineering stress-strain behavior was calculated from the load-displacement data following ASTM D638.

The dog bone specimens were machined from GUR 4150 hockey pucks (made from ram extruded Hoescht Celanese GUR 4150 resin obtained from Westlake Plastics, Lenni, Pa.) that were treated by CIR-SM and WIR-AM methods. For the CIR-SM, the method described in Example 8 was followed, while for WIR-AM, the method described in Example 17 was followed. In both cases, the total dose administered was 150 kGy.

FIG. 12 shows the tensile behavior obtained for the unirradiated control, CIR-SM treated, and WIR-AM treated specimens. It shows the variation in tensile deformation behavior in CIR-SM and WIR-AM treated UHMWPE, even though in both methods the irradiation was carried out to 150 kGy.

Those skilled in the art will be able to ascertain using no more than routine experimentation, many equivalents of the specific embodiments of the invention described herein. These and all other equivalents are intended to be encompassed by the following claims.

What is claimed is:

1. A preformed material for subsequent production of a wear resistant medical implant comprising a cross-linked consolidated Ultra High Molecular Weight Polyethylene (UHMWPE) produced by a method comprising the steps of:
    (a) irradiating consolidated UHMWPE to cross-link polyethylene molecules and to achieve an absorbed radiation dose and generate radiation-induced heat, wherein the UHMWPE is pre-heated to a temperature below the melting temperature of the UHMWPE;
    (b) following step (a), subsequently irradiating the consolidated cross-linked UHMWPE to achieve a subsequent absorbed radiation dose and generate further radiation-induced heat, wherein the temperature of the consolidated cross-linked UHMWPE is above room temperature and below the melting temperature of the consolidated cross-linked UHMWPE;
    (c) repeating step (b) until a total absorbed radiation dose of 7.5 to about 100 MRad is obtained; and
    (d) allowing the cross-linked consolidated UHMWPE to cool.

2. The preformed material of claim 1, wherein the step (c) is repeated at least twice.

3. The preformed material of claim 1, wherein the total absorbed radiation dose is about 10 to about 100 MRad.

4. The preformed material of claim 1, wherein the total absorbed radiation dose is from 7.5 to about 10 MRad.

5. The preformed material of claim 1, wherein three radiation doses are applied, and wherein the dose for each irradiation is about 7.5 MRad.

6. The preformed material of claim 1, wherein the UHMWPE has a weight average molecular weight of greater than 400,000, wherein the weight average molecular weight is the weight average molecular weight of the UHMWPE prior to cross-linking by irradiation.

7. The preformed material of claim 1, wherein the temperature of the consolidated UHMWPE at step (b) is at a temperature lower than the melting point of the polyethylene.

8. The preformed material of claim 1, wherein the method is further comprising the step of fashioning an implantable bearing component from the polyethylene.

9. The preformed material of claim 1, wherein the irradiation step precedes the fashioning step.

10. The preformed material of claim 1, wherein the polyethylene has a crystallinity less than 50%.

11. The preformed material of claim 1, wherein the polyethylene has a tensile elastic modulus of less than 940 MPa.

12. The preformed material of claim 1, wherein the UHMWPE has a lamellar thickness less than 290 Å.

13. The preformed material of claim 1, wherein the UHMWPE has a hardness less than 65 on the Shore D scale.

14. The preformed material of claim 1, wherein the UHMWPE has a hardness less than 55 on the Shore D scale.

15. The preformed material of claim 1, wherein the UHMWPE has a hardness less than 50 on the Shore D scale.

16. The preformed material of claim 1, wherein at least 50% of the UHMWPE does not dissolve in Decalin over a period of 24 hours.

17. The preformed material of claim 1, wherein the UHMWPE has a gel content of 99% or greater.

18. A method for increasing the wear resistance of a preformed Ultra High Molecular Weight Polyethylene (UHMWPE) comprising the steps of:
    (a) irradiating the preformed UHMWPE in the solid state to cross-link UHMWPE molecules and to achieve an absorbed radiation dose and generate radiation-induced heat, wherein the UHMWPE is pre-heated to a temperature below the melting temperature of the UHMWPE;
    (b) following step (a), subsequently irradiating the preformed cross-linked UHMWPE to achieve a subsequent absorbed radiation dose and generate further radiation-induced heat, wherein the temperature of the preformed cross-linked UHMWPE is above room temperature and below the melting temperature of the preformed cross-linked UHMWPE;
    (c) repeating step (b) until a total absorbed radiation dose of 7.5 to about 100 MRad is obtained; and
    (d) allowing the preformed cross-linked UHMWPE to cool.

19. The method for increasing the wear resistance according to claim 18, wherein the total radiation dose is about 10 to about 100 MRad.

20. The method for increasing the wear resistance according to claim 18, wherein the total radiation dose is from 7.5 to about 10 MRad.

21. The method for increasing the wear resistance according to claim 18, wherein the dose for each irradiation is about 7.5 MRad.

22. The method for increasing the wear resistance according to claim 18, wherein the total radiation dose is from 7.5 to about 20 MRad.

23. The method for increasing the wear resistance as set forth in claim 18, wherein the weight average molecular weight of the UHMWPE is greater than 400,000, wherein the weight average molecular weight is the weight average molecular weight of the UHMWPE prior to cross-linking by irradiation.

24. The method for increasing the wear resistance according to claim 18, wherein the method is further including the step of machining the preformed UHMWPE into a medical implant.

25. A medical device comprising a Ultra High Molecular Weight Polyethylene (UHMWPE) material produced by a method comprising the steps of:
    (a) irradiating consolidated UHMWPE to cross-link UHMWPE molecules and to achieve an absorbed radiation dose and generate radiation-induced heat, wherein the UHMWPE is pre-heated to a temperature below the melting temperature of the UHMWPE;
    (b) following step (a), subsequently irradiating the consolidated cross-linked UHMWPE to achieve a subsequent absorbed radiation dose and generate further radiation-induced heat, wherein the temperature of the consolidated cross-linked UHMWPE is above room temperature and below the melting temperature of the consolidated cross-linked UHMWPE;
(c) repeating step (b) until a total absorbed radiation dose of 7.5 to about 100 MRad is obtained; and
(d) allowing the cross-linked consolidated UHMWPE to cool.

* * * * *